(12) United States Patent
Ito et al.

(10) Patent No.: US 6,310,061 B2
(45) Date of Patent: Oct. 30, 2001

(54) PYRROLIDINYL AND PYRROLINYL ETHYLAMINE COMPOUNDS AS KAPPA AGONISTS

(75) Inventors: Fumitaka Ito, Chita-gun; Hiroshi Kondo, Handa, both of (JP)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/770,515

(22) Filed: Jan. 26, 2001

Related U.S. Application Data

(60) Division of application No. 09/254,805, filed as application No. PCT/IB97/01021 on Aug. 21, 1997, now Pat. No. 6,201,007, which is a continuation-in-part of application No. PCT/IB96/00957, filed on Sep. 18, 1996.

(51) Int. Cl.[7] .................. A61K 31/445; A61P 25/00; C07D 207/12; C07D 401/12
(52) U.S. Cl. .................... 514/231.5; 514/235.5; 514/237.5; 514/318; 514/326; 514/330; 514/331; 514/332; 514/340; 514/343; 514/422; 514/423; 514/424; 514/111; 514/124; 514/131; 514/141; 546/193; 546/208; 546/216; 546/226; 546/229; 546/268.1; 546/276.4; 546/279.1; 548/518; 548/523; 548/530
(58) Field of Search ................ 514/231.5, 318, 514/332, 343; 544/111, 141; 546/193, 229, 276.4; 548/518

(56) References Cited

FOREIGN PATENT DOCUMENTS

| | | |
|---|---|---|
| 325406 | 1/1989 | (EP) . |
| 374756 | 12/1989 | (EP) . |
| 483580 | 10/1991 | (EP) . |
| 9418165 | 1/1994 | (WO) . |
| 9630339 | 3/1996 | (WO) . |

*Primary Examiner*—Jane C. Oswecki
(74) *Attorney, Agent, or Firm*—Peter C. Richardson; Paul H. Ginsburg; Grover F. Fuller, Jr.

(57) ABSTRACT

A compound of the following formula:

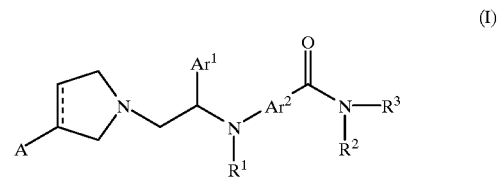

and the salts thereof, wherein A is hydrogen, halo, or hydroxy; the broken line represents an optional double bond with proviso that if the broken line is a double bond, then A is absent; $Ar^1$ is optionally substituted phenyl; $Ar^2$ is aryl or heteroaryl selected from phenyl, napththyl, or pyridyl, the aryl or heteroaryl being optionally substituted; $R^1$ is hydrogen, hydroxy, or $C_1$–$C_4$ alkyl; and $R^2$ and $R^3$ are independently selected from optionally substituted $C_1$–$C_7$ alkyl, $C_3$–$C_6$ cycloalkyl, $C_2$–$C_6$ alkenyl, $C_2$–$C_6$ alkynyl, or $R^2$ and $R^3$, together with the nitrogen atom to which they are attached, form an optionally substituted pyrrolidine, piperidine or morpholine ring. These compounds are useful as kappa agonists.

4 Claims, No Drawings

PYRROLIDINYL AND PYRROLINYL ETHYLAMINE COMPOUNDS AS KAPPA AGONISTS

This is a division of U.S. application Ser. No. 09/254,805 filed Mar. 12, 1999, now U.S. Pat. No. 6,201,007, which, in turn, is the national phase of international application number PCT/IB97/01021 filed Aug. 21, 1997, which, in turn, is a continuation-in-part of international application number PCT/IB96/00957 filed Sep. 18, 1996.

TECHNICAL FIELD

This invention relates to novel pyrrolidinyl and pyrrolinyl ethylamine compounds and their pharmaceutically acceptable salts, and to pharmaceutical compositions containing them. The pharmaceutically active compounds of this invention can be used as a selective kappa-receptor agonist.

BACKGROUND ART

Opioid analgesics such as morphine are therapeutically useful, but their usage is strictly limited because of their side effects such as drug dependency and abuse. Thus, analgesics with high usefulness and reduced tendency to cause drug dependency are desired. Considerable pharmacological and biochemical studies have been carried out to discover the opioid peptides and opioid receptors, and the discovery of the subtype of opioid receptor such as mu ($\mu$), delta ($\delta$), kappa ($\kappa$) in a variety of species, including human, has made a beginning towards creating new analgesics. As it is thought that opioid analgesics such as morphine act as a mu-receptor agonist, separating the action based on a kappa-receptor agonist from the action based on mu-receptor agonist has been investigated. Recently kappa-selective agonists (kappa-agonists) have been reported from the above viewpoint for example, EMD-61753: A. Barber et al., *Br. J. Pharmacol.*, Vol. 113, pp. 1317–1327, 1994. Some of them actually have been studied in clinical trials (*Med. Res. Rev.*, Vol. 12, p. 525, 1992).

European Patent No. EP 0254545 B1 discloses a variety of ethylenediamine compounds. European Patent No. EP 0483580 A2 discloses a variety of pyrrolidine compounds as analgesics. International Publication WO 96/30339 discloses a wide variety of pyrrolidinyl hydroxamic acid compounds as selective kappa-receptor agonists.

BRIEF DISCLOSURE OF THE INVENTION

The present invention provides a compound of the following formula:

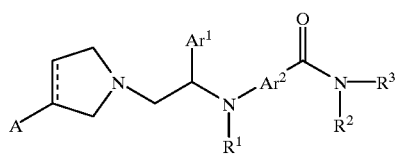

(I)

and the salts thereof, wherein

A is hydrogen, halo, hydroxy, $C_1$–$C_6$ (preferably $C_1$–$C_4$) alkyl, halo $C_1$–$C_6$ (preferably $C_1$–$C_4$) alkyl, $C_1$–$C_6$ (preferably $C_1$–$C_4$) alkoxy, halo $C_1$–$C_6$ (preferably $C_1$–$C_4$) alkoxy, oxo, OY wherein Y is a hydroxy protecting group, or absent;

the broken line represents an optional double bond with proviso that if the broken line is a double bond, then A is absent;

$Ar^1$ is phenyl optionally substituted by one or more (preferably one to two) substituents selected from halo, hydroxy, $C_1$–$C_4$ alkyl, $C_1$–$C_4$ alkoxy, $C_1$–$C_4$ alkoxy-$C_1$–$C_4$ alkoxy, $CF_3$, carboxy-$C_1$–$C_4$ alkoxy and $C_1$–$C_4$ alkoxy-carbonyl-$C_1$–$C_4$ alkoxy;

$Ar^1$ is aryl or heteroaryl selected from phenyl, naphthyl, pyridyl thienyl, furyl pyrrolyl and pyrimidyl, the aryl or heteroaryl being optionally substituted by one or more (preferably one to two) substituents selected from halo, hydroxy, amino, nitro, carboxy, $C_1$–$C_4$ alkyl $C_1$–$C_4$ alkoxy, $C_1$–$C_4$ alkylamino, di $C_1$–$C_4$ akylo, halo $C_1$–$C_4$ alkyl, $C_1$–$C_4$ alkylthio and sulfonyl methyl;

$R^1$ is hydrogen, hydroxy, $C_1$–$C_4$ alkyl, $C_1$–$C_4$ alkoxy or OY wherein Y is a hydroxy protecting group; and $R^2$ and $R^3$ are independently selected from hydrogen, hydroxy, $C_1$–$C_7$ alkyl optioaally substituted by one or more (preferably one to five) hydroxy or halo, $C_3$–$C_6$ cycloalkyl, $C_2$–$C_6$ alkenyl, $C_2$–$C_6$ alkynyl, $C_1$–$C_7$ (preferably $C_1$–$C_5$) alkoxy, phenyl optionally substituted by halo (preferably substituted by one or two halogen atoms), phenyl $C_1$–$C_7$ (preferably $C_1$–$C_5$) alkyl, halo substituted phenyl $C_1$–$C_7$ alkyl, and $(CH_2)_nX$—$R^4$ wherein n is one or two, X is O, NH or S and $R^4$ is $C_1$–$C_3$ alkyl, or when $Ar^2$ is phenyl, —$Ar^2$—$C$(=O)—N ($R^2$)— is a phthalimide group and $R^3$ is $C_1$–$C_7$ alkyl, or $R^2$ and $R^3$, together with the nitrogen atom to which they are attached, form a pyrrolidine, piperidine or morpholine ring, optionally substituted by $C_1$–$C_3$ alkyl or halo.

When $Ar^2$ is phenyl, $R^2R^3N$—C(=O)— is preferably at the meta or para position on the phenyl ring with respect to 2-(A-pyrrolydinyl)-1-$Ar^1$-ethyl-N($R^1$)—. When oxo is selected as "A" group, it is apparent that the oxygen atom should be attached to the pyrrolidinyl group through a double bond.

The pyrrolidinyl and pyrrolynyl ethylamine compounds of the present invention of formula (I) exhibit good kappa-receptor agonist activity, and thus are useful as an analgesic, anesthetic, anti-inflammatory or neuroprotective agent, and also useful in the treatment of arthritis, stroke or functional bowel disease such as abdominal pain, for the treatment of a mammalian subject, especially a human subject. Specifically, these compounds are useful as an analgesic for acute and chronic pain. Especially, these compounds are useful as an analgesic at central nervous system in the mammalian subject. Also, these compounds are useful as an analgesic for peripheral mediated inflammatory pain caused, for example by burns (induced by a contact with heat, acid or the other agents), scald (induced by a contact by hot liquid or steam), rheumatism or the like, in the said subject.

Accordingly, the present invention provides a pharmaceutical composition, which is useful as an analgesic, anesthetic, anti-inflammatory or neuroprotective agent, and also useful in the treatment of the above-mentioned diseases, which comprises a therapeutically effective amount of the compound of the formula (I), and a pharmaceutically inert carrier.

The present invention also provides a method for the treatment of a medical condition for which agonist activity toward opioid kappa-receptor is needed, in a mammalian subject, which comprises administering to said subject a therapeutically effective amount of the compound of the formula (I).

DETAILED DISCLOSURE OF THE INVENTION

In this specification, the term "hydroxy protecting group" means a functional group to protect a hydroxy group against undesirable reactions during synthetic procedures, including, but not limited to benzyl, benzoyl, methoxymethyl, tetrahydropyranyl and trialkylsilyl.

The term "$C_1$–$C_6$ alkyl" is used herein means a straight or branched alkyl including but not limited to methyl, ethyl, n-propyl iso-propyl, n-butyl, sec-butyl, tert-butyl and the like.

The term "$C_1$–$C_6$ alkoxy" is used herein to mean a straight or branched —OR (R is $C_1$–$C_6$ alkyl) including, but not limited to, methoxy, ethoxy, propoxy, isopropoxy, n-butoxy, iso-butoxy, tert-butoxy and the like.

The term "halo" means F, Cl Br or I, preferably F or Cl.

The term "halo $C_1$–$C_6$ alkyl" means a straight or branched, halo-substituted alkyl of 1 to 6 carbon atoms including, but not limited to methyl, ethyl, n-propyl, iso-propyl, n-butyl, sec-butyl and tert-butyl, substituted by 1 to 13 (preferably one to five) halogen atoms.

The term "halo $C_1$–$C_6$ alkoxy" means $C_1$–$C_6$ alkoxy substituted by 1 to 13 (preferably one to three) halogen atoms.

The term "halo substituted phenyl $C_1$–$C_7$ alkyl" means $C_1$–$C_7$ alkyl having a phenyl group attached to its terminal carbon atom, the phenyl group being substituted by one to five (preferably one to two) halogen atoms.

A preferred group of compounds of this invention includes the compounds of the formula (I) wherein A is hydrogen, halo, hydroxy, oxo or OY, or if the broken line is a double bond then A is absent;

$Ar^1$ is phenyl optionally substituted by one to three substituents selected from halo, hydroxy, $C_1$–$C_4$ alkoxy, carboxy $C_1$–$C_4$ alkoxy and $C_1$–$C_4$ alkoxycarbonyl-$C_1$–$C_4$ alkoxy;

$Ar^2$ is phenyl, pyridyl or thienyl, optionally substituted by one to two halo or $C_1$–$C_4$ alkoxy, $R^1$ is hydrogen, hydroxy or $C_1$–$C_4$ and; an $R^2$ and $R^3$ are independently selected from hydrogen, $C_1$–$C_7$ alkyl optionally substitutie by one or more hydroxy or halo, $C_3$–$C_6$ (preferably $C_3$–$C_4$) cycloalkyl, $C_2$–$C_6$ alkenyl, $C_2$–$C_6$ (preferably $C_2$–$C_3$) alkynyl, $C_1$–$C_4$ alkoxy phenyl and halo substituted phenyl $C_1$–$C_7$ alkyl when $Ar^2$ is phenyl —$Ar^2$—C(=O)—N ($R^2$)— is a phthalimide group and $R^3$ is $C_1$–$C_7$ alkyl, or $R^2$ and $R^3$, together with the nitrogen atom to which they are attached, form a pyrrolidine or morpholine ring.

A more preferred group of this invention includes the compounds of the formula (I) wherein A is hydrogen, fluorine, chlorine, hydroxy or OY wherein Y is methoxymethyl or tetrahydropyranyl; or if the broken line is a double bond then A is absent or;

$Ar^1$ is phenyl optionally substituted by chlorine, hydrory, methoxy or carboxymethoxy;

$Ar^2$ is phenyl, pyridyl or thienyl, optionally substituted by chlorine, fluorine or ethoxy;

$R^1$ is $C_1$–$C_4$ alkyl;

$R^2$ is $C_1$–$C_7$ (preferably $C_1$–$C_5$) alkyl optionally substituted by hydroxy or fluorine, $C_2$–$C_6$ (preferably $C_2$–$C_3$) alkenyl, halo substituted phenylmethyl or phenyl; and $R^3$ is hydrogen or methyl; or $R^2$ and $R^3$, together with the nitrogen atom to which they are attached, form a pyrrolidine or morpholine ring.

A more preferred group of this invention includes the compounds of the formula (I) wherein A is hydroxy, fluorine or chlorine; or if the broken line is a double bond, then A is absent; $Ar^1$ is phenyl optionally substituted by carboxymethoxy; $Ar^2$ is phenyl optionally substituted by methoxy or pyridyl; $R^1$ is $C_1$–$C_4$ alkyl; $R^2$ is $C_1$–$C_7$ alkyl optionaliy substitute by hydroxy; and $R^3$ is hydrogen.

Preferred individual compounds are:

4-{N-[2-(3-(S)-hydroxypyrrolidin-1-yl)-1-(S)-phenylethyl]-N-methylamino}-N'-propylbenzamide;

4-{N-[2-(3-(S)-hydroxypyrroidin-1-yl)-1-(S)-phenylethyl]-N-methylamino}-2-methoxy-N'-propylbenzamide;

6-{N-[2-(3-(S)-hydroxypyrrolidin-1-yl)-1-(S)-phenlethyl]-N-methylamino}-N'-propylpicolinamide;

4-{N-[1-(S)-(3-carboxymethoxyphenyl)-2-(3-(S)-hydroxypyrrolidin-1-yl)-ethyl]-N-methylamino)-N'-propylbenzamide;

4-{N-[2-(3-(S)-fluoropsrrolidin-1-yl) 1-(S)-phenylethyl]-N-methylamino}-N'-propylbenzamide;

4-{N-[2-(3-(S)-hydroxypyrrolidin-1-yl)-1-(S)-phenylethyl]-N-methylamino}-N'-(2-(S)-hydroxypropyl)benzamide;

5-{N-[2-(3-(S)-fluoropyrrolidin-1-yl)-1-(S)-phenylethyl]-N-methylamino}-N'-propylpicolinamide;

4-{N-methylamino-N-[2-(3-pyrrolin-1-yl)-1-(S)-phenylethyl]}-N'-propylbenzamide; and 4-{N-[2-(3-(S)-chloropyrrolidin-1-yl)-1-(S)-phenylethyl]-N-methylamino}-N'-(2-(S)-hydroxypropyl)benzamide.

Other preferred individual compounds are:

4-{N-[2-(3-(S)-hydroxypyrrolidin-1-yl)-1-(S)-phenylethyl]-N-methylamino}-N'-isopropylbenzamide;

3-{N-[2-(3-(S)-hydroxypyrrolidin-1-yl)-1-(S)-phenylethyl]-N-methylamino}-N'-propylbenzamide;

2-chloro-4-{N-[2-(3-(S)-hydroxypyrrolidin-1-yl)-1-(S)-phenylethyl]-N-methylamino}-N'-propylbenzamide;

4-{N-[2-(3-(S)-hydroxypyrrolidin-1-yl)-1-(S)-phenylethyl]-N-methylamino}-3-methoxy-N'-propylbenzamide;

3-chloro-4-{N-[2-(3-(S)-hydroxypyrrolidin-1-yl)-1-(S)-phenylethyl]-N-methylamino}-N'-propylbenzamide;

4-{N-[1-(S)-(3-hydroxyphenyl)-2-(3-(S)-hydroxypyrrolidin-1-yl)-ethyl]-N-methylamino}-N'-propylbenzamide;

4-{N-[2-(3-(S)-hydroxypyrrolidin-1-yl)-(S)-(3-methoxyphenyl)-ethyl]-N-methylamino}-N'-propylbenzamide;

4-{N-[1-(S)-phenyl-2-(pyrrolidin-1-yl)ethyl]-N-methylamino}-N-propylbenzamide;

4-{N-[1-(S)-(3-chlorophenyl)-2-(3-(S)-hydroxypyrrolidin-1-yl)-ethyl]-N-methylamino}-N'-propylbenzamide;

4-{N-[2-(3-(S)-hydroxypyrrolidin-1-yl)-1-(R)-phenylethyl]-N-methylamino}-N'-propylbenzamide;

4-{N-[2-(3-(S)-hydroxypyrrolidin-1-yl)-1-(S)-phenylethyl]-N-methylamino}-pyrrolidinebenzamide;

4-{N-[2-(3-(S)-hydroxypyrrolidin-1-yl)-1-(S)-phenylethyl]N-methylamino}-morpholinebenzamide;

4-{N-[2-(3-(S)-hydroxypyrrolidin-1-yl)-1-(S) phenylethyl]-N-methylamino}-N'-(2-(R)-hydroxypropyl)benzamide;

4-{N-[2-(3-(S)-hydroxypyrrolidin-1-yl)-1-(S)-phenylethyl]-N-methylamino}-N'-isobutylbenzamide;

4-{N-[2-(3-(S)-hydroxypyrrolidin-1-yl)-1-(S)-phenylethyl]-N-methylamino}-N'-allylbenzamide;

4-{N-[2-(3-(S)-hydroxypyrrolidin-1-yl)-1-(S)-phenylethyl]-N-methylamino}-N'-(3,3,3,-trifluoropropyl)benzamide;

3-fluoro-4-{N-[2-(3-(S)-hydroxypyrrolidin-1-yl)-1-(S)-phenylethyl]-N-methylamino}-N'-propylbenzamide;

4-{N-[2-(3-(S)-hydroxypyrrolidin-1-yl)-1-(S)-phenylethyl]-N-methylamino}-N'-(2,2,3,3,3,-pentafluoropropyl)benzamide;

4-{N-[2-(3-(S)-hydroxypyrrolidin-1-yl)-1-(S)-phenylethyl]-N-methylamino}-N'-tert-amylbenzamide;

5-{N-[2-(3-(S)-hydroxypyrrolidin-1-yl)-1-(S)-phenylethyl]-N-methylamino}-N'-propylpicolinamide;

4-{N-[2-(3-(S)-fluoropyrrolidin-1-yl)-1-(S)-phenylethyl]-N-methylamino}-N'-(2-(S)-hydroxypropyl)benzamide;

2-chloro-4-{N-[2-(3-(S)-fluoropyrrolidin-1-yl)-1-(S)-phenylethyl]-N-methylamino}-N'-propylbenzamide; and 4-{N-[2-(3-(S)-chloropyrrolidin-1-yl)-1-(S)-phenylethyl]-N-methylamino}-N'-propylbenzamide.

Other preferred compounds are:

4-{N-[2-(3-(S)-hydroxypyrrolidin-1-yl)-1-(S)-phenylethyl]-N-methylamino}-N'-methylbenzamide;

4-{N-[2-(3-(S)-hydroxypyrrolidin-1-yl)-1-(S)-phenylethyl]-N-methylamino}-N'-ethylbenzamide;

4-{N-[2-(3-(S)-hydroxypyrrolidin-1-yl)-1-(S)-phenylethyl]-N-methylamino}-N'-butylbenzamide;

4-{N-[2-(3-(S)-hydroxypyrrolidin-1-yl)-1-(S)-phenylethyl]-N-methylamino}-N'-pentylbenzamide;

4-{N-[2-(3-(S)-hydroxypyrrolidin-1-yl)-1-(S)-phenylethyl]-N-methylamino}-N'-phenylbenzamide;

4-{N-[2-(3-(S)-hydroxypyrrolidin-1-yl)-1-(S)-phenylethyl]-N-methylamino}-N'-(2-chlorobenzyl)benzamide;

4-{N-[2-(3-(S)-hydroxypyrrolidin-1-yl)-1-(S)-phenylethyl]-N-methylamino}-N',N'-dimethylbenzamide;

4-{N-[2-(3-(S)-hydroxypyrrolidin-1-yl)-1-(S)-phenylethyl]-N-methylamino}-N'-methyl-N'-propylbenzamide;

5-{N-[2-(3-(S)-hydroxypyrrolidin-1-yl)-1-(S)-phenylethyl]-N-methylamino}-N'-propyl-2-thiophenecarboxamide;

4-{N-[2-(3-(S)-hydroxypyrrolidin-1-yl)-1-(S)-phenylethyl]amino}-N'-propylbenzamide;

4-{N-[2-(3-(S)-hydroxypyrrolidin-1-yl)-1-(S)-phenylethyl]-N-methylamino}-N'-propylphthalimide;

4-{N-[2-(3-(S)-hydroxypyrrolidin-1-yl)-1-(S)-phenylethyl]-N-methylamino}-N'-ethoxybenzamide;

4-{N-[2-(3-(S)-hydroxypyrrolidin-1-yl)-1-(S)-phenylethyl]-N-methylamino}-N'-(3-hydroxypropyl)benzamide;

4-{N-[2-(3-(S)-hydroxypyrrolidin-1-yl)-1(S)-phenylethyl]-N-methylamino}-N'-cyclopropylbenzamide;

4-{N-[2-(3-(S)-hydroxypyrrolidin-1-yl)-1-(S)-phenylethyl]-N-methylamino}-N'-(S)sec-butylbenzamide;

4-{N-[2-(3-(S)-hydroxypyrrolidin-1-yl)-1-(S)-phenylethyl]-N-methylamino}-N'-(R)-sec-butylbenzamide;

4-{N-[2-(3-(S)-hydroxypyrrolidin-1-yl)-1-(S)-phenylethyl]-N-methylamino}-N'-propargylbenzamide;

4-{N-[1-(R)-(3-carboxymethoxyphenyl)-2-(3-(S)-hydroxypyrrolidin-1-yl)-ethyl]-N-methylamino}-N'-propylbenzamide;

4-{N-[2-(3-(S)-hydroxypyrrolidin-1-yl)-1-(S)-phenylethyl]-N-methylamino}-N'-tert-butylbenzamide;

4-{N-hydroxy-N-[2-(3-(S)-hydroxypyrrolidin-1-yl)-1-(S)-phenylethyl]amino}-N'-propylbenzamide;

4-{N-[2-(3-(S)-fluoropyrrolidin-1-yl)-1-(S)-phenylethyl]-N-hydroxyamino}-N'-propylbenzamide;

4-{N-[2-(3-(R)-fluoropyrrolidin-1-yl)-1-(S)-phenylethyl]-N-methylamino}-N'-propylbenzamide;

4-{N-[2-(3-(S)-fluoropyrrolidin-1-yl)-1-(R)-phenylethyl]-N-methylamino}-N'-propylbenzamide;

4-{N-[2-(3-(S)-chloropyrrolidin-1-yl)-1-(S)-phenylethyl]-N-methylamino}-N'-(2-(R)-hydroxypropyl)benzamide; and 4-{N-[2-(3-oxopyrrolidin-1-yl)-1-(S)-phenylethyl]-N-methylamino}-N'-propylbenzamide.

Further, the present invention provides a compound of the following formula:

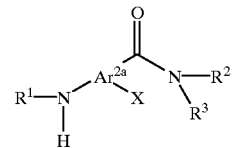

(VId)

wherein $Ar^{2a}$ is phenyl, pyridyl or thienyl;

X is hydrogen, halo or $C_1$–$C_7$ alkoxy;

$R^1$ is hydrogen, optionally protected hydroxy or $C_1$–$C_4$ alkyl; and $R^2$ and $R^3$ are independently hydrogen or $C_1$–$C_7$ alkyl optionally substituted by hydroxy or halo.

Preferred individual compounds of the formula (VId) are:

4-methylamino-N'-propylbenzamide;

5-N-mthylamio-N'-propylpicolinamide;

2-chloro-4-methylamino-N'-propylbenzamide;

4-methylamino-N'-(2-(S)-hydroxypropyl)benzamide;

4-methylamino-N'-(2-(R)-hydroxypropyl)benzamide;

4-methylamino-N'-(2,2,3,3,3-pentafluoropropyl)benzamide; and 4-methylamino-N'-tert-amylbezamide.

Further, the present invention provides compounds selected from 2-(3-(S)-fluoropyrrolidin-1-yl)-1-(S)-phenylethanol;

2-(3-(S)-fluoropyrrolidin-1-yl)-2-(R)-phenylethanol;

2-(R)-phenyl-2-(3-pyrroline-1-yl)ethanol;

2-(3-(R)-fluoropyrrolidin-1-yl)-1-(S)-phenylethanol;

2-(3-(R)-fluoropyrrolidin-1-yl)-2-(R)-phenylethanol;

2-(3-(S)-fluoropyrrolidin-1-yl)-1-(R)-phenylethanol;

2-(3-(S)-fluoropyrrolidin-1-yl)-2-(S)-phenylethanol;

2-(3-(S)-chloropyrrolidin-1-yl)-1-(S)-phenylethanol; and 2-(3-(S)-chloropyrrolidin-1-yl)-2-(R)-phenylethanol.

Further, the present invention provides processes for producing a compound of formula (I), which comprises reacting an amide compound of the formula (VId):

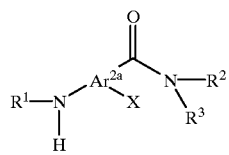

(VId)

with an ethanol compound selected from compounds (Va), (Vb) and (Vc), and a mixture of compounds (Va) and (Vb):

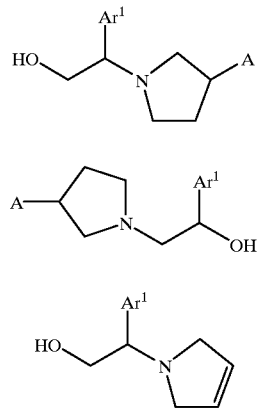

in the absence or presence of a base in a reaction inert solvent.

General Synthesis

The kappa agonists (kappa-receptor agonists) of formula (I) of this invention can be prepared as described in the following schemes. Unless otherwise indicated, in the reaction schemes that follow, A, $Ar^1$, $Ar^2$, $R^1$, $R^2$ and $R^3$ are defined as above.

Scheme 1a

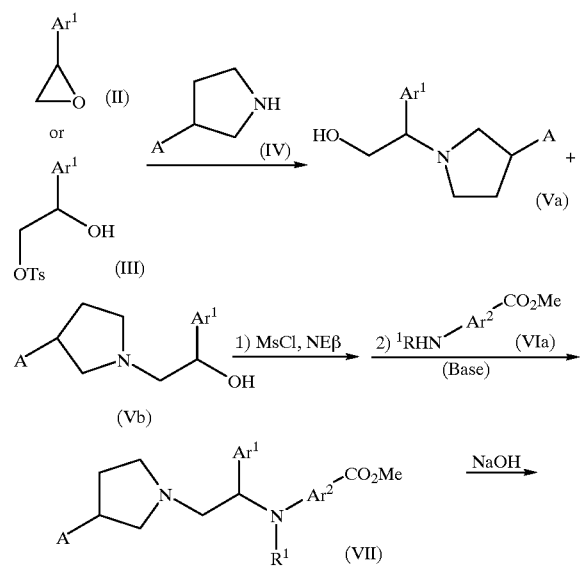

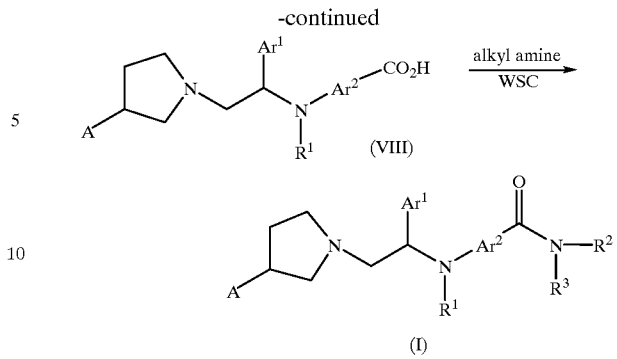

In the above Scheme 1a, an optionally substituted styrene oxide (II) or an optionally substituted phenyl-1,2-ethanediol 2-tosylate (III) can be reacted with a pyrrolidine compound (IV) in the absence or presence of a base such as $K_2CO_3$ to form a mixture of substituted pyrrolidinyl ethanols (Va) and (Vb). This reaction may be carried out in the absence or presence of a reaction inert solvent (e.g., methanol (MeOH), ethanol (EtOH), isopropylalcohol, tetrahydroftiran (THF), dioxane, N,N-dimethylformamide (DMF), dimethylsulfoxide (DMSO), methylene chloride ($CH_2Cl_2$), water, benzene, toluene, n-hexane or cyclohexane). This reaction can be carried out at a temperature from −78° C. to the reflux temperature of the solvent, preferably at from room temperature to a reflux temperature of the solvent for 5 minutes to 48 hours, preferably from 0.5 to 12 hours. The compound (Va) or the mixture of the compounds (Va) and (Vb), can be treated with methanesulfonyl chloride in the presence of a base such as triethylamine in a proper solvent such as dichloroethane, followed by coupling with a methyl ester compound of formula (VIa) to give an intermediate compound (VII). This coupling reaction can be carried out, in the absence or presence of a base such as sodium hydride (NaH), in a suitable polar solvent such as water, EtOH or DMF, at from room temperature to reflux temperature of the solvent, for 15 minutes to 6 hours.

Then, the intermediate compound (VII) may be treated with a base such as NaOH in a reaction inert solvent such as methanol, at a temperature from 0 to 100° C. for 5 minutes to 12 hours to give a carboxylic acid compound (VIII).

The carboxylic acid (VIII) can be reacted with an alkyl amine in the presence of a carbodiimide compound to give the pyrrolydinyl ethylamine compound (I). A convenient carbodiimide compound is 1-ethyl-3-(3-dimeythylaminopropyl)carbodiimide (WSC). This reaction may be carried out by contacting substantially equivalent amounts of the carboxylic acid and alkylamine with a small excess amount of the carbodiimide in an appropriate solvent. Appropriate solvents are inert aromatic hydrocarbons, ethers, halogenated hydrocarbons, especially dichloromethane. The reaction may take place at a temperature in the range from −30 to 100° C., usually from 0 to 30° C. for 30 minutes to 24 hours, usually 12 to 16 hours at room temperature. The resulting product can be isolated and purified by standard techniques.

If required, the hydroxy protecting group in A of the compound (I) obtained (i.e., Y of —OY), can be removed by the appropriate method for the particular protecting group chosen. For example, a typical protecting group methoxymethyl, can be removed by acid catalyzed hydrolysis in the presence of acid catalyst such as HCl. A further convenient protecting group in A is the tetrahydropylanyl group (THP). This can be also removed by acid-catalyzed hydrolysis. Appropriate acid catalysts are organic acids, inorganic acids, or Lewis acids such as acetic acid (AcOH), p-toluenesulfonic acid (p-TsOH), hydrochloric acid (HCl), and dimethylaluminium chloride (Me$_2$AlCl). Preferred acid catalyst is HCl.

An optically inactive compound (I) wherein Ar$^1$ is optionally substituted phenyl, can be prepared by subjecting a corresponding optically inactive 1-phenyl-1,2-ethanediol 2-tosylate of the formula (III) or 1-phenyl-2-pyrrolidinylethanol (Vb) to the reactions described in Scheme 1a. Optically inactive compounds (III), wherein Ar$^1$ is optionally substituted phenyl, may be prepared according to the procedures described in for example Tetrahedron, Vol. 47, pp. 9861–9866, 1991, Cehm. Rev., Vol. 80, pp. 187–213, 1980 or J. Org. Chem., Vol. 47, pp. 1229–1232, 1982, followed by tosylation such as reaction with p-toluanesulfonyl chloride in pyridine at 0° C. Optically inactive (Vb) can be prepared according to the procedures described for example in Tetrahedron Lett., Vol. 35, pp. 1511–1514, 1994 followed by a conventional reduction.

A compound of the formula (I) wherein A is hydroxy, R$^2$ is alkoxy and R$^3$ is hydrogen, can be obtained from a methylbenzoate of formula (VII) wherein A is hydroxy. First the hydroxy group of the methylbenzoate compound may be protected with a suitable protecting group such as tert-butyldimethysilyl group. Second the hydroxy-protected methyl ester compound can be subjected to hydrolysis to give the corresponding carboxylic acid. Then the carboxylic acid can be subjected to amidation to give the compound (I). The hydroxy protection can be conducted by subjecting the compound of the formula (VII) in DMF to a reaction with tert-butyldimethylsilylchloride and immidazole solution at about 0° C. for 1 to 6 hours. The hydrolysis can be carried out in the presence of a base such as sodium hydroxide in a polar solvent such as methanol at about the reflux temperature of the solvent for from 1 to 10 hours. The aridation can be carried out with a desired O-alkylhydroxylamine in the presence of a carbodiimide such as WSC at room temperature for from 1 to 24 hours. If deprotection is required, a conventional procedures can be employed. For example, when the hydroxy group is protected with tert-butyldimethylsilyl group, the amide compound can be treated with tetrabutylammonium fluoride in a proper solvent such as THF at room temperature.

A compound of formula (I), wherein A is absent and the broken line is a double bond, can be also prepared by subjecting a 2-phenyl-2-(3-pyrrolin-1-yl)ethanol compound (Vc) and a benzanude compound to the coupling reactions illusrated in Scheme 1a.

(Vc)

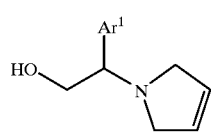

The ethanol coompound (Vc) can be prepared by reacting a corresponding phenylglicinol and 1,4-dichlorobutene in the presence of base such as Et$_3$N in a reaction inert solvent such as ethanol at the reflux temperature of the solvent for 1 to 24 hours.

A compound of the formula (I) wherein A is oxo (=O), can be prepared by oxidation of the corresponding pyrrolidinol compound. A suitable oxidation is Swern oxidation.

Further, the compounds of the formula (I) wherein —Ar$^2$—C(=O)—N (R$^2$)—, is a phthalimide group, can be prepared by using a compound of the formula (VIb):

(VIb)

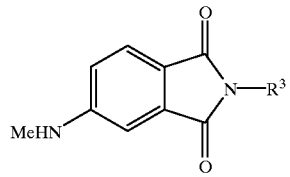

instead of the compound (VIa) in the above-mentioned Scheme 1a

Compounds of the formula (I) wherein Ar$^2$ is thienyl, can be prepared by using a methylaminothiophenecarboxamide of the formula (VIc):

(VIc)

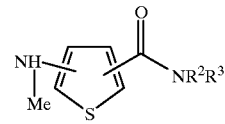

instead of the compound (VIa) in the above-mentioned Scheme 1a. Compounds (VIc) can be prepared, first, by reacting a nitrothiophenecarboxaldehyde with the Jones reagent to give a nitrothiophenecarboxylic acid. Then, the carboxylic acid obtained can be subjected to condensation with a compound of the formula: NHR$^2$R$^3$, and then to reduction of the nitro group with iron powder and ammonium chloride, followed by methylation of the amino group.

The compounds of formula (II), (III) and (IV) are either known compounds, which can be made by the known methods, or they are analogs of known compounds, which can be prepared by methods analogous to the known methods.

According to the well known procedures or the following procedures, R, S configuration of compounds (Va) and (Vb) can be selectively determined by subjecting a 3-pyrrolidinol with the corresponding R,S configuration.

Compounds of the fromula (Va) and (Vb) wherein A is fluorine and Ar$^1$ is phenyl can be prepared from a commercially available 1-benzyl-3-pyrrolidinol. First, hydroxy group of the pyrrolidinol can be converted to an appropriate leaving group such as p-toluenesulfonate. The conversion can be achieved by subjecting the ptrrolidinol to the reaction with p-toluenesulfonyl chloride in pyridine. Second, the leaving group may be replaced by fluorine by a reaction with a suitable fluorinating agent such as tetrabutylammonium fluoride in a reaction inert solvent such as THF. Then, the 3-fluoropyrrolidine can be subjected to hydrogenation followed by a coupling with a stylene oxide of formula (II). The hydrogenation can be carried out in the presence of a suitable catalyst such as paulladium hydroxide on carbon under hydrogen atmosphere in a reaction inert solvents such as EtOH at from 0° C. to a room temperature for 5 minutes to 48 hours preferably 12 to 36 hours. The coupling reaction can take place in the absence or presence of a reaction inert solvent such as EtOH.

Compounds of the fromula (Va) and (Vb) wherein A is chlorine and Ar$^1$ is phenyl, can also be prepared from 1-benzyl-3-pyrrolidinol. For example, the 1-benzyl-3-pyrrolidinol can be subjected to chlorination to give 1-benzyl-3-chloropyrrolidine The benzyl group of the 1-benzyl-3-chloropyrrolidine can be removed by treating the 1-benzyl-3-chloropyrrolidine with 1-chloroethyl chloroformate followed by coupling with styreneoxide of the formula (II). The chlorination 1-benzyl-3-pyrrolidinol can be carried out under a conventional condition, for example in the presence of a suitable reagent such as triphenylphosphine in a suitable solvent such as $CCl_4$ at room temperature. The debenzylation can be carried out accroding to the well known methods. The debenzylation is typically carried out in a reaction inert solvent such as dichloroethane at the reflux temperature of the solvent for 5 minutes to 3 hours. Then the solvent may be evaporated and the residue can be subjected to the coupling reaction with styrene oxide in a suitable solvent such as EtOH at the reflux temperature of the solvent for 5 minutes to 4 hours.

Compounds (Va) and (Vb) wherein A is halo and $Ar^1$ is a optionally substituted phenyl, can be prepared from a desired N-protected 3-pyrrolidinol compound via the corresponding N-protected 3-halopyrrolidine. First, 1-benzyl-3-pyrrolidinol can be treated with a suitable halogenation reagent in a reaction inert solvent for example, triphenylphosphine in $CCl_4$ at the reflux temperature of the solvent for from 3 to 36 hours. Second, the 1-benzyl3-chloropyrrolidine can be purified, and deprotection can be carried out under conditions known to skilled in the art (e.g., with 1-chloroethyl chlorofornate in dichloroethane at 0° C. for 30 minutes to 6 hours). Third, the 3-chloropyrrolidine can be treated with a styreneoxide compound to give the ethanols (Va) and (Vb) according to the procedures illustrated in Scheme 1a.

Methyl ester compounds of the formula (VIa), wherein $Ar^2$ is optionally substituted phenyl, are known compounds or can be prepared by treating a substituted 4-aminobenzoic acid compound with an alkylhalide in the presence of a base such as NaH or $Na_2CO_3$ in a reaction inert solvent such as DMF.

More specifically, the compounds of the formula (VIa) can be prepared by the following methods.

A: Methyl 3-methylaminobenzoate of the formula (VIa) can be prepared by first subjecting 3-acetamidebenzoic acid to methylation in the presence of a base such as NaH in a reaction inert solvent such as DMF, followed by deacetylation in the presence of an acid catalyst such as conc. sulfuric acid ($H_2SO_4$).

B: A compound of the formula (VIa) wherein $Ar^2$ is substituted by fluorine and $R^1$ is hydrogen, can be prepared from a nitrobenzoic acid by subjecting the nitrobenzoic acid to esterification followed by reduction. The esterification can be achieved in the presence of acid catalyst such as sulfimc acid in MeOH at the reflux temperate of the solvent for 1 to 12 hours. The reduction can be carried out in the presence of a reducing agent such as iron powder in a suitable solvent such as acetic acid at from room temperature to 60° C. for 0.5 to 6 hours. If desired, the amino group can be alkylated by a well known method. For example, first the methyl ester can be treated with trifluoroacetic anhydride in the presence of base such as $Na_2CO_3$ in a suitable solvent such as $CH_2Cl_2$, then can be alkylated with a suitable alkylating agent such as iodomethane. A compound of the formula (VIa) wherein $Ar^2$ is substituted by chlorine and $R^1$ is alkyl, can be prepared from a chlorobenzoic acid by alkylation. The alkylation can be take place in the presence of a base such as NaH with a suitable alkyl halide in a reaction inert solvent such as DMF at about 0° C. for 1 to 24 hours.

C: A compound of the formula (VIa), wherein $Ar^2$ is pyridyl; the methylester group is on the 3-position and the $R^1HN$— is on the 6-position of the pyridine ring respectively, can be prepared by esterification of a 6-aminonicotic acid.

The crude residue of the methyl ester obtained may be subjected to methylation of the amino group. A suitable esterificating agent is, for example, trimethylsilyldiazomethane. The methylation of the amino group can be carried out according to the same procedures of the above mentioned preparation of compounds (VIa).

Alternatively, an amide compound of the general formula (VId)

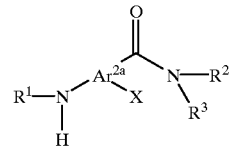

(VId)

wherein $Ar^{2a}$, X, $R^1$, $R^2$ and $R^3$ are defined as above, can be subjected to the coupling reason with compounds (Va) and (Vb) to directly give a compound (I). This coupling reaction can be carred out in the absence or presence of a base such as NaH in a reaction inert solvent. The preferred solvents include EtOH and DMF. The reaction can be carried out at a temperature in the range of −78° C. to the reflux temperature of the solvent, preferably from room temperature to the reflux temperature, for 5 minutes to 48 hours, preferably 0.5 to 24 hours.

The amide compounds of the formula (VId) can be prepared according to the procedures described below.

A: A compound of the formula (VId) wherein $Ar^{2a}$ is phenyl; $R^1$ is hydroxy and X is hydrogen, can be obtained by reduction of a known nitro N-alkylbenzamide compound. Suitable reducing agents include for example, zinc powder. This reduction can be carried out by adding the reducing agent to a mixture of the nitro N-alkylbenzamide compound and ammonium chloride at about room temperature (e.g., 20–25° C.) for from 1 to 3 hours.

B: A compound of the formula (VId) wherein $Ar^{2a}$ is phenyl; $R^1$ is hydrogen or $C_1$–$C_4$ alkyl; $R^2$ is $C_1$–$C_7$ alkyl optionally substituted by hydroxy; $R^3$ is hydrogen and X is hydrogen or halo, may be prepared from a known amino benzoic acid compound, wherein the phenyl ring is optionally substituted by halo. The benzoic acid can be subjected to amidation under the similar conditions to those illustrated in Scheme 1a. If desired, the amino group of the benzamide compound obtained can be alkylated. For example, preferable alkylating agent is alkylhalide, and this alkylation can be carried out in the presence of base such as potassium carbonate at about room temperature for 12 to 24 hours.

C: An amide compound (VId) wherein $Ar^{2a}$ is pyridyl, and —$NHR^1$ group is on the 5-position and the amide group is on the 2-position of the pyridine ring respectively, can be prepared by treating an amino-protected picolinic acid with oxalyl chloride followed by amidation with an desired alkyl amine. The treating of the 5-protected-amino picolic acid and oxalyl chloride can be performed in a reaction inert solvent such as $CH_2Cl_2$ or $DMF/CH_2Cl_2$ in the presence of a base such as triethylamine at room temperature. The amidation can be carried out in the presence of a base in a reaction inert solvent. The base is preferably triethylamme and the reaction may be conducted in a suitable solvent, e.g., dichloroethane at about 15° C. If required, the amino protecting group can be removed by the procedures known to those skilled in the art.

An alternative method to prepare the compounds of the formula (I) is illustrated in the following Scheme 1b.

Scheme 1b

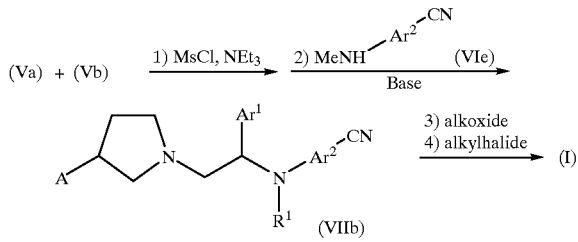

The mixture of the compounds (Va) and (Vb) can be treated with methanesulfonyl chloride in a similar way as shown in Scheme 1a, followed by coupling with a cyano compound (VIe) to give the compound of the formula (VIIb). This coupling reaction can be carried out in a reaction inert solvent such as DMF or ethanol, in the presence or absence of base such as NaH, NaNH$_2$ or 2,6-lutidine. This reaction may take place at from room temperature to the reflux temperature of the solvent for 30 minutes to 12 hours.

Then, the compound (VIIb) may be reacted with a suitable alkoxide such as t-BuOK in the presence of water, in a polar solvent such as t-BuOH. This reaction may take place at reflux tomperature of the solvent for 5 minutes to 6 hours. The, a proper alkyl halide can be added to the resulting reaction mixture. The mixture thus obtained is refluxed for 5 minutes to 5 hours. The target compound (I) can be isolated and purified from a resulting reaction mixture by standard techniques.

Cyano compounds of the formula (VIe), wherein Ar$^2$ is a substituted phenyl can be prepared by treating known substituted 4-aminobenzonitride compounds with NaH or K$_2$CO$_3$, followed by alkylation with an alkylhalide in a reaction inert solvent such as DMF.

The compounds of formula (I) of this invention are basic, and therefore they will form acid-addition salts. All such salts are within the scope of this invention. However, it is necessary to use an acid addition salts which is pharmaceutically-acceptable for administration to a mammal. The acid-addition salts can be prepared by standard methods, e.g., by contacting the basic and acidic compounds in substantially equivalent proportions in water or an organic solvent such as methanol or ethanol, or a mixture thereof. The salts can be isolated by evaporation of the solvent. Typical salts which can be formed are the hydrochloride, nitrate, sulfate, bisulfate, phosphate, acetate, lactate, citrate, tartrate, succinate, malate, fumarate, gluconate, saccharate, benzoate, methanesulfonate, p-toluenesulfonate, oxalate and pamoate (1,1'-methylene-bis-(2-hydroxy-3-naphtoate)) salts.

The compounds of formula (I) of this invention, wherein Ar$^1$ is phenyl substituted by carboxy-C$_1$-C$_4$ alkoxy are acidic, and they will form base salts. All such salts are within the scope of this invention. However, it is necessary to use a base salt which is pharmaceutically-acceptable for administration to a mammal. The base salts can be prepared by standard methods, e.g., by contacting the acidic and basic compounds in substantially equivalent proportions in water or an organic solvent such as methanol or ethanol, or a mixtre thereof. The salts can be formed are the sodium, potassium, calcium and magnesium salts, and also salts with ammonia and amines, such as ethylamine, diethylamine, cyclohexylamine, piperidine or morpholine salts.

Also included within the scope of this invention are bioprecursors (also called as pro-drugs) of the kappa agonist compounds of the formula (I). A bioprecursor of a kappa agonist of formula (I) is a chemical derivative thereof which is readily converted back into the parent compound of formula (I) in biological systems. In particular, a bioprecursor of a kappa agonist of formula (I) is converted back to the parent compound of formula (I) after the bioprecursor has been administered to, and absorbed by, a mammalian subject, e.g., a human subject. For example, it is possible to make a bioprecursor of a kappa agonist of the invention of formula (I) in which one or both of A and R$^1$ is hydroxy groups by making an ester of the hydroxy group. When only one of A and R$^1$ is a hydroxy group, only mono-esters are possible. When both A and R$^1$ are hydroxy, mono- and di-esters (which can be the same or different) can be made. Typical esters are simple alkanoate esters, such as acetate, propionate, butyrate, etc. In addition, when A or R$^1$ is a hydroxy group, bioprecursors can be made by converting the hydroxy group to an acyloxymethyl derivative (e.g., a pivaloyloxymethyl derivative) by reaction with an acyloxymethyl halide (e.g., pivaloyloxymethyl chloride).

The kappa agonists compounds of the present invention of fomula (I) exhibit significant agonist activity toward opioid kappa-receptor and are thus useful as an analgesic, anesthetic, anti-inflammatory agent or neuroprotective agent, and also useful in the treatment of arthritis, stroke or functional bowel disease such as abdominal pain, for the treatment of a mammalian subject, especially a human subject.

The activity of the kappa-agonists compounds of formula (I) of the present invention, is demonstrated by the opioid receptor binding activity. Such activity may be determined in homogenate from guinea pig whole brain, as described by Regina, A. et al., in *J. Receptor Res.*, Vol. 12: pp. 171–180, 1992. In summary, tissue homogenate is incubated at 25° C. for 30 min in the presence of labelled ligand and test compounds. The mu-sites are labelled by 1 nM of (3H)-[D-Ala2, MePhe4, Gly-ol5]enkephalin (DAMGO), the delta-sites by 1 nM of (3H)-[D-Pen2,5]enkephalin (DPDPE) and tne kappa-sites by 0.5 nM (3H)-CI-977. The non specific binding is measured by use of 1 $\mu$M CI-977 (kappa), 1 $\mu$M (DAMGO) (mu), 1 $\mu$M (DPDPE) (delta). Data are expressed as the IC$_{50}$ values obtained by a non-linear fitting program using the Cheng and Prusoff equation. Some compounds prepared in the Examples showed a potent IC$_{50}$ value against kappa receptor in the range of 0.01 to 100 nM.

The analgesic activity of the kappa-agonist compounds at the central nervous system caa also be demonstrated by the Formalin Test as described by Wheeler-Aceto, H. et al. in *Psychopharmacology*, Vol. 104: pp. 35–44, 1991. In this testing, male SD rats (80–100 g) are injected s.c. with a test compound dissolved in 0.1% methyl cellulose saline or vehicle. After 30 min., 50 $\mu$l of a 2% formalin are injected into a hind paw. The number of licking the injected paw per observation period is measured 15–30 min. after the injection of formalin and expressed as % inhibition compared to the respective vehicle group. Some compounds prepared in the Examples showed a potent ED$_{50}$ value in the range of less than 25 mg/kg p.o.

The activity of the kappa agonists, against peripheral acute-pain, can be demonstrated by the Randall-Selitto assay (M. E. Planas, *Pain*, Vol.60, pp. 67–71, 1995). In this testing Male SD rats (100–120 g) were used and the nociceptive threshold at the right paw was measured by Randall-Selitto (Ugo Basile) method. After three days of acclimation of assay condition, experiments were carried out. Hyperalgesia was induced by the intraplantar injection of a 0.1 ml/right paw of 1% solution of carrageenin. Painful pressure were delivered to the right plantar via a wedge-shaped piston and the level of response were measured at 3.5 and 4.5 hr later the carrageenin injection. Some compounds, prepared in the working examples as described below, were tested in accordance with the above procedures, and showed good activity against acute-pain (i.e., $ED_{50}$ value of less than 10 mg/kg p.o.).

The activity of the kappa agonists, against chronic pain at the periphery, can be demonstrated by the adjuvant-induced hyperalgesia, according to the procedure described by Judith S. Waker et al., as reported in *Life Sciences*, Vol. 57, PP. 371–378, 1995. In this testing, male SL rats, weighing 180–230 g at the time of inoculation, were used. To produce adjuvant arthritis, rats were anesthetized with ether and inoculated intradermally into the footpad of the right hindpaw with 0.05 ml of *Mycobacterium butyricum* suspended in paraffin oil (2 mg/ml). Nociceptive threshold was evaluated by paw pressure test, using same procedures of the Randall-Selitto assay (as being described above), and edema was measured as the width of foot. Assays were done through the whole period.

The sedation function of kappa agonists can be determined by the Rotarod Test as described by Hayes, A. G. et al. in *Br. J. Pharmacol.*, Vol. 79, pp. 731–736, 1983. In this testing, a group of 6–10 male SD rats (100–120 g) are selected for their ability to balance on a rotating rod (diameter 9 cm, rate of rotation 5 r.p.m.). The selected rats are then injected s.c. with a test compound dissolved in 0.1% methyl cellulose saline. The animals are tested again 30 min. after treatment; a rat falling off the bar more than twice within 150 seconds is considered to be showing motor impairment and the animal's performance (i.e., time on the rotarod) are recorded. The $ED_{50}$ value, defined as the dose of the drug which have the performance time is observed in the control group. Some compounds, prepared in the working examples as described below, wae tested in accordance with the above procedures.

The diuresis function of the kappa agonists can be determined according to the procedure described by A. Barber et al., (*Br. J. Pharmacol.*, Vol. 111, pp. 843–851, 1994). Some compounds, prepared in the working examples as described below, were tested in accordance with the above procedures.

The kappa agonists compounds of formula (I) of this invention can be administered in either the oral, parenteral or topical routes to mammals. A preferable dosage level may be in a range of from 0.01 mg to 10 mg per kg of body weight per day although variations will necessarily occur depending upon the weight and condition of the subject being treated, the disease state being treated and the particular route of administration chosen. However, a dosage level that is in the range of from 0.01 mg to 1 mg per kg of body weight per day, single or divided dosage is most desirably employed in humans for the treatment of pain in a postoperative patient and a pain like hyperalgesia caused by chronic dises.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, trochees, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various nontoxic organic solvents, etc. Moreover, oral pharmaceutical compositions can be suitably sweetened and/or flavored. In general the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatine capsules; preferred materials in this connection also include lactose or milk sugar as well as high molecular weight polyethylene grycols. When aqueous suspensions and/or elixirs are desired for oral administration, the active ingredient may be combined with various sweetening or flavoring agents, coloring matter or dyes, and, if so desired, emulsifing and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well-known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

EXAMPLES AND PREPARATIONS

The present invention is illustrated by the following examples and preparations. However, it should be understood that the invention is not limited to the specific details of these examples and preparations. Melting points were taken with a Buchi micro melting point apparatus and uncorrected. Infrared Ray absorption spectra (IR) were measured by a Shimadzu infrared spectrometer (IR-470). $^1H$ and $^{13}C$ nuclear magnetic resonance spectra (NMR) were measured in $CDCl_3$ by a JEOL NMR spectrometer (JNM-GX270, 270 MHz) unless otherwise indicated and peak positions are expressed in parts per million (ppm) downfield from tetratethylsilane. The peak shapes are denoted as follows: s, singlet, d, doublet; t, triple; m, multiplet; br, broad.

Preparation 1

2-(3-(S)-Methoxymethoxypyrrolidin-1-yl)-2-(R)-phenylethanol

To a stirred solution of (S)-(—)-1,2,4-butanetriol (10.61 g, 0.1 mol) in pyridine (50 ml) was added to tolpenesulfonyl choride (38.13 g. 0.2 mol) by portins at 0° C. After 14 h stirring, the reaction mixture was poured into conc. HCl aqueous solution including ice and acidified to pH2. The irue was extracted with ether (100 ml×3). The extract combined was washed with brine, dried ($Na_2SO_4$), and concentrated to give 18.58 g of colorless oil. To a stirred solution of this crude ditosylate (18.58 g, 45.7 mmol) and dimethoxymethane (50 ml) in $CH_2Cl_3$ (50 ml) was added $P_2O_5$ by portions at rt (room temperature) and stirred for 26 h. The $CH_2Cl_4$ layer was separated and the $P_2O_5$ (50 g) solid was washed with $CH_2Cl_2$ (50 ml×4). The $CH_2Cl_2$ layer combined was washed with saturated $NaHCO_3$ aqueous solution and brine. After dry ($Na_2SO_4$), the solvent was evaporated to afford 18.01 g of brown viscous oil. A mixture of this oil (18.00 g, 40 nm), 1-(−) 2-phenylglycin 1 (4.80 nm, 35 nm and $Et_3N$ (11.3 ml, 80 mmol) in ethanol (20 ml) was refluxed with stirring for 8 h. The solvent was evaporated and the residue was dissolved in $CH_2Cl_2$ (200 ml). This solution was washed with saturated $NaHCO_3$ aqueous solution and brine, dried ($Na_2SO_4$), and concentrated to give 16.69 g of brown viscous oil, which was purified by column chromatography (silica gel 200 g, $CHCl_2$/MeOH: 20/1) to afford 5.13 g (20.4%, over all yield) of clear brown viscous oil.

$^1$NMR (270 MHz, $CDCl_3$) δ 7.40–7.25 (5H, m), 4.62 (1H, d, J=7.0 Hz), 4.58(1H, d, J=7.0 Hz), 4.25–4.15 (1H, m), 3.88 (1H, dd, J=5.9, 10.6 Hz), 3.80 (1H, dd, J=5.9, 10.6 Hz), 3.50 (1H, t, J=5.9 Hz), 3.33 (3H, s), 2.76 (1H, dt, J=6.2, 8.4 Hz), 2.71 (1H, dd, J=5.9, 10.3 Hz), 2.63 (1H, dd, J=3.3, 10.3 Hz), 2.45 (1H, dt, J=6.2, 8.1 Hz), 2.18 (1H, br, s), 2.16–2.02 (1H, m), 1.87–1.75 (1H, m). IR(neat): 3450 $cm^{-1}$.

Preparation 2

2-(3-(S)-Methoxymethoxypyrrolidin-1-yl)-1-(S) phenylethanol and 2-(3-(S)-Methoxymethoxypyrrolidin-1-yl-2-(R)-phenylethanol A mixture of 3-(S)-methoxymethoxypyrrolidine (4.37g, 33.3 mmol) and (S)-(−)-styrene oxide (4.00 g, 33.3 mmol) in EtOH (40 ml) was refluxed with stirring for 2 h. After evaporation of the solvent, the residue was purified by column chromatography (slicagel: 120 g, $CH_2Cl_2$:MeOH= 40:1–20:1) to give 4.91 g (58.7%) of pale yellow oil as 0.65 to 0.35 mixture of title compounds.

$^1$H NMR (270 MHz, $CDCl_3$) δ 7.40–7.27 (5H, m), 4.68–4.63 (2.65H, m), 4.35–4.15 (1H, m), 3.90–3.75 (0.7H, m), 3.49 (0.35H, t, J=5.9 Hz), 3.38 (1.95H,s), 3.32 (1.05H, s), 3.10–2.90 (1.3H, m), 2.80–2.40 (4H, m), 2.20–2.00 (1H, m), 1.95–1.75 (2H, m).

Preparation 3

2-(3-(S)-Methoxymethoxypyrrolidin-1-yl)-1-(S)-phenylethanol and 2-(3-(S)-Methoxymethoxyprrolidin-1-yl)-2-(R)-phenylethanol A mixture of 3-(S)-methoxymethoxyprrolidine (6.10 g, 46.5 mmol), (S)(+)-1-phenyl-1,2-ethanediol-2-tosylate (13.6 g, 46.5 mmol) and $K_2CO_3$ (7.06 g, 51.1 mmol) in EtOH (80 ml) was refluxed with stirring for 4.5 h. After evaporation of the solvent, $CH_2Cl_2$ was added to the residue and washed with saturated $NaHCO_3$ aqueous solution, brine, dried ($Na_2SO_4$), and concentrated to give 14.94 g of crude products, which was purified by column chromatography (suicagel: 150 g, $CH_2Cl_2$/(MeOH=50:1–20:1) to afford 7.75 g (66.4%) of brown oil as 0.65 to 0.35 mixture of title compounds.

$^1$H NMR (270 MHz, $CDCl_3$) δ 7.40–7.27 (5H, m), 4.68–4.63 (2.65H, m), 4.35–4.15 (1H, m), 3.90–3.75 (0.7H, m), 3.49 (0.35H, t, J=5.9 Hz), 3.38 (1.95H,s), 3.32 (1.05H, s), 3.10–2.90 (1.3H, m), 2.80–2.40 (4H, m), 2.20–2.00 (1H, m), 1.95–1.75 (2H, m).

Preparation 4

2-(R)-Phenyl-2-(3-(S)-tetrahydropyran-2-yloxypyrrolidin-1-yl)ethanol and 1-(S)-Phenyl-2-(3-(S)-tetrahydropyran-2-yloxypyrrolidin-1-yl)ethanol This was prepared from 3-(S)-tetrahydropyranyloxypyrrolidine (3.00 g, 17.5 mmol) and (S)-(−)-styrene oxide (2.10 g, 17.5 mmol) in 50% yield as 0.35 to 0.65 mixture of title compounds according to a procedure similar to that described in Preparation 2.

$^1$H NMR (270 MHz, $CDCl_3$) δ 7.50–7.20 (5H, m), 4.71 (0.65H, dd, J=3.3, 10.6 Hz), 4.65–4.50 (1H, m), 4.45–4.25 (1H, m), 3.95–3.75 (1.7H, m), 3.60–3.42 (1.35H, m), 3.20–2.40 (5.3H, m), 2.25–1.45 (9H, m).

Preparation 5

2-(R)-Phenyl-2-pyrrolidin-1-yl-ethanol and 1-(S)-Phenyl-2-pyrrolidin-1-yl-ethanol This was prepared from pyrrolidine (592 mg, 8.32 mmol), and (S)-(−)-styrene oxide (1.00 g, 8.32 mmol) in 96% yield as 0.3 to 0.7 mixture of title compounds according to a procedure similar Lo that described in Preparation 2.

$^1$H NMR (270 MHz, $CDCl_3$) δ 7.45–7.27 (5H, m), 4.70 (0.7H, dd, J=3.3, 10.6 Hz), 3.87 (0.3H, dd, J=5.9, 10.6 Hz), 3.81 (0.3H, dd, J=5.9. 10.6 Hz), 3.47 (0.3H, t, J=5.9 Hz), 2.90–2.70 (1.4H, m), 2.65–2.40 (4H, m), 1.90–1.60(5H, m).

Preparation 6

Methyl 3-methoxy-4-methylaminobenzoate

To a suspension of NaH (2.43 g, 60.7 ml) DMF (20 ml) was added a solution of 4-amino-3-hydroxybenzoic acid (3.00 g, 19.6 mmol) in DMF (20 ml) at 0° C. After stirring at room temperature for 1 H, iodomethane (3.78 ml, 60.7 mmol) was added to this mixture at 0° C. and stirred at room temperature for 16 h. The mixture was poured into ice water and extracted with nHex:AcOEt:$Et_2O$=1:1:1 (300 ml). The extract was washed with water, bine, dried ($Na_2SO_4$), and concentrated to give brown oil, which was purified by column chromato-graphy (silica gel 190 g, nHex/AcOEt= 10/1 and silica gel 35 g, $CH_2Cl_2$ only) to afford 481 mg (13%) of title compound.

$^1$H NMR (270 MHz, $CDCl_3$) δ 7.66 (1H, dd, J=1.8, 8.4 Hz), 7.40 (1H, d, J=1.8 Hz), 6.52 (1H, d, J=8.4 Hz), 4.72 (1H, br, s), 3.89 (3H, s), 3.86 (3H, s), 2.91 (3H, d, J=5.1 Hz).

Preparation 7

Methyl 2-methoxy-4-methylaminobenzoate

This was prepared from 4-amino-2-hydroxybenzoic acid (3.00 g, 19.6 mmol) in 22% yield according to a procedure similar to that descnbed in Preparation 6.

$^1$H NMR (270 MHz, $CDCl_3$) δ 7.77 (1H, d, J=8.8 Hz), 6.16 (1H, dd, J=2.2, 8.8 Hz), 6.08 (1H, d, J=1.8 Hz), 4.19 (1H, br. s), 3.88 (3H, s), 3.82 (3H, s), 2.89 (3H, d, J=5.1 Hz).

Preparation 8

Methyl 2-chloro-4-methylaminobenzoate

This was prepared from 4-amino-2-chlorobenzoic acid (2.00 g, 11.7 mmol) in 13% yield, according to a procedure similar to that described in Preparation 6.

$^1$H NMR (270 MHz, $CDCl_3$) δ 7.80 (1H, d, J=8.8 Hz), 6.59 (1H, d, J=2.6 Hz), 6.44 (1H, dd, J=2.6, 8.8 Hz), 4.21 (1H, br. s), 3.86 (3H, s), 2.87 (3H, d, J=5.1 Hz).

Preparation 9

3-Chloro-4-methylaminobenzonitrile

This was prepared from 4-amino-3-chlorobenzonitrile (2.00 g, 13.1 mmol) in 42% yield according to a procedure similar to that describer in Preparation 6.

$^1$H NMR (270 MHz, $CDCl_3$) δ 7.50 (1H, d, J31.8 Hz), 7.43 (1H, dd, J=1.8, 8.4 Hz), 6.61 (1H, d, J=8.4 Hz), 4.92 (1H, br. s), 2.96 (3H d, J=5.1 Hz).

Preparation 10
Methyl 6-methylaminonicotinate

To a suspension of 6-aminonicotinic acid (1.00 g, 7.24 mmol) in MeOH (20 ml) and MeCN (10 ml) was added 10% solution of trimethylsilyldiazomethane in $CH_2Cl_2$ (25 ml) at room temperature. After stirring at room temperature for 0.5 h, the solvent was evaporated to give crude methyl 6-aminonicotinate as a yellow solid. Title compound was prepared from this crude methyl 6-aminonicotinate in 17% yield according to a procedure sinular to that described in Preparation 6.

$^1$H NMR (270 MHz, $CDCl_3$) δ 8.75(1H, d, J=2.2 Hz), 8.01(1H, dd, J=2.2, 8.8 Hz), 6.36(1H, d, J=9.2 Hz), 5.11 (1H, br. s), 3.87(3H, s), 2.99(3H, d, J=5.5 Hz).

Preparation 11
Methyl 3-methylaminobenzoate

To a suspension of NaH (1.54 g, 38.5 mmol) in DMF (20 ml) was added a solution of 3-acetamidebenzoic acid (3.00 g, 16.7 mmol) in DMF (20 ml) at 0° C. After stirring at room temperature for 0.5 h, iodomethane (2.40 ml, 38.5 mmol) was added to this mixture at 0° C. and stirred at room temperature for 1.5 h. The mixture was poured into ice 6N-HCl aqueous solution and extracted with AcOEt:toluene=2:1 (200 ml×3). The extract was washed with water, brine, dried ($Na_2SO_4$), and concentrated to give 3.08 g of brown oil. A mixture of this brown oil and $cH_2SO_4$ (5 ml) in MEOH (30 ml) was refluxed with stirring for 7 h. After cooling down to room temperature, the solvent was evaporated. The residue was basified with saturated $NaHCO_3$ aqueous solution and extracted with $CH_2Cl_2$. The extracted was washed with water, brine, dried ($Na_2SO_4$), and concentrated to give 2.31 g (84%) of brown oil.

$^1$H NMR (270 MHz, $CDCl_3$) δ 7.37 (1H, dt, J=1.4, 7.5 Hz), 7.28–7.20 (2H, m), 6.78 (1H, ddd, J=0.73, 2.6 8.1 Hz), 3.89 (3H, s), 2.87 (3H, s).

Prearation 12
4-Amino-N'-propylphthalimide

To a suspension of NaH (493 g, 12.3 mmol) in DMF (10 ml) was added a solution of 4-aminophthalimide (2.00 g, 12.3 mmol) in DMF (10 ml) at 0° C. After stirring at room temperature for 1 h, iodopropane (1.20 ml, 12.3 mmol) was added to this mixture at 0° C. and stirred at room temperature for 28 h. The mixture was poured into water and reacted with AcOEt:toluene 2:1 (150 ml×3). The extract was washed with water, brine, dried ($Na_2SO_4$), and concentrated to give yellow solid, which was purified by column chromatography (silica gel: 130 g, $CH_2Cl_2$ only to $CH_2Cl_2$/MeOH=75/1) to give 1.14 g (45%) of yellow solid.

$^1$H NMR (270 MHz, $CDCl_3$) δ 7.59 (1H, d, J=8.1 Hz), 7.03 (1H, d, J=2.2 Hz), 6.81 (1H, dd, J=2.2, 8.1 Hz), 4.32 (2H, br. s), 3.65–3.55 (2H, m), 1.80–1.60 (2H, m), 0.93(3H, t, J=7.3 Hz).

Preparation 13
4-Methylamino-N'-propylphthalimide

This was prepared from 4-amino-N'-propylphthalmide in 11% yield according to a procedure similar to that described in Preparation 12.

$^1$H NMR (270 MHz, $CDCl_3$) δ 7.59 (1H, d, J=8.4 Hz), 6.96 (1H, d, J=2.2 Hz), 6.71 (1H, dd, J=2.2, 8.4 Hz), 4.50 (1H, br. s), 3.65–3.55 (2H, m), 2.95 (3H, d, J=5.1 Hz), 1.80–1.60 (2H, m), 0.93 (3H,t, J=7.3 Hz).

Preparation 14
5-Nitro-2-thiophenecarboxylic Acid

To a solution of 5-nitro-2-thiophenecarboxaldehyde (1.00 g, 6.24 mmol) in acetone (50 ml) was added Jones reagent (8N in acetone, 8.12 ml, 65 mmol) at −20° C. After stirring for 1H, 30 ml of isopropanol was added to the mixture. $H_2O$ was added to the mxure and extracted with $CH_2Cl_2$. The exact was washed with water, brine, dried ($Na_2SO_4$), and concentrated to give 967 mg (90%) of yellow amorphous.

$^1$H NMR (270 MHz, $CDCl_3$) δ 7.88 (1H, J=4.4 Hz), 7.66 (1H, d, J=4.0 Hz), 5.14 (1H, br. s).

Preparation 15
5-Nitro-N-propyl-2-thiophenecarboxamide

To a solution of 5-nitro-2-thiophenecarboxylic acid (967 mg, 5.59 mmol) in DMF (0.745 ml) and $CH_2Cl_2$ (4 ml) was added oxalyl chloride at 0° C. After stirring for 0.5 h at rt (room temperature), the solvent was evarated below 30° C. to give yellow oil and solid. To a solution of n-propylamine (0.551 ml, 6.71 mmol) in $Et_3N$ (1.87 ml 13.4 mmol) and $CH_2Cl_2$ (25 ml) was added a solution of crude acid chloride in $CH_2Cl_2$ (10 ml) below 20° C. After stirring for 4 h at rt, the mixture was washed with water, saturated $NaHCO_3$ aqueous solution. water, brine, dried ($Na_2SO_4$), and concentrated to give brown solid, which was purified by column chromatography (silica gel 50 g, $CH_2Cl_2$/MeOH=100/1–30/1) to afford 815 mg (68%) of white solid.

$^1$H NMR (270 MHz, $CDCl_3$) δ 7.85 (1H, d, J=4.0 Hz), 7.35 (1H, d, J=4.4 Hz), 6.12 (1H, br. s), 3.50–3.35 (2H, m), 1.75–1.55 (2H, m), 0.99 (3H,t, J=7.3 Hz).

Preparation 16
5-Amino-N'-propyl-2-thiophenecarboxamide

A mixture of 5-nitro-N-propyl-2-thiophenecarboxamide (815 mg, 3.81 mmol), iron powder (1.06 g, 19.0 mmol) and $NH_4Cl$ (102 mg, 1.90 mmol) in EtOH (12 ml) and $H_2O$ (6 ml) was refluxed with stirring for 2 h. The reaction mixture was filtered and washed with EtOH. The combined filtrate was evaporated. The residue was dissolved in AcOEt and washed with water, brine, dried ($Na_2SO_4$), and concentrated to give brown amorphous, which was purified by column chromatography (silica gel 40 g, $CH_2Cl_2$/MeOH=40/1) to afford 411 mg (59%) of brown amorphous.

$^1$H NMR (270 MHz, $CDCl_3$) δ 7.09 (1H, d, J=3.7 Hz), 6.07 (1H, d, J=4.0 Hz), 5.80–5.60 (1H, m), 4.14 (2H, br. s), 3.40–3.25 (2H, m), 1.70–1.50 (2H, m), 0.96 (3H,t, J=7.3 Hz).

Preparation 17
5-Methylamino-N'-propyl-2-thiophenecarboxamide

To a solution of 5-amino-N'-propyl-2-thiophenecarboxamide (411 mg, 2.23 mmol) in $CH_2Cl_2$(12 ml) was added $Na_2CO_3$ (710 mg, 6.70 mmol) and trifluoroacetic anhydride (0.631 ml, 4.47 mmol) at rt. After stirring for 5 h, the solid was filtered off. The filtrate was washed with water and brine, dried ($Na_2SO_4$) and concentrated to give 396 mg of yellow oil. To a solution of this oil in DMF (6.5 ml) was added $Na_2CO_3$ (2.35 g, 22.2 mmol) and iodomethane (2.90 ml, 46.6 mmol) at rt. After stirring for 22 h. the mixture was poured into ice 1N-HCl and extracted with AcOEt:toluene=2:1 The extract was washed with water, brine, dried ($Na_2SO_4$), and concentrated to give 298 mg of orange solid. To a solution of this solid in MeOH (3.5 ml) was added 7% $K_2CO_3$ aqueous solution (1.8 ml) at rt. After stirring for 18 h, the solvent was evaporated. The residue was dissolved in AcOEt and water. The organic layer was washed with water, brine, dried ($Na_2SO_4$), and concentrated to give brown oil, which was purified by column chromatography (silica gel 15 g, $CH_2Cl_2$/MeOH=60/1–40/1) to afford 122.5 mg (44%) of title compound.

$^1$H NMR (270 MHz, $CDCl_3$) δ 7.16 (1H, d, J=4.0 Hz), 5.89 (1H d, J=4.4 Hz), 5.68 (1H, br. s), 4.32 (1H, br. s), 3.40–3.30 (2H, m), 2.91 (3H d, J=5.1 Hz), 1.70–1.50 (2H, m), 0.96 (3H,t, J=7.3 Hz).

Preparation 18
(S)-1-(3-Methoxymethoxyphenyl)-1,2-ethanediol

A mixture of 3-methoxymethoxystyrene (prepared by methoxymethylation of 3-hydroxystyrene in a standard mnanner) (1.54 g, 9.39 mmol), and AD-mix-α (13.18 g, 9.41 mmol) in water (48 ml) and t-BuOH (48 ml) was stirred at 0° C. for 6.5 h. To this reaction mixture was added $Na_2SO_3$ (14.13 g) and the mixture was stirred at rt for 1 H. The reaction mixture was extracted with ethyl acetate. The extract was washed with brine, dried ($Na_2SO_4$), and concentrated to give light brown oil, which was purified by column chromatography (silica gel: 90 g, ethyl acetate/hexane:1/2–3/1) to afford 1.69 g (91%) of desired product as colorless oil.

$^1$H NMR (270 MHz, $CDCl_3$) δ 7.25 (1H, dd, J=7.7, 8.1 Hz), 7.03 (1H, d, J=1.8 Hz), 6.98–6.92 (2H, m), 5.15 (2H, s), 4.74 (1H, dd, J=3.3, 8.1 Hz), 3.71 (1H, br.d, J=9.9 Hz), 3.65–3.55 (2H, m, including 1H, dd, J=8.1, 11.0 Hz at 3.61 ppm, CHCH2OH), 3.44 (3H, s), 3.14 (1H, br.s, OH).

Preparation 19
(S)-1-(3-Methoxymethoxyphenyl)-1,2-ethanediol-2-tosylate

To a stirred solution of (S)-1-(3-methoxymethoxyphenyl)-1,2-ethanediol (1.69 g, 8.54 mmol) in pyridine (20 ml) was added p-toluenesulfonyl chloride (1.63 g, 8.54 mmol) and 4-dimethylaminopyridine (1.04 g, 8.54 mmol) at 0° C. and the reaction mixture was stirred at 0° C. to rt for 16 h at 60° C. for 1 h. The reaction mixture was acidified with 2N HCl aqueous solution and extracted with ethyl acetate. The extract was washed with water and brine, dried ($Na_2SO_4$), and concentrated to give brown oil, which was purified by column chromatography. (silica gel: 150 g, ethyl acetate/hexane:1/2 to 2/1) to afford 2.01 g (67%) of desired product as colorless oil. Its optical purity was 98% ee by HPLC.

$^1$H NMR (270 MHz, $CDCl_3$) δ 7.77 (2H, d, J=8.4 Hz), 7.34 (2H, d, J=8.1 Hz), 7.25 (1H, dd, J=7.7, 8.4 Hz), 7.00–6.92 (3H, m), 5.15 (2H, s), 4.95 (1H, ddd, J=3.3, 3.3, 8.4 Hz), 4.15 (1H, dd, J=3.3, 10.3 Hz), 4.03 (1H, dd, J=8.4, 10.3 Hz), 3.46 (3H, s), 2.65 (1H, d, J=3.3 Hz), 2.45 (3H, s).

Preparation 20
2-(R)-(3-Methoxymethoxyphenyl)-2-(3-(S)-methoxymethoxyprrolidin-1-yl)ethanol and 1-(S)-(3-Methoxymethoxyphenyl)-2-(3-(S)-methoxymethoxypyrrolidin-1-yl)ethanol This was prepared from (S)-1-(3-methoxymethyloxyphenyl)-1,2-ethanediol-2-tosylate in 79% yield as 0.25 to 0.75 mixture of title compounds according to a procedure similar to that described in Preparation 3.

$^1$H NMR (270 MHz, $CDCl_3$) δ 7.29–7.21 (1H, m), 7.09–6.91 (3H, m), 5.22–5.13 (2H, m), 4.80–4.55 (2.75H, m), 4.33–4.15 (1H, m), 3.90–3.72 (0.5H, m), 3,51–3.45 (0.25H, m), 3.48 (3H, s), 3.38 (2.25H, s), 3.33 (0.75H, s), 3.05–2.90 (1.5H, m), 2.80–2.43 (4H, m), 2.23–2.02 (1H, m), 1.95–1.70 (2H, m).

Preparation 21
(S)-1-(3-Chlorophenyl)-1,2-ethanediol

This was prepared from 3-chlorostyrene in 100% yield according to a procedure similar to that described in Preparation 18.

$^1$H NMR (270 MHz, $CDCl_3$) δ 7.40–7.20 (4H, m), 4.90–4.75 (1H, m), 3.85–3.75 (1H, m), 3.75–3.60 (1H, m), 2.66 (1H, d, J=2.9 Hz), 2.20–2.05 (1H, m).

Pretaration 22
(S)-1-(3-Chlorophenyl)-1,2-ethanediol-2-tosylate

This was prepared from (S)-1-(3-chlorophenyl)-1,2-ethanediol in 74% yield according to a procedure similar to that described in Preparation 19. Its optical purity was 98% ee by HPLC.

$^1$H NMR (270 MHz, $CDCl_3$) δ 7.76 (2H, d, J=8.1 Hz), 7.32 (2H, d, J=8.4 Hz), 7.31–7.17 (4H, m), 5.00–4.92 (1H, m), 4.14 (1H, dd, J=3.3, 10.6 Hz), 4.02 (1H, dd, J=8.4, 10.6 Hz), 2.63 (1H, d, J=3.7 Hz), 2.46 (3H, s).

Preparation 23
2-(R)-(3-Chlorophenyl)-2-(3-(S)-methoxymethoxypyrrolidin-1-yl)ethanol and 1-(S)-(3-Chlorophenyl)-2-(3-(S)-methoxymethoxypyrrolidin-1-yl) ethanol This was prepared from (S)-1-(3-chlorophenyl)-1,2-ethanediol-2-tosylate in 62% yield as 0.15 to 0.85 mixture of title compounds according to a procedure similar to that described in Preparation 3.

$^1$H NMR (270 MHz, $CDCl_3$) δ 7.40–7.20 (4H, m), 4.80–4.57 (2.85H, m), 4.32–4.15 (1H, m), 3.85–3.80 (0.3H, m), 3.48–3.40 (0.15H, m), 3.38 (2.55H, s), 3.34 (0.45H, s), 3.05–2.92 (1.7H, m), 2.80–2.62 (2H, m), 2.58–2.40 (2H m), 2.23–2.05 (1H, m), 1.95–1.80 (1H, m).

Preparation 24
(R)-1-Benzyl-3-pyrrolidinol-tosylate

To a stirred solution of (R)-1-benzyl-3-pyrrolidinol (1.77 g, 10 mmol) in pyridine (30 ml) was added p-toluenesulfonyl chloride (9.53 g, 50 mmol) by portions a, 0° C. After 90 h stirring it room temperature, water was added to the reaction mixture and the mixture was extracted with ether (150 ml). The extract was washed with water brine, dried ($Na_2SO_4$), and concentrated to give 3.06 g (92%) of brown oil.

$^1$H NMR (270 MHz, $CDCl_3$) δ 7.76 (2H, d, J=8.4 Hz), 7.31 (2H, d, J=8.4 Hz), 7.35–7.20 (5H, m), 5.05–4.90 (1H, m), 3.61 (1H, d, J=12.8 Hz), 3.54 (1H, d, J=12.8 Hz), 2.76 (1H, dd, J=6.0, 11.2 Hz), 2.75–2.60 (1H, m), 2.55–2.35 (2H, m), 2.44(3H, s), 2.12–2.05 (1H, m), 2.03–1.90 (1H, m).

Preparation 25
(S)-1-Benzyl-3-fluoropyrrolidine

To a solution of (R)-1-benzyl-3-pyrrolidinol-tosylate (3.06 g 9.24 mmol) in THF (30 ml) was added 1.0M solution of tetrabutylammonium fluoride in THF (37.0 ml, 37.0 mmol) at room temperature. After 1.5 h stirring at reflux temperature, water (150 ml) was added to the reaction mixture and the mixture was extracted with ethyl acetate (100 ml×2). The combined extract was washed with water, brine, dried ($Na_2SO_4$), and concentrated to give brown oil, which was purified by column chromatography (silica gel: 80 g, $CH_2Cl_2$/MeOH:50/1) to afford 1.18 g (71%) of brown oil.

$^1$H NMR (270 MHz, $CDCl_3$) δ 7.45–7.20 (5H, m), 5.29–5.00 (1H, m), 3.68 (1H, d, J=13.2 Hz), 3.63 (1H, d, J=12.8 Hz), 2.95–2.60 (3H m), 2.55–2.38 (1H, m), 2.30–1.90 (2H, m).

Preparation 26
2-(3-(S)-Fluoropyrrolidin-1-yl)-1-(S)-phenylethanol and 2-(3-(S)-Fluoropyrrolidin-1-yl)-2-(R)-phenylethanol A suspension mixture of (S)-1-benzyl-3-fluoropyrrolidine (1.18 g, 6.58 mmol) and 20% palladium hydroxide on carbon (354 mg) in EtOH (20 ml) was stirred under hydrogen atmosphere at room temperature for 21.5 h. After removal of the catalyst by Celite filtration, to this solution was added a solution of (S)-(−)-styrene oxide (791 mg, 6.58 mmol) in EtOH (5 ml). The mixture was refluxed with stirring for 3.5 h. After evaporation of the solvent, the residue was purified by column chromatography (slicagel: 80 g, $CH_2Cl_2$:MeOH=40:1–30:1) to give 713 mg (51.8%) of yellow oil as 0.7 to 0.3 mixture of title compounds.
$^1$H NMR (270 MHz, $CDCl_3$) δ 7.45–7.20 (5H, m), 5.35–5.05 (0.7H, m), 5.25–4.95 (0.3H, m), 4.71 (0.7H, dd, J=3.3, 10.6 Hz), 3.95–3.75 (0.6H, m), 3.52 (0.3H, t, J=5.9 Hz), 3.15–2.40 (5.4H, m), 2.30–1.80 (3H, m).

Preparation 27
2-(3-(S)-Methoxymethoxypyrrolidin-1-yl)-1-(R)-phenylethanol and 2-(3-(S)-Methoxymethoxypyrrolidin-1-yl)-2-(S)-phenylethanol
This was prepared from 3-(S)-methoxymethoxypyrrolidine and (R)-(−)-styrene oxide in 53% yield as 0.7 to 0.3 mixture of title compounds according to a procedure similar to that described in Preparation 2.
$^1$H NMR (270 MHz, $CDCl_3$) δ 7.40–7.20 (5H, m), 4.72 (0.7H, dd, J=3.3, 10.6 Hz), 4.66 (0.7H, d, J=7.0 Hz), 4.63 (0.7H, d, J=7.0 Hz), 4.63–4.56 (0.6H, m), 4.35–4.17 (1H, m), 3.92–3.77 (0.6H, m), 3.50 (0.3H, t, J=5.5 Hz), 3.37 (2.1H,s), 3.33 (0.9H, s), 3.10–2.50 (5.4H, m), 2.25–2.00 (1H, m), 1.95–1.70 (2H, m).

Preparation 28
(R)-1-(3-Methoxymethoxyphenyl)-1,2-ethanediol
This was prepared from 3-methoxymethoxystyrene and AD-mix-β in 100% yield according to the procedures similar to those described in Preparation 18.
$^1$H NMR (270 MHz, $CDCl_3$) δ 7.31–7.25 (1H, m), 7.06–6.96 (3H, m), 5.18 (2H, s), 4.80 (1H, dd, J=3.7, 8.1 Hz), 3.78 (1H, dd, J=3.7, 11.4 Hz), 3.66 (1H, dd, J=8.1, 11.4 Hz), 3.48(3H, s).

Preparation 29
(R)-1-(3-Methoxymethoxyphenyl)-1,2-ethanediol-2-tosylate
This was prepared from (R)-1-(3-methoxymethoxyphenyl)-1,2-ethanediol in 77% yield according to the procedures similar to those described in Preparation 19
$^1$H NMR (270 MHz, $CDCl_3$) δ 7.77 (2H, d, J=8.4 Hz), 7.33 (2H, d, J=7.7 Hz), 7.28–7.18 (1H, m), 7.00–6.92 (3H, m), 5.15 (2H, s), 5.00–4.90 (1H, m), 4.20–4.00(2H, m), 3.46 (3H, s), 2.80–2.60 (1H, m), 2.45 (3H, s). 97% ee (by HPLC)

Preparation 30
2-(R)-Phenyl-2-(3-pyrroline-1-yl)ethanol
This was prepared from R-(−)-2-phenylglycinol and cis-1,4-dichloro-2-butene in 58% yield according to the procedures similar to those described in Preparation 1.
$^1$H NMR (270 MHz, $CDCl_3$) δ 7.36–7.29(5H, m), 5.77 (2H, s), 3.83(2H, d, J=5.9 Hz), 3.66(1H,m), 3.50(4H, s).

Preparation 31
(S)-1-Benzyl-3-pyrrolidinol-tosylate
This was prepared from (S)-1-benzyl-3-pyrrolidinol and p-toluenesulfonyl chloride in 98% yield according to the procedures similar to those described in Preparation 24.
$^1$H NMR (270 MHz, $CDCl_3$) δ 7.76(2H, d, J=8.4 Hz), 7.33–7.26(7H, m), 4.97(1H, t, J=2.9 Hz), 3.69–3.58(2H, m), 2.89–2.83(1H, m), 2.73–2.68(2H, m), 2.58–2.55(1H, m), 2.44(3H, s), 2.20–2.12(1H, m), 1.99–1.93(1H, m).

Preparation 32
(R)-1-Benzyl-3-fluoropyrrolidine
This was prepared from (S)-1-benzyi-3-pyrrolidinol-tosylate in 61% yield according to the procedures similar to those described in Preparation 25.
$^1$H NMR (270 MHz, $CDCl_3$) δ 7.33–7.23(5H, m), 5.28–5.04(1H, m), 3.71–3.61(2H, m), 2.91–2.67(3H, m), 2.50–2.42(1H, m), 2.24–2.00(2H m).

Preparation 33
2-(3-(R)-Fluoropyrrolidin-1-yl)-1-(S)-2-phenylethanol and 2-(3-(R)-Fluoropyrrolidin-1-yl)-2-(R)-phenylethanol
This was prepared (R)-1-benzyl-3-fluoropyrrolidine in 76% over all yield as 0.6 to 0.4 mixture of title compounds according to the procedures similar to those described in Preparation 26.
$^1$H NMR (270 MHz, $CDCl_3$) δ 7.40–7.24(5H, m), 5.32–5.27(0.3H, m), 5.25–5.21(0.2H, m), 5.11–5.07(0.3H, m), 5.07–5.01(0.2H, m), 4.71(0.6H, dd, J=3.3, 10.3 Hz), 3.90–3.78(0.6H, m), 3.55–3.51(0.4H, m), 3.13–2.44(5.4H, m), 2.23–1.94(2H, m).

Preparation 34
2-(3-(S)-Fluoropyrrolidin-1-yl)-1-(R)-phenylethanol and 2-(3-(S)-Fluoropyrrolidin-1-yl)-2-(S)-phenylethanol
This was prepared from 3-(S)-fluoropyrrolidine and (R)-(+)-styreneoxide in 72% yield as 0.7 to 0.3 mixture of the title compounds according to the procedures similar to those described in Preparation 26.
$^1$H NMR (270 MHz, $CDCl_3$) δ 7.39–7.24(5H, m), 5.31–5.28(0.35H, m), 5.28–5.22(0.15H, m), 5.12–5.07 (0.35H, m), 5.06–5.01(0.15H, m), 4.73–4.68(0.7H, m), 3.88–3.79(0.7H, m), 3.54–3.50(0.3H, m), 3.13–2.44(5.3H, m), 2.20–1.93(2H, m).

Preparation 35
(S)-1-Benzyl-3-chloropyrrolidine
To a stirred solution of (R)-1-benzyl-3-pyrrolidinol (886 mg, 5.0 mmol) in $CCl_4$ (20 ml) was added triphenylphosphine (1.574 g, 6.0 mmol) at rt. After 20 h stirring at reflux temperature, the solvent was evaporated. Saturated $NaHCO_3$ aqueous solution and water was added to the residue, and the mixture was extracted with AcOEt. The extract was brine, dried ($Na_2SO_4$), and concentrated to give brown oil, which was purified by column chromatography (silica gel; 100 g, $CH_2Cl_2$/MeOH: 50/1–45/1) to give 706 mg (72%) of pale yellow oil.
$^1$H NMR (270 MHz, $CDCl_3$) δ 7.33–7.23(5H, m), 4.42–4.33(1H, m), 3.73–3.61(2H, m), 3.09(1H dd, J=6.6, 10.6 Hz), 2.81–2.61(3H, m), 2.48–2.35(1H, m), 2.13–2.03 (1H, m).

Preparation 36
2-(3-(S)-Chloropyrrolidin-1-yl)-1-(S)-phenylethanol and 2-(3-(S)-Chloropyrrolidin-1-yl)-2-(R)-phenylethanol
To a stirred solution of (S)-1-benzyl-3-chloropyrrolidine (695 mg, 3.55 mmol) in dichloroethane (10 ml) was added 1-chloroethyl chloroformate (0.38 ml, 3.55 mmol) at 0° C. The mixture was stirred at 0° C. for 10 min and refluxed for 1.5 h. After cooling down to rt, the solvent was evaporated. The residue was dissolved in MeOH (5 ml) and refluxed for 1 h. After cooling down to rt, the solvent was evaporated to give 787 mg of brown solid.
Title compounds were prepared from the above solid and (S)-(−)-styreneoxide in 39% over all yield as 0.67 to 0.33 mixture of the title compounds according to the procedures similar to those described in Preparation 2.
$^1$H NMR (270 MHz, $CDCl_3$) δ 7.39–7.27(5H, m), 4.70 (0.67H, dd, J=3.3, 10.3 Hz), 4.45–4.40(0.67H, m), 4.38–4.32(0.33H, m), 3.91–3.02(2.33H, m), 2.88–2.56(4H, m), 2.50–2.31(1H, m), 2.17–2.03(1H, m).

Preparation 37
Methlyl 3-fluoro-4-nitrobenzoate

A mixture of 3-fluoro-4-nitrobenzoic acid (2.07 g, 11.2 mmol) and c$H_2SO_4$ (0.5 ml) in MeOH (10 ml) was refluxed for 8 h. The solvent was evaporated. The residue was dissolved in AcOEt and washed with saturated $NaHCO_3$ aqueous solution, water, brine, dried ($Na_2SO_4$), and concentrrated to give 2.14 g (96%) of ivory solid.

$^1$H NMR (270 MHz, $CDCl_3$) δ 8.15–8.07(1H, m), 7.99–7.96(1H, m), 7.95–7.92(1H, m), 3.99(3H, S).

Preparation 38
Methlyl 4-amino-3-fluorobenzoate

A mixture of methlyl 3-fluoro-4-nitrobenzoate (2.14 g, 10.8 mmol) and iron powder (2.63 g) in acetic acid (22 ml) was stirred at 50° C. for 2.5 h. After cooling down to room temperature, $CH_2Cl_2$ (100 ml) and water (300 ml) was added to the mixture and filtered to remove iron powder. The organic layer was separated and the aqueous layer was extracted with $CH_2Cl_2$ (70 ml×2). The $CH_2Cl_2$ solution was combined, washed with water, brine, dried ($Na_2SO_4$), and concentrated to give 1.77 g (97%) of pale brown solid.

$^1$H NMR (270 MHz, $CDCl_3$) δ 7.70–7.62(2H, m), 6.79–6.70(1H, m). 4.13(2H, br. s), 3.86(3H, S).

Preparation 39
Methlyl 3-fluoro-4-methylaminobenzoate

To a solution of methlyl 4-amino-3-fluorobenzoate (1.77 g, 10.5 mmol) in $CH_2Cl_2$ (50 ml) was added $Na_2CO_3$ (3.33 g, 31.4 mmol) and trifluoroacetic anhydride (2.96 ml, 20.9 mmol) at room temperature. After stirring for 2.5 h, the solid was filtered off. The filtrate was washed with water, brine, dried ($Na_2SO_4$); and concentrated to give 2.70 g (97%) of white solid. To a solution of this solid (2.70 g, 10.2 mmol) in DMF (48 ml) was added $Na_2CO_3$ (16.9 g, 160 mmol) and iodomethane (20.8 ml, 334 mmol) at 0° C. After stirring for 2 h at 0° C., for 1 h at room temperature, the mixture was poured into 2NHCl with ice and extracted with AcOEt: toluene=2:1(200 ml×2). The extract was washed with water, brine, dried ($Na_2SO_4$), and concentrated to give 3.06 g (quant) of brown oil. This oil was dissolved in MeOH (25 ml) and 7% $K_2CO_3$ solution (12.5 ml) was added at 0° C. After stirring for 2 h at 0° C., for 4 h at room temperature, 7% $K_2CO_3$ solution (12.5 ml) was added. After stirring for 1.5 h at room temperature, the mixture was acidified with 5NHCl and MeOH was evapolated. The residue was extracted with AcOEt. The extract was washed with water, brine, dried ($Na_2SO_4$), and concentrated to give 1.83 g (98%) of pale brown solid.

$^1$H NMR (270 MHz, $CDCl_3$) δ 7.90–7.72(1H, m), 7.62 (1H, dd, J=1.8, 12.5 Hz), 6.63(1H, t, J=8.6 Hz), 4.40(1H, br. s), 3.86(3H, S), 2.94(3H, d, J=5.1 Hz).

Preparation 40
5-[N-(tert-Butoxycarbonyl)-N-methylamino]-N'-propylpicolinamide To a solution of 5-[N-(tert-butoxycarbonyl)-N-methylamino]picolinic acid (1.93 g, 7.66 mmol) and triethylamine (1.60 ml, 11.5 mmol) in DMF (0.678 ml) and $CH_2Cl_2$ (14 ml) was added oxalyl chloride (0.989 ml, 11.3 mmol) dropwise at room temperature. After stirring for 30 min at room temperature, the solvent was evapolated The residue was dissolved in $CH_2Cl_2$ (14 ml). This solution was added dropwise to a stirried, cooled solution of n-propylamine (0.756 ml, 9.19 mmol) and triethylamine (3.20 ml, 23.0 mmol) in $CH_2Cl_2$ (28 ml) while the temperature was kept below 15° C. After stirring for 15 h at room temperature, the mixture was washed with water, brine, dried ($Na_2SO_4$), and concentrated to give brown oil, which was purified by column chromatography (silica gel, 100 g, $CH_2Cl_2$/MeOH: 60/1) to give 1.82 g (81%) of pale brown oil.

$^1$H NMR (270 MHz, $CDCl_3$) δ 8.49(1H, d, J=2.6 Hz), 8.16(1H, d, J=8.4 Hz), 7.95(1H, br. s), 7.71(1H, dd, J=2.6, 8.4 Hz), 3.50–3.40(2H, m), 3.32(3H, S), 1.75–1.55(2H, m), 1.48(9H, s), 1.00(3H, t, J=7.3 Hz).

Preparation 41
5-N-Methylamino-N'-propylpicolinamide

A solution of 5-[N-(tert-butoxycarbonyl)-N-methylamino]-N'-propylpicolinamide (1.82 g, 6.21 mmol) in trifluoroacetic acid (30 ml) was stirred at 0° C. for 2 h. After removal of the solvent, the residue was dissolved in $CH_2Cl_2$ and 25% ammonia solution. The organic layer was separated and washed with brine, dried ($Na_2SO_4$), and concentrated to give 1.20 g (100%) of brown solid.

$^1$H NMR (270 MHz, $CDCl_3$) δ 8.01(1H, d, J=8.4 Hz), 7.88(1H d, J=2.9 Hz), 7.78(1H, br. s), 6.90(1H dd, J=2.9, 8.4 Hz), 4.17(1H, br. s), 3.45–3.35(2H, m), 2.91(3H, d, J=5.1 Hz), 1.75–1.55(2H, m), 0.98(3H, t, J=7.3 Hz).

Preparation 42
4-N-Hydroxyamino-N'-propylbenzamide

To a solution of 4-nitro-N-propylbenzamide (2.75 g, 13.2 mmol) and ammonium chloride (812 mg, 15.2 mmol) in EtOH (20 ml) and water (10 ml) was added zinc powder (1.70 g, 26.0 mmol) portionwise with water cooling. After stirring for 30 min at room temperature, zinc powder (0.50 g, 7.65 mmol) was added to the mixture and stirred for 30 min at room temperature. The solid was removed through celite and washed with MeOH. The filtrate and washings were combined and concentrated to give yellow solid, which was purified by column chromatography (silica gel, 130 g, $CH_2Cl_2$/MeOH: 25/1–10/1) to give 2.06 g (80%) of ivory solid.

$^1$H NMR (270 Hz, $CDCl_3$-DMSO-$d_6$) δ 8.32(1H, d, J=2.2 Hz), 7.72(2H, d, J=8.4 Hz), 7.25–7.10(1H, m), 6.95(2H, d, J=8.8 Hz), 3.45–3.30(2H, m), 2.91(1H, s), 1.70–1.55(2H, m), 0.96(3H, t, J=7.3 Hz).

Preparation 43
4-Amino-2-chloro-N'-propylbenzamide

A mixture of 4-amino-2-chlorobenzoic acid (3.00 g, 17.5 mmol), n-propylamine (2.88 ml, 35.0 mmol) and WSC (6.71 g, 35.0 mmol) in $CH_2Cl_2$ (35 ml) was stirred at room temperature for 16 h. The mixture was washed with water, brine, dried ($Na_2SO_4$), and concentrated to give brown oil, which was purified by column chromatography (silica gel; 180 g, $CH_2Cl_2$/MeOH: 30/1–10/1) to give 2.32 g (62%) of pale ivory solid.

$^1$H NMR (270 MHz, $CDCl_3$) δ 7.64(1H, d, J=8.4 Hz), 6.64(1H, d, J=2.6 Hz), 6.57(1H, dd, J=2.6, 8.4 Hz), 6.44(1H, br. s), 3.97(2H, br. s), 3.50–3.30(2H, m), 1.75–1.55(2H, m), 0.99(3H, t, J=7.3 Hz).

Preparation 44
2-Chloro-4-methyamino-N'-propylbenzamide

A mixture of 4-amino-2-chloro-N'-propylbenzamide (2.32 g, 10.9 mmol), iodomethane (0.68 ml, 10.9 mmol) and $K_2CO_3$ (1.51 g, 10.9 mmol) in DMF (50 ml) was stirred at room temperature for 20 h. Water was added to the mixture and extracted with AcOEt:toluene=1:1. The extract was washed with water, brine, dried ($Na_2SO_4$), and concentrated to give pale brown solid, which was purified by column chromatography (silica gel; 120 g, $CH_2Cl_2$/MeOH: 40/1) to give 887 mg (36%) of pale brown solid.

$^1$H NMR (270 MHz, $CDCl_3$) δ 7.57(1H, d, J=8.4 Hz), 6.80(1H br. s), 6.53(1H, d, J=2.2 Hz), 6.50(1H, dd, J=2.2, 8.4 Hz), 5.00–4.80(1H, m), 3.45–3.30(2H, m), 2.82(3H, d, J=5.1 Hz), 1.75–1.55(2H, m), 0.99(3H, t, J=7.3 Hz).

Preparation 45
4-Methylamino-N'-(2-(S)-hydroxypropyl)benzamide

This was prepared from 4-(methylamino)benzoic acid and (S)-(+)-1-amino-2-propanol in 22% yield according to the procedures similar to those described in Preparation 43.
$^1$H NMR (270 MHz, CDCl$_3$-DMSO-d$_6$) δ 7.69(2H, d, J=8.4 Hz), 7.14(1H, br. s), 6.56(2H, d, J=8.8 Hz), 4.60–4.30 (2H, m), 3.98–3.94(1H, m), 3.64–3.55(1H, m), 3.28–3.18 (1H, m), 2.85(3H, s), 1.20(3H, d, J=6.2 Hz).

Preparation 46
4-Methylamino-N'-(2-(R)-hydroxypropyl)benzamide

This was prepared from 4-(methylamino)benzoic acid and (R)-(-)-1-amino-2-propanol in 41% yield according to the procedures similar to those described in Preparation 43.
$^1$H NMR (270 MHz, CDCl$_3$-DMSO-d$_6$) δ 7.68(2H, dd, J=1.8, 7.0 Hz), 7.12(1H, br. s), 6.55(2H, dd, J=1.8, 7.0 Hz), 4.50(1H, br. s), 4.37(1H, br. s), 3.98–3.93(1H, m), 3.64–3.55 (1H, m), 3.28–3.18(1H, m), 2.85(3H, d, J=4.8 Hz), 1.20(3H, d, J=6.2 Hz).

Preparation 47
4-Methylamino-N'-propylbenzamide

This was prepared from 4-(methylamino)benzoic acid and n-propylamine in 82% yield according to the procedures similar to those described in Preparation 43.
$^1$H NMR (270 MHz, CDCl$_3$) δ 7.63(2H, d, J=8.8 Hz), 6.56(2H, d, J=8.8 Hz), 6.05(1H, br. s), 4.11(1H, br. s), 3.45–3.30(2H, m), 2.86(1H, s), 1.70–1.50(2H, m), 0.97(3H, t, J=7.3 Hz).

Preparation 48
4-[N(Benzyloxycarbonyl)-N-methylamino]-N'-(2,2,3,3,3,-pentafluoropropyl)benzamide To a solution of 4-[N-(benzyloxycarbonyl)-N-methylamino]benzoic acid (100 mg, 0.351 mmol) in CH$_2$Cl$_2$ (1 ml) was added oxalyl chloride (0.122 ml, 140 mmol) and DMF (0.026 ml) at room temperature. After stirring for 4 h at room temperature the solvent was evapolated. The residue was dissolved in CH$_2$Cl$_2$ (10 ml). To this solution was added 2,2,3,3,3-pentarluoropropylamine (523 mg, 3.51 mmol) and triethylarmine (0.372 ml, 2.67 mmol) at room temperature. After stirring for 18 h at room temperature, saturated NaHCO$_3$ aqueous solution was added to the mixture and extracted with CH$_2$Cl$_2$. The extract was washed with brine, dried (Na$_2$SO$_4$), and concentrated to give brown oil, which was purified by column chromatography (silica gel; 30 g, CH$_2$Cl$_2$ only-CH$_2$Cl$_2$/MeOH: 50/1) to give 532 mg (72%) of title compound.
$^1$H NMR (270 MHz, CDCl$_3$) δ 7.75(2H, d, J=8.8 Hz), 7.39–7.31(7H, m), 6.42–6.31(1H, m), 5.19(2H, s), 4.17(2H, ddd, J=6.2, 14.7, 14.7 Hz), 3.36(3H, s).

Preparation 49
4-[N-(Benzyloxycarbonyl)-N-methylamino]-N'-tert-amylbenzamide

This was prepared from 4-[N-(benzyloxycarbonyl)-N-methylamino]benzoic acid and tert-amylanine in 22% yield according to the procedures similar to those described in Preparation 48.
$^1$H NMR (270 MHz, CDCl$_3$) δ 7.69 (2H, d, J=8.4 Hz), 7.32–7.29 (7H, m), 5.86–5.75 (1H, m), 5.17(2H, s), 3.33 (3H, s), 1.88–1.80(2H, m), 1.40(6H, s), 0.89(3H, t, J=7.3 Hz).

Preparation 50
4-[N-(Benzyloxycarbonyl)-N-methylamino]-N'-tert-butylbenzamide

This was prepared from 4-[N-(benoxycarbonyl)-N-methyamino]benzoic acid and tert-butylamine in 93% yield according to the procedures similar to those described in Preparation 48.
$^1$H NMR (270 MHz, CDCl$_3$) δ 7.69 (2H, d, J=8.8 Hz), 7.32–7.29 (7H m), 5.89 (1H, br. s), 5.17(2H, s), 3.33(3H, s), 1.46(9H, s).

Preparation 51
4-Methylamino-N'-(2,2,3,3,3,-pentafluoropropyl)benzamide

A suspension mixture of 4-[N-(benzyloxycarbonyl)-N-methylamino]-N'-(2,2,3,3,3,-pentafluoropropyl)benzamide (532 mg, 1.28 mmol) and 10% palladium carbon (41 mg) in MeOH (5 ml) was stirred under hydrogen atmosphere at room temperature for 6 h. The catalyst was removed through Celite and washed with MeOH. The filtrate and washings were combined and concentrated to give 345 mg (96%) of title compound.
$^1$H NMR (270 MHz, CDCl$_3$) δ 7.66 (2H, d, J=8.4 Hz), 6.58 (2H, d, J=8.4 Hz), 6.15–6.12(1H, m), 4.23–4.09(3H, m), 2.89(3H, d, J=4.4 Hz).

Preparation 52
4-Methylamino-N'-tert-amylbenzamide

This was prepared from 4-[N-(benzyloxycarbonyl)-N-methylamino]-N'-tert-amylbenzamide in 88% yield according to the procedures similar to those described in Preparation 51.
$^1$H NMR (270 MHz, CDCl$_3$) δ 7.58(2H, d, J=8.4 Hz), 6.56(2H, d, J=8.8 Hz), 5.78(1H, br. s), 4.00(1H, br. s), 2.87(3H, s), 1.83(2H, q, J=7.7 Hz), 1.39(6H, s), 0.89(3H, t, J=7.7 Hz).

Preparation 53
4-Methylamino-N'-tert-butylbenzamide

This was prepared from 4-[N-(benzyloxycarbonyl)-N-methylamino]-N'-tert-butylbenzamide in 100% yield according to the procedures similar to those described in Preparation 51.
$^1$H NMR (270 MHz, CDCl$_3$) δ 7.58(2H, d, J=8.4 Hz), 6.56(2H, d, J=8.8 Hz), 5.78(1H, br. s), 2.86(3H, s), 1.45(9H, s).

Example 1

Preparation of 4-{N-[2-(3-(S)-Methoxymethoxypyrrolidin-1-yl)-1-(S)-phenylethyl]-N-methylamio}-N'-propylbenzamide (i) Methyl 4-{N-[2-(3-(S)-methoxymethoxypyrrolidin-1-yl)-1-(S)-phenylethyl]-N-methylamino}benzoate To a stirred solution of the mixture of 2-(3-(S)-methoxymethoxypyrrolidin-1-yl)-1-(S)-phenylethanol and 2-(3-(S)-methoxymethoxypyrrolidin-1-yl)-2-(R)-phenylethanol (2.01 g, 8.00 mmol) and triethylanuine (1.34 ml, 9.60 mmol) in CH$_2$Cl$_2$ (35 ml) was added methanesulfonyl chloride (0.744 ml, 9.60 mmol) dropwise at 0° C. (ice bath). After 5.5 h stirring at room temperature, the reaction mixture was washed with saturated NaHCO$_3$ aqueous solution, brine, dried (Na$_2$SO$_4$), and concentrated to give 2.16 g of brown viscous oil. To this oil was added Methyl 4-methylaminobenzoate (1.45 g, 8.80 mmol) and ethanol (16 ml) and the mixture was stirred at reflux temperature for 1.5 h. The solvent was evaporated. The residue was dissolved in CH$_2$Cl$_2$ and washed with saturated NaHCO$_3$ aqueous solution and brine, dried (Na$_2$SO$_4$), and concentrated to give brown oil, which was purified by column chromato-graphy (silica gel 150 g, CH$_2$Cl$_2$/MeOH: 100/1–35/1) to afford 1.99 g (62.5%) of brown oil.

¹H NMR (270 MHz, CDCl₃) δ 7.89 (2H, d, J=9.2 Hz), 7.35–7.20 (5H, m), 6.78 (2H, d, J=9.2 Hz), 5.17 (1H, dd, J=6.6, 8.1 Hz), 4.59 (1H, d, J=7.0 Hz), 4.55 (1H, d, J=7.0 Hz), 422–4.12 (1H, m), 3.85 (3H, s), 3.30 (3H, s), 3.10 (1H, dd, J=6.2, 12.8 Hz), 3.03 (1H, dd, J=8.4, 12.8 Hz), 2.86 (3H, s), 2.85–2.80 (1H, m), 2.77–2.67 (1H, m), 2.65-2.53(2H, m), 2.05 (1H, ddd, J=7.5, 13.9, 13.9 Hz), 1.83–1.70(1H, m).

(ii) 4-{N-[2-(3-(S)-Methoxymethoxypyrrolidin-1-yl)-1-(S)-phenylethyl]-N-methylamino}benzoic Acid A mixture of methyl 4-{N-[2-(3-(S)-methoxymethoxypyrrolidin-1-yl)-1-(S)-phenylethyl]-N-methylamino}benzoate (1.99 g, 5.00 mmol) and 4N-NaOH (12.5 ml. 50.0 mmol) in MeOH (35 ml) was stirred at 75° C. for 3 h. The mixture was neutrallized with 5N-HCl at 0° C. The solvent was removed in vacuo. CH₂Cl₂ was added to the residue and insoluble solid was removed by filtration. The filtrate was concentrated to give 2.04 g (quant) of pale brown amorphous.

¹H NMR (270 MHz, CDCl₃) δ 7.93 (2H, d, J=8.8 Hz), 7.40–7.10 (5H, m), 6.81 (2H, d, J=9.2 Hz), 5.85 (1H, br. s), 5.26 (1H, dd, J=6.2, 8.1 Hz), 4.60 (1H, d, J=7.0 Hz), 4.56 (1H, d, J=7.0 Hz), 4.25–4.15 (1H, m), 3.30 (3H, s), 3.20–3.05 (2H m), 2.97 (1H, dd, J=6.2, 9.9 Hz), 2.87 (3H, s), 2.80–2.65 (3H, m), 2.15–2.00 (1H, m), 1.90–1.75 (1H, m).

(iii) 4-{N-[2-(3-(S)-Methoxymethoxypyrrolidin-1-yl)-1-(S)-phenylethyl]-N-methylamino}-N'-propylbenzamide To a stirred solution of 4-{N-[2-(3-(S)-methoxymethoxypyrrolidin-1-yl)-1-(S)-phenylethyl]-N-methylamino}benzoic acid (2.04 g, 5.00 mmol) and n-propylamine (0.822 ml, 10.0 mmol) in CH₂Cl₂ (35 ml) was added 1-ethyl-3-(3-dimethylaminopropyl)carbodiimide hydrochloride (1.92 g, 10 mmol) at room temperature. After 15.5 hr stirring, the reaction mixture was washed with water and brine. dried (Na₂SO₄), and concentrated to give brown oil, which was purified by column chromatography (silica gel; 100 g, CH₂Cl₂/MeOH: 25/1) to give 1.52 g (72%) of pale brown amorphous.

¹H NMR (270 MHz, CDCl₃) δ 7.65 (2H, d, J=8.8 Hz), 7.35–7.20 (5H m), 6.79 (2H, d, J=9.2 Hz), 6.05–5.90 (1H, m), 5.14 (1H, dd, J=6.6, 8.1 Hz), 4.59 (1H, d, J=7.0 Hz), 4.55 (1H, d, J=7.0 Hz), 4.24–4.10 (1H, m), 3.39 (2H, dd, J=6.6, 13.9 Hz), 3.30 (3H, s), 3.14–2.96 (2H, m), 2.90–2.80 (1H, m), 2.85 (3H, s), 2.78–2.52 (3H, m), 2.14–1.96 (1H, m), 1.84–1.70 (1H, m), 1.68–1.56 (2H, m), 0.97 (3H, t, J=7.3 Hz).

Example 2

Preparation of 4-{N-[2-(3-(S)-Hydroxypyrrolidin-1-yl)-1-(S)-phenylethyl]-N-methylamino}-N'-propylbenzamide A mixture of 4-{N-[2-(3-(S)-methoxymethoxypyrrolidin-1-yl)-1-(S)-phenylethyl]-N-methylamino}-N'-propylbenzamide (1.52 g, 3.58 mmol) and 10% HCl in MeOH (25 ml) was stirred at room temperature for 6 h. The solvent was evaporated. The residue was basified with 25% ammonium hydroxide, extracted with CH₂Cl₂. The extract was washed with brine, dried (Na₂SO₄) and concentrated to give pale brown amorphous, which was purified by column chromatography (silica gel, 65 g, CH₂Cl₂/MeOH: 20/1–15/1) to give 1.21 g (89%) of pale brown amorphous.

¹H NMR (270 MHz, free amine, CDCl₃) δ 7.66 (2H, d, J=9.2 Hz), 7.40–7.20 (5H, m), 6.81 (2H, d, J=9.2 Hz), 6.05–5.90 (1H, m), 5.15 (1H, dd, J=5.9, 9.2 Hz), 4.28–4.16 (1H, m), 3.46–3.32 (2H, m), 3.13 (1H, dd, J=9.2, 12.8 Hz), 3.03 (1H, dd, J=5.9. 12.8 Hz), 2.90 (1H, ddd, J=5.0, 8.5, 8.5 Hz), 2.84 (3H, s), 2.73 (1H, d, J=9.9 Hz), 2.56 (1H, dd, J=4.6, 9.7 Hz), 2.32 (1H, ddd, J=6.1, 9.0, 9.0 Hz), 2.18–2.00 (1H, m), 1.90–1.50 (4H, m), 0.98 (3H, t, J=7.3 Hz).

600 mg of this amorphous was dissolved in 10% HCl in MeOH (10 ml). The solvent was concentrated to give 625 mg of HCl salt as pale brown amorphous.

IR(KBr): 3300, 1610 cm⁻¹. MS m/z: 382(M+H)⁺; Anal. Calcd for C₂₃H₃₁N₃O₂.HCl.1.5H₂O: C, 62.08; H, 7.93; N, 9.44. Found: C, 62.29; H, 8.01; N, 9.42.

Example 3

Preparation of 4-{N-[2-(3-(S)-Methoxymethoxypyrrolidin-1-yl)-1-(S)-phenylethyl]-N-methylamino}-N'-methylbenzamiide This was prepared from 4-{N-[2-(3-(S)-methoxymethoxypyrrolidin-1-yl)-1-(S)-phenylethyl]-N-methylamino}benzoic acid and methylamine hydrochloride in 26% yield according to a procedure stnuar to that described in Example 1 (iii).

¹H NMR (270 MHz, CDCl₃) δ 7.64 (2H, d, J=8.8 Hz), 7.40–7.20 (5H, m), 6.79(2H, d, J=8.8 Hz), 6.02 (1H, br. s), 5.13 (1H, dd, J=6.6, 8.1 Hz), 4.59 (1H, d, J=7.0 Hz), 4.55 (1H, d, J=6.6 Hz), 4.20–4.13 (1H, m), 3.30 (3H, s), 3.15–3.00 (2H, m), 2.97 (3H, d, J=5.1 Hz), 2.90–2.80 (1H, m), 2.83 (3H, s), 2.75–2.55 (3H, m), 2.05 (1H, ddd, J=7.7, 14.3, 13.9 Hz), 1.90–1.70 (1H, m).

Example 4

Preparation of 4-{N-[2-(3-(S)-Hydroxypyrrolidin-1-yl)-1-(S)-phenylethyl]-N-methylamino}-N'-methylbenzamide This was prepared from 4-{N-[2-(3-(S)-methoxymethoxypyrrolidin-1-yl)-1-(S)-phenylethyl]-N-methylamino}-N'-methylbenzamide in 82% yield according to a procedure similar to that described in Example 2.

¹H NMR (270 MHz, free amine, CDCl₃) δ 7.66 (2H, d, J=9.2 Hz), 7.40–7.20 (5H, m), 6.81 (2H, d, J=8.8 Hz), 6.00–5.95 (1H, m), 5.15 (1H, dd, J=6.0, 9.0 Hz), 4.25–4.20 (1H, m), 3.13 (1H, dd, J=9.2, 12.8 Hz), 3.03 (1H, dd, J=5.9, 12.8 Hz), 2.98 (3H, d, J=5.1 Hz), 2.95–2.80 (1H, m), 2.83 (3H s), 2.74 (1H, d, J=9.9 Hz), 2.55 (1H, dd, J=4.6, 9.7 Hz), 2.35–2.25 (1H, m), 2.17–2.05 (1H, m), 1.80–1.60 (2H, m); HCl salt: amorphous solid. IR(KBr): 3350, 1610 cm⁻¹. Anal. Calcd for C₂₁H₂₇N₃O₂.HCl.1.2H₂O: C, 61.29; H, 7.45; N, 10.21; Found: C,61.68; H, 7.84; N,10.20.

Example 5

Preparation of 4-{N-[2-(3-(S)-Methoxymethoxypyrrolidin-1-yl)-1-(S)-phenylethyl]-N-methylamino}-N'-ethylbenzamide This was prepared from 4-{N-[2-(3-(S)-methoxymethoxypyrrolidin-1-yl)-1-(S)-phenylethyl]-N-methylamino}benzoic acid and ethylamine hydrochloride in 33% yield according to a procedure similar to that described in Example 1 (iii).

¹H NMR (270 MHz, CDCl₃) δ 7.64 (2H, d, J=8.8 Hz), 7.34–7.24 (5H, m), 6.79 (2H, d, J=8.8 Hz), 5.95–5.83 (1H, m), 5.13 (1H, dd, J=7.0, 7.5 Hz), 4.59 (1H d, J=7.0 Hz), 4.55 (1H, d, J=6.6 Hz), 4.25–4.14 (1H, m), 3.52–3.42 (2H, m), 3.30 (3H, s), 3.10–3.01 (2H, m), 2.89–2.80 (1H, m), 2.83 (3H, s), 2.75–2.53 (3H, m), 2.11–2.01 (1H, m), 1.80–1.74 (1H, m), 1.23 (3H, t, J=7.1 Hz).

Example 6

Preparation of 4-{N-[2-(3-(S)-Hydyroxypyrrolidin-1-yl)-1-(S)-phenylethyl]-N-methylamino}-N'-ethylbenzamide This was prepared from 4-{N-[2-(3-(S)-methoxymethoxypyrrolidin-1-yl)-1-(S)-phenylethyl]-N-methylamino}-N'-ethylbenzamide in 43% yield according to a procedure similar to that described in Example 2.

$^1$H NMR (270 MHz, free amine, CDCl$_3$) δ 7.65 (2H, d, J=8.8 Hz), 7.34–7.23 (5H, m), 6.80 (2H, d, J=8.8 Hz), 6.01 (1H, br.s), 5.14 (1H, dd, J=6.2, 8.8 Hz), 4.22–4.18 (1H, m), 3.50–3.40 (2H, m), 3.11 (1H, dd, J=8.8, 12.8 Hz), 3.02 (1H, dd, J=5.9, 12.8 Hz), 2.92–2.85 (1H, m), 2.82 (3H, s), 2.70 (1H, d, J=9.5 Hz), 2.57 (1H, dd, J=4.8, 9.9 Hz), 2.37–2.29 (1H, m), 2.12–2.01 (2H, m), 1.68–1.60 (1H,m), 1.21 (3H, t, J=7.3 Hz).

HCl salt: amorphous solid. IR(KBr): 3350, 1610 cm$^{-1}$. Anal. Calcd for C$_{22}$H$_{29}$N$_3$O$_2$.HCl.4H$_2$O C, 55.72; H, 7.70; N, 8.97; Found: C, 55.51; H, 8.05; N, 8.83.

Example 7

Preparation of 4-{N-[2-(3-(S)-Methoxmethoxypyrrolidin-1-yl)-1-(S)-phenylethyl]-N-methylamino)}-N'-butylbenzamide This was prepared from 4-{N-[2-(3-(S)-methoxymethoxypyrrolidin-1-yl)-1-(S)-phenylethyl]-N-methylamino}benzoic acid and n-butylamine in 40% yield according to a procedure similar to that described in Example 1 (iii).

$^1$H NMR (270 MHz, CDCl$_3$) δ 7.63 (2H, d, J=9.2 Hz), 7.34–7.24 (5H, m), 6.79 (2H, d, J=9.2 Hz), 6.00–5.85 (1H, m), 5.12 (1H, dd, J=6.6, 7.1 Hz), 4.59 (1H, d, J=6.6 Hz), 4.55 (1H d, J=6.6 Hz), 4.19–4.15 (1H, m), 3.50–3.40 (2H, m), 3.29 (3H, s), 3.07–3.02 (2H, m), 2.90–2.80 (1H, m), 2.84 (3H s), 2.72–2.57 (3H, m), 2.08–2.01 (1H, m), 1.78–1.60 (1H, m), 1.58–1.36 (4H, m), 0.94 (3H, t, J=7.3 Hz)

Example 8

Preparation of 4-{N-[2-(3-(S)-Hydroxypyrrolidin-1-yl)-1-(S)-phenylethyl]-N-methylamino}-N'-butylbenzamide This was prepared from 4-{N-[2-(3-(S)-methoxymethoxypyrrolidin-1-yl)-1-(S)-phenylethyl]-N-methylamino}-N'-butylbenzamide in 59% yield according to a procedure similar to that described in Example 2.

$^1$H NMR (270 MHz, free amine, CDCl$_3$) δ 7.65 (2H, d, J=8.8 Hz), 7.35–7.24 (5H, m), 6.80 (2H, d, J=8.8 Hz), 5.82–5.78 (1H, m), 5.15 (1H, dd, J=5.9, 8.8 Hz), 4.26–4.24 (1H,m), 3.43 (2H, dd, J=7.0, 12.8 Hz), 3.13 (1H, dd, J=8.8, 12.8 Hz), 3.03 (1H, dd, J=6.2, 12.8 Hz), 2.93–2.85 (1H, m), 2.84 (3H, s), 2.73 (1H, d, J=9.5 Hz), 2.56 (1H, dd, J=4.8, 9.5 Hz), 2.37–2.28 (1H, m), 2.10–2.06 (1H, m), 1.72–1.52 (4H, m), 1.47–1.25 (2H, m), 0.95 (3H, t, J=7.3 Hz); HCl salt: amorphous solid. IR(KBr): 3350, 1610 cm$^{-1}$. MS m/z: 396(M+H)$^+$. Anal. Calcd for C$_{24}$H$_{33}$N$_3$O$_2$.HCl.1.4H$_2$O: C, 63.05; 8.11; N, 9.19; Found: C, 63.06; H, 8.04; N, 8.98.

Example 9

Preparation of 4-{N-[1-(S)-Phenyl-2-(3-(S)-tetrahydropyran-2-yloxypyrrolidin-1-yl)-ethyl]-N-methylamino}-N'-pentylbenzamide This was prepared from 2-(R)-phenyl-2-(3-(S)-tetrahydropyran-2-yloxypyrrolidin-1-yl)ethanol and 1-(S)-phenyl-2-(3-(S)-tetrahydropyran-2-yloxypyrrolidin-1-yl)ethanol in 33% over all yield according to a procedure similar to that described in Example 1 (i)–(iii).

$^1$H NMR (270 MHz, CDCl$_3$) δ 7.70–7.60 (2H, m), 7.40–7.20 (5H, m), 6.79 (2H, d, J=8.8 Hz), 6.00–5.90 (1H, m), 5.20–5.10 (1H, m), 4.60–4.55 (0.6H, m), 4.50–4.40 (0.4H, m), 4.35–4.20 (1H, m), 3.90–3.72 (1H, m), 3.50–3.35 (3H, m), 3.15–2.90 (3H, m), 2.84 (1.8H, s), 2.83 (1.2H, s), 2.80–2.50 (3H, m), 2.20–1.95 (1H, m), 1.90–1.25 (13H,m), 0.91 (3H, t, J=7.0 Hz).

Example 10

Preparation of 4-{N-[2-(3-(S)-Hydroxyprrolidin-1-yl)-1-(S)-phenylethyl]-N-methylamino}-N'-pentylbenzamide This was prepared from 4-{N-[1-(S)-phenyl-2-(3-(S)-tetrahydropyran-2-yloxypyrrolidin-1-yl)ethyl]-N-methylamino}-N'-pentylbenzamide in 98% yield according to a procedure similar to that described in Example 2.

$^1$H NMR (270 MHz, free amine, CDCl$_3$) δ 7.65 (2H, d, J=9.2 Hz), 7.40–7.20 (5H, m), 6.81 (2H, d, J=8.8 Hz), 6.00–5.90 (1H, m), 5.16 (1H, dd, J=6.0, 9.0 Hz), 4.26–4.18 (1H,m), 3.50–3.37 (2H, m), 3.13 (1H, dd, J=9.2, 12.8 Hz), 3.03 (1H, dd, 6.3, 12.8 Hz). 2.93–2.80 (1H, m), 2.84 (3H, s), 2.73 (1H, d, J=9.2 Hz), 2.56 (1H, dd, J=4.8, 9.5 Hz), 2.37–2.28 (1H, m), 2.17–2.00 (1H, m), 1.90–1.55 (4H, m), 1.50–1.30 (4H, m), 0.93 (3H, t, J=7.3 Hz); HCl salt: amorphous solid. IR(KBr): 3350, 1610 cm$^{-1}$. Anal. Calcd for C$_{25}$H$_{35}$N$_3$O$_2$.HCl.0.25 H$_2$O: C, 66.65; H, 8.17; N, 9.33; Found: C, 66.57; H, 8.47; N,9.31.

Example 11

Preparation of 4-{N-[2-(3-(S)-Methoxymethoxypyrrolidin-1-yl-1-(S)-phenylethyl]-N-methylamino}-N'-isopropylbenzamide This was prepared from 4-{N-[2-(3-(S)-methoxymethoxypyrrolidin-1-yl)-1-(S)-phenylethyl]-N-methylamino}benzoic acid and isopropylamine in 15% yield according to a procedure sinilar to thaL described in Example 1 (iii).

$^1$H NMR (270 MHz, CDCl$_3$) δ 7.63 (2H, d, J=9.2 Hz), 7.34–7.21 (5H, m), 6.78 (2H, d, J=9.6 Hz), 5.75–5.72 (1H, m), 5.12 (1H, dd, J=6.2, 8.8 Hz), 4.59 (1H, d, J=6.6 Hz), 4.55 (1H, d, J=6.6 Hz), 4.30–4.23 (1H, m), 4.18–4.14 (1H, m), 3.30 (3H, s), 3.06–3.03 (2H, m), 2.90–2.80 (1H, m), 2.85 (3H, s), 2.81–2.72 (1H, m), 2.66–2.57 (2H, m), 2.08–2.01 (1H, m), 1.79–1.76 (1H, m), 1.23 (6H, d, J=6.6 Hz).

Example 12

Preparation of 4-{N-[2-(3-(S)-Hydroxypyrrolidin-1-yl)-(S)-phenylethyl]-N-methylamino}-N'-isopropylbenzamide This was prepared from 4-{N-[2-(3-(S)-methoxymethoxypyrrolidin-1-yl)-1-(S)-phenylethyl]-N-methylamino}-N'-isopropylbenzamide in 80% yield according to a procedure similar to that described in Example 2.

$^1$H NMR (270 MHz, free amine, CDCl$_3$) δ 7.64 (2H, d, J=8.8 Hz), 7.34–7.22 (5H, m), 6.80 (2H, d, J=8.8 Hz), 5.79–5.77 (1H, m), 5.15 (1H, dd, J=6.2, 8.8 Hz), 4.30–4.19 (2H, m), 3.13 (1H, dd, J=9.2, 12.8 Hz), 3.03 (1H, dd, J=6.2, 12.8 Hz), 2.93–2.84 (1H, m), 2.82 (3H, s), 2.72 (1H, d, J=9.5 Hz), 2.57 (1H, dd, J=4.8, 9.9 Hz), 2.38–2.29 (1H, m), 2.14–2.02 (2H, m), 1.68–1.58 (1H, m), 1.23 (6H, d, J=6.6 Hz); HCl salt: amorphous solid. IR(KBr) 3 3350, 1610 cm$^{-1}$. MS m/z: 382(M+H)$^+$. Anal. Calcd for $C_{23}H_{31}N_3O_2 \cdot HCl \cdot 1.9H_2O$: C, 61.09; H, 7.98; N, 9.29; Found: C, 61.16; H, 7.61; N, 9.12.

Example 13

Preparation of 4-{N-[2-(3-(S)-Methoxymethoxypyrrolidin-1-yl)-1-(S)-phenylethyl]-N-methylamino}-N'-phenylbenzamide This was prepared from 4-{N-[2-(3-(S)-methoxymethoxypyrrolidin-1-yl)-1-(S)-phenylethyl]-N-methylamino}benzoic acid and aniline in 48% yield according to a procedure similar to that described in Example 1(iii).

$^1$H NMR (270 MHz, CDCl$_3$) δ 7.63 (2H, d, J=8.8 Hz), 7.69 (1H, br. s), 7.62 (2H, d, J=7.7 Hz), 7.40–7.24 (7H, m), 7.11 (1H, t, J=7.3 Hz), 6.88–6.80 (2H, m), 5.18 (1H, dd, J=7.7, 15.0 Hz), 4.60 (1H, d, J=7.0 Hz), 4.56 (1H, d, J=7.0 Hz), 4.25–4.10 (1H, m), 3.31 (3H, s), 3.15–3.05 (2H, m), 2.89 (3H, s), 2.95–2.80 (1H, m), 2.80–2.55 (3H, m), 2.15–2.00 (1H, m), 1.90–1.70 (1H, m).

Example 14

Preparation of 4-{N-[2-(3-(S)-Hydroxypyrrolidin-1-yl)-1-(S)-phenylethyl]-N-methylamino}-N'-phenylbenzamide This was prepared from 4-{N-[2-(3-(S)-methoxymethoxypyrrolidin-1-yl)-1-(S)-phenylethyl]-N-methylamino}-N'-phenybenzamide in 16% yield according to a procedure similar to that described in Example 2.

$^1$H NMR (270 MHz, free amine, CDCl$_3$) δ 7.84 (1H, br. s), 7.76 (2H, d, J=88 Hz) 7.66–7.60 (2H, m), 7.40–7.24 (7H, m), 7.10 (1H, t, J=7.3 Hz), 6.84 (2H, d, J=9.2 Hz), 5.18 (1H, dd, J=6.2, 8.8 Hz), 4.30–4.17 (1H, m), 3.15 (1H, dd, J9.2, 12.8 Hz), 3.05 (1H, dd, J=5.9, 12.8 Hz), 3.00–2.85 (1H, m), 2.85 (3H, s), 2.74 (1H, d, J=9.5 Hz), 2.59 (1H, dd, J=4.8, 9.5 Hz), 2.45–2.30 (1H, m), 2.25 (1H br. s), 2.15–2.00 (1H, m), 1.80–1.60 (1H, m); HCl salt: amorphous solid. IR(KBr): 3400, 1600 cm$^{-1}$. Anal. Calcd for $C_{26}H_{29}N_3O_2 \cdot HCl \cdot H_2O$: C, 66.44; H, 6.86; N, 8.94; Found: C, 66.33; H, 7.16; N, 8.86.

Example 15

Preparation of 4-{N-[2-(3-(S)-Methoxymethoxypyrrolidin-1-yl)-1-(S)-phenylethyl]-N-methylamino}-N'-(2-chlorobenzyl)benzamide This was prepared from 4-{N-[2-(3-(S)-methoxymethoxypyrrolidin-1-yl)-1-(S)-phenylethyl]-N-methylamino}benzoic acid and 2-chlorobenzylamine in 88% yield according to a procedure similar to that described in Example 1 (iii).

$^1$H NMR (270 MHz, CDCl$_3$) δ 7.68 (2H, d, J=9.2 Hz), 7.50–7.20 (9H, m), 6.80 (2H, d, J=9.2 Hz), 6.50–6.40 (1H, m), 5.13 (1H, dd, J=6.6, 8.1 Hz), 4.71 (2H, d, J=5.9 Hz), 4.59 (1H, d, J=7.0 Hz), 4.54 (1H, d, J=7.0 Hz), 4.22–4.10 (1H, m), 3.29 (3H, s), 3.15–2.97 (2H, m), 2.87–2.80 (1H, m), 2.85 (3H, s), 2.75–2.52 (3H, m), 2.13–1.98 (1H, m), 1.85–1.70 (1H, m).

Example 16

Preparation of 4-{N-[2-(3-(S)-Hydroxypyrrolidin-1-yl)-1-(S)-phenylethyl]-N-methylamino}-N'-(2-chlorobenzyl)benzamide This was prepared from 4-{N-[2-(3-(S)-methoxymethoxypyrrolidin-1-yl)-1-(S)-phenylethyl]-N-methylamino}-N'-(2-chlorobenzyl)benzamide in 98% yield according to a procedure similar to that described in Example 2.

$^1$H NMR (270 MHz, free amine, CDCl$_3$) δ 7.68 (2H, d, J=8.8 Hz), 7.50–7.20 (9H, m), 6.79 (2H, d, J=8.8 Hz), 6.50–6.40 (1H, m), 5.14 (1H, dd, J=6.0, 9.0 Hz), 4.71 (2H, d, J=5.9 Hz), 4.25–4.20 (1H, m), 3.12 (1H, dd, J=8.8, 12.8 Hz), 3.03 (1H, dd, J=6.2, 12.8 Hz), 2.95–2.80 (1H, m), 2.84 (3H, s), 2.72 (1H,d, J=9.9 Hz), 2.56 (1H, dd, J=4.4, 9.9 Hz), 2.40–2.32 (1H, m), 2.16–2.00 (1H, m), 1.80–1.55 (2H, m); HCl salt: amorphous solid. IR(KBr): 3300, 1630, 1605 cm$^{-1}$. Anal. Calcd for $C_{27}H_{30}N_3O_2Cl \cdot HCl \cdot H_2O \cdot 0.3C_3H_8O$: C, 62.46; H, 6.65; N, 7 83; Found: C, 62.51; H, 7.02; N, 7.94.

Example 17

Preparation of 4-{N-[2-(3-(S)-Methoxymethoxypyrrolidin-1-yl)-1-(S)-phenylethyl]-N-methylamino}-N',N'-dimethylbenzamide This was prepared from 4-{N-[2-(3-(S)-methoxymethoxypyrrolidin-1-yl)-1-(S)-phenylethyl]-N-methylamino}benzoic acid and dimethylamine hydrochloride in 71% yield according to a procedure similar to that described in Example 1 (iii).

$^1$H NMR (270 MHz, CDCl$_3$) δ 7.50–7.20 (7H, m), 7.00–6.75 (2H, m), 5.35–5.25 (1H, m), 4.62 (1H, d, J=7.0 Hz), 4.58 (1H, d, J=6.6 Hz), 4.35–4.20 (1H, m), 3.40–3.20 (2H, m), 3.32 (3H, s), 3.15–3.30 (1H, m), 3.07 (6H, s), 2.95–2.70 (2H, m), 2.81 (3H, s), 2.25–2.05 (1H,m), 2.00–1.80 (1H, m), 1.80–1.55 (1H, m).

Example 18

Preparation of 4-{N-[2-(3-(S)-Hydroxypyrrolidin-1-yl)-1-(S)-phenylethyl]-N-methylamino}-N',N'-dimethylbenzamide This was prepared from 4-{N-[2-(3-(S)-methoxymethoxypyrrolidin-1-yl)-1-(S)-phenylethyl]-N-methylamino}-N',N'-dimethylbenzamide in 88% yield according to a procedure similar to that descrbed in Example 2.

$^1$H NMR (270 MHz, free amine, CDCl$_3$) δ 7.37 (2H, d, J=8.8 Hz), 7.35–7.20 (5H, m), 6.79 (2H, d, J=9.2 Hz), 5.13 (1H,dd, J=6.0, 9.0 Hz), 4.25–4.17 (1H, m), 3.18–2.98 (2H, m), 3.07 (6H, s), 2.91 (1H, ddd, J=5.1, 8.4, 8.4 Hz), 2.81 (3H, s), 2.74 (1H,d, J=9.2 Hz), 2.55 (1H, dd, J=4.8, 9.5 Hz), 2.37–2.25 (1H, m), 2.20–2.00 (1H, m), 1.80–1.55 (2H, m); HCl salt: amorphous solid. IR(KBr): 3400, 1610 cm$^{-1}$. Anal. Calcd for $C_{22}H_{29}N_3O_2 \cdot HCl \cdot H_2O$: C, 62.62; H, 7.64; N,9.96; Found: C, 62.52; H, 7.86; N, 9.98.

Example 19

Preparaiion of 4-{N-[1-(S)-Phenyl-2-(3-(S)-tetrahydropyran-2-yloxypyrrolidin-1-yl)-ethyl]-N-methylamino}-N'-methyl-N'-propylbenzamide This was prepared from 2-(R)-phenyl-2-(3-(S)-tetrahydropyran-2-yloxypyrrolidin-1-yl)ethanol and 1-(S)-phenyl-2-(3-(S)-tetrahydropyran-2-yloxypyrrolidin-1-yl)ethanol in 32% over all yield according to a procedure similar to that described in Example 1 (i)–(iii).

$^1$H NMR (270 MHz, CDCl$_3$) δ 7.40–7.20 (7H, m), 6.77 (2H, d, J=8.8 Hz), 5.11 (1H, dd, J=7.0, 7.7 Hz), 4.60–4.55

(0.6H, m), 4.53–4.47 (0.4H, m), 4.38–4.25 (1H, m), 3.90–3.75 (1H, m), 3.55–3.30 (3H, m), 3.15–2.92 (2H, m), 3.03 (3H, s), 2.81 (1.8H, s), 2.80 (1.2H, s), 2.80–2.70 (1H, m), 2.68–2.50 (3H, m), 2.15–1.95 (1H, m), 1.90–1.45 (9H, m), 1.00–0.80 (3H, m).

Example 20

Preparation of 4-{N-[2-(3-(S)-Hydroxypyrrolidin-1-yl)-1-(S)-phenylethyl]-N-methylamino}-N'-methyl-N'-propylbenzamide This was prepared from 4-{N-[1-(S)-phenyl-2-(3-(S)-tetrahydropyran-2-yloxypyrrolidin-1-yl)ethyl]-N-methylamino)-N'-methyl-N'-propylbenzamide in 83% yield according to a procedure similar to that described in Example 2.

$^1$H NMR (270 MHz, free amine, CDCl$_3$) δ 7.40–7.20 (7H, m), 6.79 (2H, d, J=8.8 Hz), 5.11 (1H, dd, J=6.2, 8.8 Hz), 4.28–4.16 (1H, m), 3.46–3.32 (2H, m), 3.18–2.98 (1H, m), 3.03 (3H, s), 2.90 (1H, ddd, J=5.1, 8.4, 8.5 Hz), 2.81 (3H, s), 2.78–2.70 (1H, m), 2.56 (1H, dd, J=4.6, 9.7 Hz), 2.32 (1H, ddd, J=6.2, 9.2, 9.2 Hz), 2.18–2.00 (1H, m), 1.90–1.50 (4H, m), 1.00–0.80 (3H,m); HCl salt: amorphous solid. IR(KBr): 3350, 1610 cm$^{-1}$. Anal. Calcd for C$_{24}$H$_{33}$N$_3$O$_2$.HCl.0.75H$_2$O: C, 64.70; H, 8.03; N,9.43; Found: C, 64.68; H, 8.39; N, 9.49.

Example 21

Preparation of 3-{N-[2-(3-(S)-Methoxymethoxypyrrolidin-1-yl)-1-(S)-phenylethyl]-N-methylamino}-N'-propylbenzamide (i) Methyl-3-{N-[2-(3-(S)-methoxymethoxypyrrolidin-1-yl)-1-(S)-phenylethyl]-N-methylamino}benzoate This was prepared from 2-(3-(S)-methoxymethoxypyrrolidin-1-yl)-2-R)-phenylethanol and methyl 3-methylaminobenzoate in 78% yield according to a procedure similar to that described in Example 1 (i).

$^1$H NMR (270 MHz, CDCl$_3$) δ 7.51–7.48 (1H, m), 7.39–7.34 (1H, m), 7.33–7.20 (6H, m), 7.04–6.98 (1H, m), 5.15–5.05 (1H, m), 4.59 (1H, d, J=7.0 Hz), 4.55 (1H, d, J=7.0 Hz), 4.20–4.10 (1H, m), 3.89 (3H, s), 3.30 (3H, s), 3.15–2.97 (2H, m), 2.90–2.80 (1H, m), 2.82 (3H, s), 2.77–2.55 (3H, m), 2.12–1.98 (1H,m), 1.83–1.60 (1H, m).

(ii) 3-{N-[2-(3-(S)-Methoxymethoxypyrrolidin-1-yl)-1-(S)-phenylethyl]-N-methylamino}benzoic Acid This was prepared from methyl 3-{N-[2-(3-(S)-methoxymethoxypyrrolidin- 1yl)-1-(S)-phenylethyl]-N-methylamino}benzoate in 100% yield according to a procedure similar to that described in Example 1 (ii).

$^1$H NMR (270 MHz, CDCl$_3$) δ 7.98 (1H, br. s), 7.47 (1H, d, J=7.7 Hz), 7.30–7.10 (6H, m), 6.82 (1H, d, J=2.2, 8.4 Hz), 5.70–5.60 (1H, m), 4.63 (1H, d, J=6.6 Hz), 4.59 (1H, d, J=6.6 Hz), 4.40–4.30 (1H, m), 4.04 (1H, br. s), 3.77 (1H, dd, J=5.9, 11.7 Hz), 3.68–3.58 (1H, m), 3.48–3.28 (2H, m), 3.32 (3H, s), 3.12–3.00 (1H, m), 2.96–2.84 (1H, m), 2.71 (3H, s), 2.26–2.12 (1H, m), 2.06–1.92 (1H,m).

(iii) 3-{N-[2-(3-(S)-Methoxymethoxypyrrolidin-1-yl)-1-(S)-phenylethyl]-N-methylamino}-N'-propylbenzamide This was prepared from 3-{N-[2-(3-(S)-methoxymethoxypyrrolidin-1-yl)-1-(S)-phenylethyl]-N-methylamino}benzoic acid and n-propylamine in 78% yield according to a procedure similar to that described in Example 1 (iii).

$^1$H NMR (270 MHz, CDCl$_3$) δ 7.34–7.19 (7H, m), 6.98 (1H, d, J=7.3 Hz), 6.91 (1H, dd, J=2.2, 8.1 Hz), 6.22 (1H, br. s), 5.16–5.06 (1H, m), 4.57 (1H, d, J=6.6 Hz), 4.53 (1H, d, J=6.6 Hz), 4.22–4.12 (1H, m), 3.46–3.32 (2H, m), 3.28 (3H, s), 3.16–2.96 (1H, m), 2.81 (3H, s), 2.86–2.52 (4H, m), 2.14–1.98 (1H,m), 1.82–1.56 (4H, m), 0.98 (3H, t, J=7.3 Hz).

Example 22

Preparation of 3-{N-[2-(3-(S-Hydroxyprrolidin-1-yl)-1-(S)-phenylethyl]-N-methylamino}-N'-propylbenzamide This was prepared from 3-{N-[2-(3-(S)-methoxymethoxypyrrolidin-1-yl)-1-(S)-phenylethyl]-N-methylamino}-N'-propylbenzamide in 90% yield according to a procedure similar to that described in Example 2.

$^1$H NMR (270 MHz, CDCl$_3$) δ 7.42–7.37 (1H, m), 7.36–7.19 (6H, m), 6.97 (1H, d, J=7.7 Hz), 6.92 (1H, dd, J=2.6, 8.1 Hz), 6.21 (1H, br. s), 5.13 (1H, dd, J=5.9, 8.8 Hz), 4.26–4.14 (1H, m), 3.48–3.32 (2H, m), 3.18–3.00 (2H, m), 2.92 (1H, ddd, J=4.3, 8.4, 8.4 Hz), 2.86–2.72 (1H, m), 2.78 (3H, s), 2.50 (1H, dd, J=4.8, 9.9 Hz), 2.36–2.22 (1H, m), 2.20–2.02 (1H, m), 2.00–1.70 (2H,m), 1.63 (2H dd, J=7.3, 14.7, 14.7 Hz), 0.98 (3H, t, J=7.3 Hz); HCl salt: brown powder. mp: 105–114° C. IR(KBr): 3350, 1635 cm$^{-1}$. MS m/z: 381(M$^+$). Anal. Calcd for C$_{23}$H$_{31}$N$_3$O$_2$.HCl.0.7H$_2$O.0.3C$_6$H$_{14}$O: C,64.58; H, 8.22; N, 9.11; Found: C, 64.42; H, 8.54; N, 9.34.

Example 23

Preparation of 2-Chloro-4-{N-[1-(S)-phenyl-2-(3-(S)-tetrahydropyran-2-yloxypyrrolidin-1-yl)ethyl]-N-methylamino}-N'-propylbenzamide (i) Methyl 2-chloro-4-{N-[1-(S)-phenyl-2-(3-(S)-tetrahydropyran-2-yloxypyrrolidin-1-yl)-ethyl]-N-methylamino}benzoate This was prepared from 2-(R)-phenyl-2-(3-(S)-tetrahydropyran-2-yloxypyrrolidin-1-yl)ethanol and 1-(S)-phenyl-2-(3-(S)-tetrahydropyran-2-yloxypyrrolidin-1-yl) ethanol and methyl 2-chloro-4-methylaminobenzoate in 40% yield according to a procedure sirnilar to that described in Example 1 (i).

$^1$H NMR (270 MHz, CDCl$_3$) δ 7.86–7.80 (1H, m), 7.38–7.22 (5H m), 6.83–6.78 (1H, m), 6.72–6.65 (1H, m), 5.10 (1H dd, J=6.6, 7.7 Hz), 4.60–4.55 (0.6H, m), 4.50–4.45 (0.4H, m), 4.38–4.22 (1H, m), 3.86 (3H s), 3.85–3.75 (1H, m), 3.50–3.37 (1H, m), 3.13–2.90 (3H, m), 2.85 (1.8H, s), 2.84 (1.2H, s), 2.80–2.50 (3H, m), 2.20–1.95 (1H, m), 1.95–1.40 (7H m).

(ii) 2-Chloro-4-{N-[1-(S)-phenyl-2-(3-(S)-tetrahydropyran-2-yloxypyrrolidin-1-yl)ethyl]-N-methylamino}benzoic Acid This was prepared from methyl 2-chloro-4-{N-[1-(S)-phenyl-2-(3-(S)-tetrahydropyran-2-yloxypyrrolidin-1-yl) ethyl]-N-methylamino}benzoate in 100% yield according to a procedure similar to that descnbed in Example 1 (ii).

$^1$H NMR (270 MHz CDCl$_3$) δ 7.86–7.75 (1H, m), 7.38–7.22 (5H, m), 6.80–6.60 (2H, m), 5.20–5.10 (1H, m), 4.60–4.55 (0.6H, m), 4.50–4.45 (0.4H, m), 4.38–4.22 (1H, m), 3.37 (3H, m), 3.20–3.00 (2H, m), 2.80–2.50 (4H,.m), 2.69 (3H, s), 2.20–1.95 (1H, m), 1.95–1.40 (7H, m).

(iii) 2-Chloro-4-{N-[1-(S)-phenyl-2-(3-(S)-tetrahydropyran-2-yloxypyrrolidin-1-yl)-ethyl]-N-methylamino}-N'-propylbenzamide This was prepared from 2-chloro-4-{N-[1-(S)-phenyl-2-(3-(S)-tetrahydropyran-2-yloxypyrrolidin-1-yl)ethyl]-N-methylamino}benzoic acid and n-propylamine in 68% yield according to a procedure similar to that described in Example 1 (iii).

¹H NMR (270 MHz, CDCl₃) δ 7.78–7.72 (1H, m), 7.38–7.22 (5H, m), 6.79–6.70 (2H, m), 6.60–6.48 (1H, m), 5.07 (1H, dd, J=6.6, 7.3 Hz), 4.60–4.55 (0.6H, m), 4.50–4.45 (0.4H, m), 4.38–4.22 (1H, m), 3.90–3.75 (1H, m), 3.50–3.37 (3H, m), 3.13–2.90 (2H, m), (2H m), 2.28 (3H, s), 2.80–2.50 (4H, m), 2.20–1.95 (1H, m), 1.95–1.40 (9H, m), 0.99 (3H, t, J=7.3 Hz).

Example 24

Preparation of 2-Chloro-4-{N-[2-(3-(S)-hydroxypyrrolidin-1-yl)-1-(S)-phenylethyl]-N-methylamino}-N'-propylbenzamide This was prepared from 2-chloro-4-{N-[1-(S)-phenyl-2-(3-(S)-tetrahydropyran-2-yloxypyrrolidin-1-yl)-ethyl]-N-methylamaino}-N'-propylbenzamide in 89% yield according to a procedure similar to that described in Example 2.

¹H NMR (270 MHz, free amine, CDCl₃) δ 7.76 (1H, d, J=8.8 Hz), 7.40–7.20 (5H, m), 6.75 (1H, dd, J=2.6, 8.8 Hz), 6.72 (1H, d, J=2.6 Hz), 6.54 (1H, br. s), 5.07 (1H, dd, J=5.9, 9.2 Hz), 4.30–4.20 (1H, m), 3.46–3.35 (2H, m), 3.12 (1H, dd, J=9.2, 12.8 Hz), 3.01 (1H, dd, J=6.0, 13.0 Hz), 2.95–2.78 (1H, m), 2.83 (3H, s), 2.72 (1H, d, J=9.9 Hz), 2.58 (1H, dd, J=4.8, 9.5 Hz), 2.35 (1H, ddd, J=6.0, 8.9, 9.0 Hz), 2.18–2.00 (1H, m), 1.90–1.50 (4H, m), 0.99(3H, t, J=7.7 Hz); HCl salt: amorphous solid. IR(KBr): 3350, 1600 cm⁻¹. Anal. Calcd for $C_{23}H_{30}N_3O_2Cl \cdot HCl \cdot 0.2H_2O$: C, 60.58; H, 6.94; N, 9.21; Found: C, 60.29; H, 7.13; N, 9.13.

Example 25

Preparation of 2-Methoxy-4-{N-[2-(3-(S)-methoxymethoxypyrrolidin-1-yl)-1-(S)-phenylethyl]-N-methylamino}-N'-propylbenzamide (i) Methyl 2-methoxy-4-{N-[2-(3-(S)-methoxymethoxypyrrolidin-1-yl)-1-(S)-phenylethyl]-N-methylamino}benzoate This was prepared from 2-(3-(S)-methoxymethoxypyrrolidin-1-yl)-1-(S)-phenylethanol and 2-(3-(S)-methoxymethoxypyrrolidin-1-yl)-2-(R)-phenylethanol and methyl 2-methoxy-4-methylaminobenzoate in 41% yield according to a procedure similar to that described in Example 1 (i).

¹H NMR (270 MHz, CDCl₃) δ 7.79 (1H, d, J=9.2 Hz), 7.36–7.20 (5H, m), 6.40 (1H, dd, J=2.4, 8.9 Hz), 6.27 (1H, d, J=2.6 Hz), 5.13 (1H, dd, J=7.0, 8.1 Hz), 4.60 (1H, d, J=7.0 Hz), 4.56 (1H, d, J=6.6 Hz), 4.25–4.15 (1H,m), 3.86 (3H, s), 3.82 (3H, s), 3.30 (3H, s), 3.14–2.96 (2H, m), 2.87 (3H, s), 2.90–2.80 (1H, m), 2.78–2.52 (3H, m), 2.14–1.96 (1H, m), 1.84–1.70 (1H, m).

(ii) 2-Methoxy-4-{N-[2-(3-(S)-methoxymethoxypyrrolidin-1-yl)-1-(S)-phenylethyl]-N-methylamino}benzoic Acid This was prepared from methyl 2-methoxy-4-{N-[2-(3-(S)-methoxymethoxypyrrolidin-1-yl)-1-(S)-phenylethyl]-N-methylamino}benzoate in 100% yield according to a procedure similar to that described in Example 1 (ii).

¹H NMR (270 MHz, CDCl₃) δ 7.98 (1H d, J=8.8 Hz), 7.38–7.16 (5H, m), 6.54 (1H, dd, J=2.4, 9.0 Hz), 6.35–6.25 (1H, m), 5.20–5.05 (1H, m), 4.60 (1H, d, J=7.0 Hz), 4.56 (1H, d, J=7.0 Hz), 4.25–4.15 (1H,m), 3.99 (3H, s), 3.30 (3H, s), 3.14–3.05 (2H, m), 2.91 (3H, s), 2.90–2.52 (4H, m), 2.14–2.00 (1H, m), 1.90–1.70 (1H, m).

(iii) 2-Methoxy-4-{N-[2-(3-(S)-methoxymethoxypyrrolidin-1-yl)-1-(S)-phenylethyl]-N-methylamino}-N'-propylbenzamide This was prepared from 2-methoxy-4-{N-[2-(3-(S)-methoxymethoxypyrrolidin-1-yl)-1-(S)-phenylethyl]-N-methylamino}benzoic acid and n-propylamine in 84% yield according to a procedure similar to that described in Example 1 (iii).

¹H NMR (270 MHz, CDCl₃) δ 8.07 (1H, d, J=8.8 Hz), 7.78–7.68 (1H, m), 7.36–7.20 (5H, m), 6.51 (1H, dd, J=2.4, 9.0 Hz), 6.27 (1H, d, J=2.2 Hz), 5.11 (1H, dd, J=6.6, 8.1 Hz), 4.60 (1H, d, J=7.0 Hz), 4.56 (1H, d, J=6.6 Hz), 4.25–4.15 (1H,m), 3.89 (3H, s), 3.45–3.35 (2H, m), 3.30 (3H, s), 3.14–2.96 (2H, m), 2.86 (3H, s), 2.90–2.80 (1H, m), 2.78–2.52 (3H, m), 2.14–1.96 (1H, m), 1.84–1.70 (1H, m), 1.68–1.50 (2H, m), 0.97 (3H, t, J=7.3 Hz).

Example 26

Preparation of 4-{N-[2-(3-(S)-Hydroxypyrrolidin-1-yl)-1-(S)-phenylethyl]-N-methylamino}-2-methoxy-N'-propylbenzamide This was prepared from 2-methoxy-4-{N-[2-(3-(S)-methoxymethoxypyrrolidin-1-yl)-1-(S)-phenylethyl]-N-methylamino}-N'-propylbenzamide in 85% yield according to a procedure similar to that described in Example 2.

¹H NMR (270 MHz, free amine, CDCl₃) δ 8.07 (1H, d, J=8.8 Hz), 7.78–7.68 (1H, m), 7.38–7.22 (5H, m), 6.53 (1H, dd, J=2.2, 8.8 Hz), 6.27 (1H, d, J=2.2 Hz), 5.13 (1H, dd, J=6.2, 8.4 Hz), 4.30–4.20 (1H,m), 3.89 (3H s), 3.45–3.35 (2H, m), 3.20–3.00 (2H, m), 2.95–2.80 (1H, m), 2.85 (3H, s), 2.74 (1H, d, J=9.5 Hz), 2.58 (1H, dd, J=4.8, 9.5 Hz), 2.40–2.27 (1H m), 2.18–2.02 (1H, m), 1.95–1.55 (4H, m), 0.97 (3H, t, J=7.3 Hz); HCl salt: amorphous solid. IR(KBr): 3400, 1600 cm⁻¹. Anal. Calcd for $C_{24}H_{33}N_3O_3 \cdot HCl \cdot 0.8CH_4O$: C, 62.89; H, 7.92; N, 8.87; Found: C, 63.16; H, 8.32; N, 9.20.

Example 27

Preparation of 3-Methoxy-4-{N-[2-(3-(S)-methoxymethoxypyrrolidin-1-yl)-1-(S)-phenylethyl]-N-methylamino}-N'-propylbenzamide (i) Methyl 3-methoxy-4-{N-[2-(3-(S)-methoxymethoxypyrrolidin-1-yl)-1-(S)-phenylethyl]-N-methylamino}benzoate This was prepared from 2-(3-(S)-methoxymethoxypyrrolidin-1-yl)-1-(S)-phenylethanol and 2-(3-(S)-methoxymethoxypyrrolidin-1-yl)-2-(R)-phenylethanol and methyl 3-methoxy-4-methylaminobenzoate in 60% yield according to a procedure similar to that described in Example 1 (i).

¹H NMR (270 MHz, CDCl₃) δ 7.58–7.53 (2H, m), 7.31–7.20 (5H, m), 6.71 (1H, d, J=8.4 Hz), 5.13 (1H, t, J=7.3 Hz), 4.59 (1H, d, J=7.0 Hz), 4.55 (1H, d, J=7.0 Hz), 4.15–4.05 (1H,m), 3.95 (3H, s), 3.89 (3H, s), 3.30 (3H, s), 3.09 (2H, d, J=7.0 Hz), 2.87 (1H, dd, J=6.2, 9.9 Hz), 2.60 (3H, s), 2.60–2.52 (2H, m), 2.47 (1H, dd, J=4.0, 9.9Hz), 2.08–1.92 (1H, m), 1.73–1.60 (1H, m).

(ii) 3-Methoxy-4-{N-[2-(3-(S)-methoxymethoxypyrrolidin-1-yl)-1-(S)-phenylethyl]-N-methylamino}benzoic Acid This was prepared from methyl 3-methoxy-{N-[2-(3-(S)-methoxymethoxypyrrolidin-1-yl)-1-(S)-phenylethyl]-N-methylamino}benzoate in 100% yield according to a procedure similar to that described in Exanple 1 (ii).

¹H NMR (270 MHz, CDCl₃) δ 7.52–7.45(2H, m), 7.32–7.12 (5H, m), 6.65 (1H, d, J=8.4 Hz), 5.47 (1H, dd, J=6.6, 7.0 Hz), 4.64 (1H, d, J=7.0 Hz), 4.60 (1H, d, J=6.6 Hz), 4.45–4.35 (1H,m), 4.02 (3H, s), 3.85–3.70 (3H, m), 3.68–3.57 (1H, m), 3.32 (3H, s), 3.30–3.05 (2H, m), 2.64 (3H, s), 2.40–2.23 (1H, m), 2.15–2.00 (1H, m).

(iii) 3-Methoxy-4-{N-[2-(3-(S)-methoxymethoxypyrrolidin-1-yl)-1-(S)-phenylethyl]-N-methylamino}-N'-propylbenzamide This was prepared from 3-methoxy-4-{N-[2-(3-(S)-methoxymethoxypyrrolidin-1-yl)-1-(S)-phenylethyl]-N-methylamino}benzoic acid and n-propylamine in 64% yield according to a procedure similar to that described in Example 1 (iii).

$^1$H NMR (270 MHz, CDCl$_3$) δ 7.45 (1H, d, J=1.8 Hz), 7.32–7.18 (5H, m), 7.11 (1H, dd, J=1.8,8.4 Hz), 6.66 (1H, d, J=8.1 Hz), 6.15–6.05 (1H,m), 5.03 (1H,t, J=7.7 Hz), 4.49 (1H, d, J=7.0 Hz), 4.54 (1H, d, J=7.0 Hz), 4.15–4.05 (1H,m), 3.96 (3H, s), 3.45–3.35 (2H, m), 3.30 (3H, s), 3.08 (2H, d, J=7.7 Hz), 2.95–2.85 (1H, m), 2.65–2.50 (2H, m), 2.57 (3H, s), 2.46 (1H, dd, J=4.4, 9.9 Hz), 2.10–1.90 (1H, m), 1.75–1.55 (3H, m), 0.99 (3H, t, J=7.3 Hz).

Example 28

Preparation of 4-{N-[2-(3-(S)-Hydroxypyrrolidin-1-yl)-1-(S)-phenylethyl]-N-1-methylamino}-3-methoxy-N'-propylbenzamide This was prepared from 3-methoxy-4-{N-[2-(3-(S)-methoxymethoxypyrrolidin-1-yl)-1-(S)-phenylethyl]-N-methylamino}-N'-propylbenzamide in 77% yield according to a procedure similar to that described in Example 2.

$^1$H NMR (270 MHz, free amine, CDCl$_3$) δ 7.48 (1H, d, J=2.2 Hz), 7.37–7,27 (5H, m), 7.12 (1H, dd, J=2.2, 8.4 Hz), 6.72 (1H, d, J=8.4 Hz), 6.15–6.05 (1H,m), 5.16 (1H,dd, J=6.6, 8.8 Hz), 4.15–4.05 (1H,m), 3.97 (3H, s), 3.45–3.35 (2H, m), 3.23 (2H, dd, J=8.8, 12.5 Hz), 2.99 (1H, dd, J=6.4, 12.3 Hz), 2.80–2.70 (1H, m), 2.59 (3H, s), 2.45 (1H, dd, J=4.4, 9.9 Hz), 2.20–1.90 (2H, m), 1.75–1.40 (4H, m), 0.99 (3H, t, J=7.3 Hz); HCl salt: amorphous solid. IR(KBr): 3350, 1630 cm$^{-1}$.

Example 29

Preparation of 3-chloro-4-{N-[2-(3-(S)-methoxymethoxypyrrolidin-1-yl)-1-(S)-phenylethyl]-N-methylamino}-N'-propylbenzamide (i) 3-chloro-4-{N-[2-(3-(S)-methoxymethoxypyrrolidin-1-yl)-1-(S)-phenylethyl]-N-methylamino}benzonitrile To a stirred solution of the mixture of 2-(3-(S)-methoxymethoxypyrrolidin-1-yl)-1-(S)-phenylethanol and 2-(3-(S)-methoxymethoxypyrrolidin-1-yl)-2-(R)-phenylethanol (251 mg, 1.00 mmol) and triethylamine (0.167 ml, 1.20 mmol) in CH$_2$Cl$_2$ (4 ml) was added methanesulfonyl chloride (0.093 ml, 1.20 mmol) dropwise at 0° C. (ice bath). After 15.5 h stirring at room temperature, the reaction mixture was washed with saturated NaHCO$_3$ aqueous solution, brine, dried (Na$_2$SO$_4$), and concentrated to give 238 mg of brown viscous oil-(i). To a suspension of NaH, (48 mg, 1.20 mmol) in N,N-dimethylformamide (2 ml) was added a solution of 3-chloro-4-methylaminobenzonitrile (200 mg, 1.20 mmol) at room temperature. After stirring for 45 min, to this mixture was added a solution of the above brown viscous oil-(i) in N,N-dimethylformamide (2 ml) at room temperature and the mixture was stirred at room temperature for 4.5 h. H$_2$O was added to this mixture, basified with 25%-NH$_4$OH, and extracted with CH$_2$Cl$_2$. The extract was washed with water, brine, dried (Na$_2$SO$_4$), and concentrated to give brown oil, which was purified by column chromatography (silica gel 20 g, CH$_2$Cl$_2$/MeOH 100/1–50/1) to afford 244 mg (61%) of brown oil.

$^1$H NMR (270 MHz, CDCl$_3$) δ 7.61 (1H, d, J=2.2 Hz), 7.43–7.25 (6H, m), 6.98 (1H, d, J=8.4 Hz), 5.03 (1H, dd, J=7.3, 7.7 Hz), 4.58 (1H, d, J=6.6 Hz), 4.54 (1H, d, J=6.6 Hz), 4.10–3.97 (1H,m), 3.31 (3H, s), 3.10 (2H, dd, J=1.5, 7.7 Hz), 2.75–2.65 (1H, m), 2.69 (3H, s), 2.55–2.43 (3H, m), 2.03–1.85 (1H, m), 1.70–1.60 (1H, m).

(ii) 3-Chloro-4-{N-[2-(3-(S)-methoxymethoxypyrrolidin-1-yl)-1-(S)-phenylethyl]-N-methylamino}-N'-propylbenzamide To a suspension of t-BuOK (381 mg, 3.05 mmol) and H$_2$O (0.055 ml, 3.05 mmol) in t-BuOH, (1.0 ml) was added a solution of 3-chloro-4-{N-[2-(3-(S)-methoxymethoxypyrrolidin-1-yl)-1-(S)-phenylethyl]-N-methylamino}benzonitrile (244 mg, 0.611 mmol) in t-BuOH, (1.0 ml) at room temperature. After refluxing for 0.5 h. the mixture was allowed to cool to room temperature. n-Propyliodide (0.298 ml, 3.05 mmol) was added to the mixture, and the mixture was refluxed for 3 h. After cooling down to room temperature, the solvent was evaporated. The residue was dissolved in CH$_2$Cl$_2$ and washed with water and brine, dried (Na$_2$SO$_4$), and concentrated to give pale brown oil, which was purified by column chromatography (silice gel, 15 g, CH$_2$Cl$_2$/MeOH: 80/1–50/1) to give 206 mg (73%) of ivory amorphous.

$^1$H NMR (270 MHz, CDCl$_3$) δ 7.77 (1H, d, J=2.2 Hz), 7.52 (1H,dd, J=2.2, 8.4 Hz), 7.36–7.20 (5H, m), 6.92 (1H, d, J=8.4 Hz), 6.15–6.00 (1H,m), 4.91 (1H, dd, J=7.3, 7.7 Hz), 4.57 (1H, d, J=7.0 Hz), 4.53 (1H, d, J=7.0 Hz), 4.10–3.98 (1H,m), 3.45–3.35 (2H, m), 3.29 (3H, s), 3.14 (1H, dd, J=7.7, 12.5 Hz), 3.05 (1H, dd, J=7.3, 12.5 Hz), 2.73 (1H, dd, J=6.2, 9.9 Hz), 2.64 (3H, s), 2.55–2.43 (3H, m), 2.05–1.88 (1H, m), 1.75–1.55 (3H, m), 0.96 (3H, t, J=7.3 Hz).

Example 30

Preparation of 3-Chloro-4-{N-[2-(3-(S)-hydroxypyrrolidin-1-yl)-1-(S)-phenylethyl]-N-methylamino}-N'-propylbenzamide This was prepared from 3-chloro-4-{N-[2-( 3-(S)-methoxymethoxypyrrolidin-1-yl)-1(S)-phenylethyl]-N-methylamino}-N'-propylbenzamide in 96% yield according to a procedure similar to that described in Example 2.

$^1$H NMR (270 MHz, free amine, CDCl$_3$) δ 7.81 (1H, d, J=2.2 Hz), 7.51 (1H,dd. J=2.2, 8.4 Hz), 7.42–7.22 (5H, m), 6.93 (1H, d, J=8.4 Hz), 6.15–6.00 (1H,m), 4,99 (1H, dd, J=7.3, 7.9 Hz), 4.20–4.05 (1H,m), 3.45–3.35 (2H, m), 3.16 (1H, dd, J=7.7, 12.5 Hz), 3.08 (1H, dd, J=7.3, 12.5 Hz), 2.75–2.60 (2H, m), 2.65 (3H, s), 2.41 (1H, dd, J=4.4, 9.5 Hz), 2.25–2.15 (1H, m), 2.08–1.93 (1H, m), 1.90–1.40 (4H, m), 0.99 (3H, t, J=7.3 Hz); Fumaric acid salt: amorphous solid. IR(KBr): 3350, 1630 cm$^{-1}$. MS m/z: 416, 418 (M+H)$^+$. Anal. Calcd for C$_{23}$H$_{30}$N$_3$O$_2$Cl.C$_4$H$_4$O$_4$.H$_2$O: C, 58.96; H, 6.60; N, 7.64; Found: C, 59.35; H, 6.64; N, 7.55.

Example 31

Preparation of 6-{N-[2-(3-(S)-methoxymethoxypyrrolidin-1-yl)-1-(S)-phenylethyl]-N-methylamino}-N'-propylnicotinamide (i) Methyl 6-{N-[2-(3-(S)-methoxymethoxypyrrolidin-1-yl)-1-(S)-phenylethyl]-N-methylamino}nicotinate This was prepared from 2-(3-(S)-methoxymethoxypyrrolidin-1-yl)-1-(S)-phenylethanol and 2-(3-(S)-methoxymethoxypyrrolidin-1-yl)-2-(R)-phenylethanol and methyl 6-methylaminonicotinate in 60% yield according to a procedure similar to that described in Example 29 (i).

$^1$H NMR (270 MHz, CDCl$_3$) δ 8.83 (1H, d, J=2.2 Hz), 8.01 (1H, dd, J=2.2, 9.2 Hz), 7.35–7.20 (5H, m), 6.48 (1H, d, J=9.2 Hz), 6.44–6.32 (1H, m), 4.59 (1H, d, J=7.0 Hz), 4.56 (1H, d, J=6.6 Hz), 4.22–4.12 (1H, m), 3.86 (3H, s), 3.30 (3H, s), 3.17–2.92 (3H, m), 2.83 (3H, s), 2.80–2.70 (1H, m), 2.65–2.50 (2H, m), 2.12–1.95 (1H, m), 1.80–1.65 (1H, m).

(ii) 6-{N-[2-(3-(S)-Methoxymethoxypyrrolidin-1-yl)-1-(S)-phenylethyl]-N-methylamino}nicotinic Acid This was prepared from methyl 6-{N-[2-(3-(S)-methoxymethoxypyrroldin-1-yl)-1-(S)-phenylethyl]-N-methylamino}nicotinate in 100% yield according to a procedure similar to that described in Example 1 (ii).

$^1$H NMR (270 MHz, CDCl$_3$) δ 8.80–8.75 (1H, m), 7.95–7.87 (1H, m), 7.35–7.15 (5H, m), 6.57 (1H, br.s), 6.42 (1H, d, J=9.2 Hz), 4.62 (1H, d, J=6.6 Hz), 4.59 (1H, d, J=7.0 Hz), 4.35–4.00 (2H, m), 3.50–3.25 (2H, m), 3.32 (3H, s), 3.18–3.08 (1H, m), 3.02–2.70 (3H, m), 2.79 (3H, s), 2.20–2.05 (1H, m), 1.90–1.80(1H, m).

(iii). 6-{N-[2-(3-(S)-Methoxymethoxypyrrolidin-1-yl)-1-(S)-phenylethyl]-N-methylamino}-N'-propylnicotinamide This was prepared from 6-{N-[2-(3-(S)-methoxymethoxypyrrolidin-1-yl)-1-(S)-phenylethyl]-N-methylamino}nicotinic acid and n-propylamine in 65% yield according to a procedure similar to that described in Example 1 (iii).

$^1$H NMR (270 MHz, CDCl$_3$) δ 8.57 (1H, d, J=2.6 Hz), 7.89 (1H, dd, J=2.6, 9.2 Hz), 7.35–7.20 (5H, m), 6.50 (1H, d, J=9.2 Hz), 6.40–6.35 (1H, m), 6.00–5.90 (1H, m), 4.59 (1H, d, J=7.0 Hz), 4.56 (1H, d, J=7.0 Hz), 4.20–4.10 (1H, m), 3.45–3.35 (2H, m), 3.30 (3H, s), 3.17–2.92 (3H, m), 2.82 (3H, s) 2.80–2.70 (1H, m), 2.65–2.50 (2H, m), 2.12–1.95 (1H, m), 1.80–1.55 (3H, m), 0.99 (3H, t, J=7.3 Hz).

Example 32

Preparation of 6-{N-[2-(3-(S)-Hydroxypyrrolidin-1-yl)-1-(S)-phenylethyl]-N-methylamino}-N'-propylnicotinamide This was prepared from 6-{N-[2-(3-(S)-methoxymethoxypyrrolidin-1-yl)-1-(S)-phenylethyl]-N-methylamino}-N'-propylnicotinamide in 73% yield according to a procedure sinilar to that described in Example 2.

$^1$H NMR (270 MHz, free amine, CDCl$_3$) δ 8.58 (1H, d, J=2.6 Hz), 7.89 (1H, dd, J=2.6, 8.8 Hz), 7.35–7.20 (5H, m), 6.50 (1H, d, J=9.5 Hz), 6.36 (1H, dd, J=5.9, 9.9 Hz), 6.00–5.92 (1H, m), 4.25–4.15 (1H, m), 3.45–3.35 (2H, m), 3.17 (1H, dd, J=9.9, 12.5 Hz), 3.05–2.95 (2H, m), 2.81 (3H, s), 2.72 (1H, d, J=9.5 Hz), 2.62 (1H, dd, J=4.8. 9.9 Hz), 2.40–2.25 (1H, m), 2.17–2.02 (1H, m), 1.95–1.75 (2H, m), 1.70–1.55 (2H, m), 0.98 (3H, t, J=7.3 Hz). Fumaric acid salt: amorphous solid. IR(KBr): 3350, 1630 cm$^{-1}$. MS m/z: 383(M+H)$^+$. Anal. Calcd for C$_{22}$H$_{30}$N$_4$O$_2$.C$_4$H$_4$O$_4$.1.5H$_2$O: C, 59.42; H, 7.10; N, 10.66; Found: C, 59.50; H, 7.43; N, 10.73.

Example 33

Preparation of 4-{N-[1-(S)-(3-Methoxymethoxyphenyl)-2-(3-(S)-methoxymethoxypyrrolidin-1-yl)-ethyl]-N-methylamino}-N'-propylbenzamide (i) Methyl 4-{N-[1-(S)-(3-methoxyethoxylphenyl)-2-(3-(S)-methoxymethoxypyrrolidin-1-yl)-ethyl]-N-methylamino}benzoate This was prepared from the mixture of 2-(R)-(3-methoxymethoxyphenyl)-2-(3-(S)-methoxymethoxypyrrolidin-1-yl)ethanol and 1-(S)-(3-methoxymethoxyphenyl)-2-(3-(S)-methoxymethoxypyrrolidin-1-yl)ethanol and methyl 4-methylaminobenzoate in 60% yield according to a procedure similar to that described in Example 1 (i).

$^1$H NMR (270 MHz, CDCl$_3$) δ 7.89 (2H, d, J=9.2 Hz), 7.27–7.19 (1H, m), 6.98–6.88 (3H, m), 6.77 (2H, d, J39.2 Hz), 5.14 (2H, s), 5.14–5.08 (1H, m), 4.59 (1H, d, J=6.6 Hz), 4.55 (1H, d, J=7.0 Hz), 4.22–4.12 (1H, m), 3.85 (3H, s), 3.46 (3H, s), 3.30 (3H, s), 3.04 (2H, d, J=8.1 Hz), 2.88 (3H, s), 2.85–2.53 (4H, m), 2.10–1.98 (1H, m), 183–1.70 (1H, m).

(ii) 4-{N-[1-(S)-3-Methoxymethoxypheynl)-2-(3-(S)-methoxymethoxypyrrolidin-1-yl)-ethyl]-N-methylamino}benzoic Acid This was prepared from methyl 4-{N-[1-(S)-(3-methoxymethoxyphenyl)-2-(3-(S)-methoxymethoxypyrrolidin-1-yl)-ethyl]-N-methylamino}benzoate in 100% yield according to a procedure similar to that described in Example 1 (ii).

$^1$H NMR (270 MHz, CDCl)) δ 7.88 (2H, d, J=8.8 Hz), 7.30–7.12 (1H, m), 6.98–6.84 (3H, m), 6.68 (2H, d, J=8.8 Hz), 5.15–5.05 (1H, m), 5.10 (2H, s), 4.55 (1H, d, J=6.6 Hz), 4.51 (1H, d, J=7.0 Hz), 4.18–4.08 (1H, m), 3.42 (3H, s), 3.25 (3H, s), 3.10–2.92 (2H, m), 2.85 (1H, dd, J=6.4, 9.9 Hz), 2.74 (3H, s), 2.70–2.53 (3H, m), 2.10–1.93 (1H, m), 1.80–1.65 (1H, m).

(iii) 4-{N-[1-(S)-(3-Methoxymethoxyphenyl)-2-(3-(S)-methoxymethoxypyrrolidin-1-yl)-ethyl]-N-methylamino}-N'-propylbenzamide This was prepared from 4-{N-[1-(S)-(3-methoxymethoxyphenyl)-2-(3-(S)-methoxymethoxypyrrolidin-1-yl)-ethyl]-N-methylamino}benzoic acid and n-propylamine in 80% yield according to a procedure similar to that described in Example 1 (iii).

$^1$H NMR (270 MHz, CDCl$_3$) δ 7.65 (2H, d, J=9.2 Hz), 7.28–7.18 (1H, m), 6.98–6.88 (3H, m), 6.76 (2H, d, J=8.8 Hz), 6.05–5.90 (1H, m), 5.14 (2H, s), 5.08 (1H, dd, J=7.0, 7.7 Hz), 4.59 (1H, d, J=6.6 Hz), 4.55 (1H, d, J=7.0 Hz), 4.22–4.12 (1H, m), 3.46 (3H, s), 3.45–3.35 (2H, m), 3.30 (3H, s), 3.03 (2H, d, J=7.7 Hz), 2.86 (3H, s), 2.85–2.80 (1H, m), 2.75–2.50 (3H, m), 2.12–1.95 (1H, m), 1.85–1.52 (3H, m), 0.97 (3H, t, J=7.3 Hz).

Example 34

Preparation of 4-{N-[1-(S)-(3-Hydroxyphenyl)-2-(3-(S)-hydroxyyrrolidin-1-yl)-ethyl]-N-methylamino}-1-N'-propylbenzamide This was prepared from 4-{N-[1-(S)-(3-methoxymethoxyphenyl)-2-(3-(S)-methoxymethoxypyrrolidin-1-yl)-ethyl]-N-methylamimo}-N'-propylbenzamide in 97% yield according to a procedure similar to that described in Example 2.

$^1$H NMR (270 MHz, free amine, CDCl$_3$-DMSO-d6) δ 8.85 (1H, br.s), 7.69 (2H, d, J=9.2 Hz), 7.11 (1H, t, J=7.7 Hz), 6.98–6.90 (1H, m), 6.82–6.68 (5H, m), 5.06 (1H, dd, J=6.2, 8.4 Hz), 4.30–4.18 (1H, m), 3.67 (1H, br.s), 3.40–3.30 (2H, m), 3.15–2.95 (2H, m), 2.86 (3H, s), 2.85–2.67 (2H, m), 2.63–2.56 (1H, m), 2.55–2.43 (1H, m), 2.15–1.98 (1H, m), 1.70–1.52 (3H, m), 0.96 (3H, t, J=7.3 Hz). HCl salt: amorphous solid. IR(KBr):3350, 1610 cm$^{-1}$. MS m/z: 397 (M$^+$). Anal. Calcd for C$_{23}$H$_{31}$N$_3$O$_3$.HCl.2.3H$_2$O. C, 58.11; H, 7.76; N, 8.84; Found: C,57.82; H,8.06; N, 9.24.

Example 35

Preparation of 4-{N-[2-(3-(S)-Hydroxypyrrolidin-1-yl)-1-(S)-(3-methoxyphenyl)-ethyl]-N-methylamino}-N'-propylbenzamide To a solution of 4-{N-[1-(S)-(3-hydroxyphenyl)-2-(3-(S)-hydroxypyrrolidin-1-yl)-ethyl]-N-methylamino}-N'- propylbenzamide (100 mg, 0.252 mmol) in MeOH (0.1 ml)-CH₃CN (0.9 ml) was added N,N-diisopropylethylamine (0.0641 ml, 0.353 mmol) and 10%-trimethylsilyl-diazomethane in CH₂Cl₂ (0.6 ml) at room temperature. After stirring for 22 h at room temperature, 25%-NH₄OH was added to the mixture and extracted with CH₂Cl₂. The extract was washed with brine, dried (Na₂SO₄) and concentrated to give brown oil, which was purified by column chromatography (silica gel 5 g, CH₂Cl₂/MeOH: 30/1–10/1) to afford 55.2 mg (53%) of white amorphous.

$^1$H NMR (270 MHz, free amine, CDCl₃) δ 7.65 (2H, d, J=8.8 Hz), 7.24 (1H, t, J=7.7 Hz), 6.90–6.77 (5H, m), 6.05–5.90 (1H, m), 5.10 (1H, dd, J=5.9, 8.8 Hz), 4.25–4.18 (1H, m), 3.77 (3H, s), 3.45–3.35 (2H, m), 3.11 (1H, dd, J=9.2, 12.8 Hz), 3.01 (1H, dd, J=5.9, 12.8 Hz), 2.95–2.80 (1H, m), 2.84 (3H, s), 2.72 (1H, d, J=9.5 Hz), 2.56 (1H, dd, J=4.8, 9.5 Hz), 2.38–2.25 (1H, m), 2.16–2.00 (1H, m), 1.85–1.55 (4H, m), 0.97 (3H, t, J=7.7 Hz). HCl salt: amorphous solid. IR(neat, free amine): 3350, 1610 cm$^{-1}$. MS m/z: 412(M+H)⁺. Anal. Calcd for C₂₄H₃₃N₃O₃.HCl.0.5H₂O: C, 63.08; H, 7.72; N, 9.19; Found: C, 62.89; H, 7.77; N, 9.25.

Example 36

Preparation of 4-{N-[1-(S)-(3-t-Butoxycarbonylmethoxyphenyl)-2-(3-(S)-hydroxypyrrolidin-1-yl)-ethyl]-N-methylamino}-N'-propylbenzamide A mixture of 4-{N-[1-(S)-(3-hydroxyphenyl)-2-(3-(S)-hydroxypyrrolidin-1-yl)-ethyl]-N-methylamino}-N'-propylbenzamide (100 mg, 0.252 mmol), 1-butyl bromoacetate (0.0409 ml, 0.277 mmol) and K₂CO₃ (38.3 mg, 0.277 mmol) in DMF (1 ml) was stirred at room temperature for 2 h. H₂O was added to the mixture and extracted with AcOEt/toluene=2/1. The extract was washed with water, brine, dried (Na₂SO₄) and concentrated to give pale brown amorphous, which was purified by column chromato-graphy (silica gel 6 g, CH₂Cl₂/MeOH: 30/1–10/1) to afford 80.1 mg (62%) of white amorphous.

$^1$H NMR (270 MHz, CDCl₃) δ 7.65 (2H, d, J=9.2 Hz), 7.23 (1H, t, J=7.7 Hz), 6.94–6.86 (2H, m), 6.82–6.72 (3H, m), 6.05–5.90 (1H, m), 5.09 (1H, dd, J=6.2, 8.8 Hz), 4.48 (2H, s), 4.25–4.18 (1H, m), 3.45–3.35 (2H, m), 3.09 (1H, dd, J=9.2, 12.8 Hz), 3.00 (1H, dd, J=5.9, 12.8 Hz), 2.95–2.80 (1H, m), 2.83 (3H, s), 2.71 (1H, d, J=9.5 Hz), 2.54 (1H, dd, J=4.8, 9.5 Hz), 2.38–2.25 (1H, m), 2.16–2.00 (1H, m), 1.85–1.50 (4H, m), 1.46 (9H, s), 0.98 (3H, t, J=7.3 Hz).

Example 37

Preparation of 4-{N-[1-(S)-(3-Carboxymethoxyphenyl)-2-(3-(S)-hydroxypyrrolidin-1-yl)-ethyl]-N-methylamino}-N-'propylbenzamide A solution of 4-{N-[1-(S)-(3-t-butoxycarbonylmethoxyphenyl)-2-(3-(S)-hydroxypyrrolidin-1-yl)-ethyl]-N-methylamino}-N'-propylbenzamide (80.1 mg, 0.157 mmol) in trifluoroacetic acid (1 ml) and CH₂Cl₂ (0.5 ml) was stirred at room temperature for 1.5 h. The solvent was evaporated. The residue was dissolved in CH₂Cl₂ and 1.0M hydrogen chloride solution in diethyl ether (1 ml) was added. The white powder was collected and washed with Et₂O and dried under reduced pressure for 6.5 h at 45° C. to afford 86.2 mg (quant) of white powder. HCl salt: white powder.

$^1$H NMR (270 MHz, CDCl₃-DMSO-d6) δ 12.49 (1H, br. s), 7.79 (2H, d, J=8.4 Hz), 7.42 (1H, br. s), 7.23 (1H, t, J=7.7 Hz), 7.07 (2H, d, J=8.4 Hz), 6.85–6.76 (3H, m), 5.95–5.80 (1H, m), 4.53 (2H, s), 4.50–4.40 (1H, m), 4.00–3.70 (4H, m), 3.50–2.50 (3H, m), 2.80 (3H, s), 2.50–2.00 (2H, m), 1.75–1.55 (4H, m), 0.96 (3H, t, J=7.3 Hz). IR(KBr): 3400, 1730, 1610 cm$^{-1}$. MS m/z: 456(M+H)⁺. mp. 108–110° C. Anal. Calcd for C₂₅H₃₃N₃O₅.HCl.3.5H₂O: C, 54.10; H, 7.45; N, 7.57; Found: C, 54.07; H, 7.49; N, 7.39.

Example 38

Preparation of 4-{N-[1-(S)-Phenyl-2-(pyrrolidin-1-yl)ethyl]-N-methylamino}-N'-propylbenzamide (i) Methyl 4-{N-[1-(S)-phenyl-2-(pyrrolidin-1-yl)ethyl]-N-methylamino}benzoate This was prepared from the mixture of 2-(R)-phenyl-2-(pyrrolidin-1-yl)ethanol and 1-(S)-phenyl-2-(pyrrolidin-1-yl)ethanol and methyl 4-methylaminobenzoate in 52% yield according to a procedure similar to that described in Example 1 (i).

$^1$H NMR (270 MHz, CDCl₃) δ 7.88 (2H, d, J=9.2 Hz), 7.38–7.20 (5H, m), 6.78 (2H,d, J=9.2 Hz), 5.17 (1H, t, J=7.3 Hz), 3.84 (3H, s), 3.04 (2H, d, J=7.3 Hz), 2.86 (3H, s), 2.65–2.45 (4H, m), 1.80–1.65 (4H, m).

(ii) 4-{N-[1-(S)-Phenyl-2-(pyrrolidin-1-yl)ethyl]-N-methylamino}benzoic Acid

This was prepared from methyl 4-{N-[1-(S)-phenyl-2-(pyrrolidin-1-yl)ethyl]-N-methylamaino}benzoate in 100% yield according to a procedure similar to that described in Example 1 (ii).

$^1$H NMR (270 MHz, CDCl₃-DMSO-d6) δ 7.92 (2H, d, J=8.8 Hz), 7.38–7.20 (5H, m), 7.02 (2H, d, J=8.8 Hz), 5.80 (1H, br.s), 4.00–3.00 (7H, m), 2.85 (3H, s), 2.20–1.90 (4H, m).

(iii) 4-{N-[1-(S)-Phenyl-2-(pyrrolidin-1-yl)ethyl]-N-methylamino}-N'-propylbenzamide This was prepared from 4-{N-[1-(S)-phenyl-2-(pyrrolidin-1-yl)ethyl]-N-methylamino}benzoic acid and n-propylamine in 56% yield according to a procedure similar to that described in Example 1 (iii).

$^1$H NMR (270 MHz, free amine CDCl₃) δ 7.65 (2H, d, J=8.8 Hz), 7.36–7.20 (5H, m), 6.79 (2H, d, J=8.8 Hz), 6.05–5.90 (1H, m), 5.14 (1H, t, J=7.0 Hz), 3.45–3.35 (2H, m), 3.04 (2H, d, J=7.0 Hz), 2.84 (3H, s), 2.65–2.45 (4H, m), 1.75–1.50 (6H, m) 0.97 (3H, t, J=7.3 Hz). HCl salt: amorphous solid. IR(KBr): 1610 cm$^{-1}$. MS m/z: 366(M+H)⁺. Anal. Calcd for C₂₃H₃₁N₃O.HCl.0.5H₂O: C, 67.22; H, 8.09; N, 10.22; Found: C, 67.48; H, 8.37; N, 10.32.

Example 39

Preparation of 4-{N-[2-(3-(S)-Hydroxypyrrolidin-1-yl)-1-(S)-phenylethyl]-N-methylamino}-N'-propylphthalimide This was prepared from 2-(R)-phenyl-2-(3-(S)-tetrahydropyran-2-yloxypyrrolidin-1-yl)ethanol and 1-(S)-phenyl-2-(3-(S)-tetrahydropyran-2-yloxypyrrolidin-1-yl) ethanol and 4-methylamino-N'-propylphthalinide in 16% over all yield according to a procedure similar to that described in Example 1 (i) and 2.

$^1$H NMR (270 MHz, free amine, CDCl₃) δ 7.63 (1H, d, J=8.4 Hz), 7.38–7.22 (6H, m), 6.94 (1H, dd, J=2.6, 8.4 Hz), 5.19 (1H, dd, J=5.9, 9.5 Hz), 4.30–4.20 (1H, m), 3.59 (2H, t, J=7.3 Hz), 3.18 (1H, dd, J=9.5, 13.2 Hz), 3.03 (1H, dd, J=5.5, 12.8 Hz), 2.95 (3H, s), 2.95–2.85 (1H, m), 2.71 (1H, d, J=9.2 Hz), 2.61 (1H, dd, J=4.8, 9.5 Hz), 2.37 (1H, ddd, J=5.9, 8.8, 8.8 Hz), 2.20–2.05 (1H, m), 1.75–1.60 (4H,m), 0.93 (3H, t, J=7.3 Hz); HCl salt: amorphous solid. IR(KBr):

3400, 1760, 1700, 1620 cm$^{-1}$. Anal. Calcd for C$_{24}$H$_{29}$N$_3$O$_3$.HCl.0.5H$_2$O: C, 63.64; H, 6.90; N, 9.28; Found: C,63.99; H, 7.18; N, 9.00.

Example 40

Preparation of 5-{N-[2-(3-(S)-Methoxymethoxypyrrolidin-1-yl)-1-(S)-phenylethyl]-N-methylamino}-N'-propyl-2-thiophenecarboxamide This was prepared from 2-(3-(S)-methoxymethoxypyrrolidin-1-yl)-1-(S)-phenylethanol and 2-(3-(S)-methoxymethoxypyrrolidin-1-yl)-2-(R)-phenylethanol and 5-methylamino-N'-propyl-2-thiophenecarboxamide in 49% yield according to a procedure similar to that described in Example 1 (i).

$^1$H NMR (270 MHz, CDCl$_3$) δ 7.35–7.25 (5H, m), 7.18 (1H, d, J=4.4 Hz), 5.83 (1H, d, J=4.0 Hz), 5.68–5.60 (1H, m), 4.86 (1H, dd, J=7.0, 7.7 Hz), 4.62 (1H, d, J=7.0 Hz), 4.58 (1H, d, J=7.0 Hz), 4.25–4.15 (1H, m), 3.40–3.30 (2H, m), 3.32 (3H, s), 3.13–3.00 (2H, m), 2.94 (1H, dd, J=6.2, 9.9 Hz), 2.83 (3H, s), 2.80–2.70 (1H, m), 2.67–2.55 (2H, m), 2.15–2.00 (1H, m), 1.87–1.73 (1H, m), 1.70–1.50 (2H, m), 0.95 (3H, t, J=7.7 Hz).

Example 41

Preparation of 5-{N-[2-(3-(S)-Hydroxypyrrolidin-1-yl)-1-(S)-phenylethyl]-N-methylamino}-N'-propyl-2-thiophenecarboxamide This was prepared from 5-{N-[2-(3-(S)-methoxymethoxypyrrolidin-1-yl)-1-(S)-phenylethyl]-N-methylamino}-N'-propyl-2-thiophenecarboxamide in 78% yield according to a procedure similar to that described in Example 2.

$^1$H NMR (270 MHz, free amine, CDCl$_3$) δ 7.38–7.24 (5H, m), 7.18 (1H, d, J=4.0 Hz), 5.84 (1H, d, J=4.4 Hz), 5.70–5.60 (1H, m), 4.88 (1H, dd, J=6.0, 9.0 Hz), 4.30–4.22 (1H, m), 3.40–3.30 (2H, m), 3.15 (1H, dd, J=9.2, 12.8 Hz), 3.07–2.95 (2H, m), 2.81 (3H, s), 2.75 (1H, d, J=9.5 Hz), 2.63 (1H, dd, J=4.8, 9.5 Hz), 2.42–2.30 (1H, m), 2.22–2.05 (1H,m), 1.80–1.50 (4H, m), 0.96 (3H, t, J=7.7 Hz). Fumaric acid salt: amorphous solid. IR(KBr): 3300, 1610 cm$^{-1}$. MS m/z=388(M+H)$^+$. Anal. Calcd for C$_{21}$H$_{29}$N$_3$O$_2$S.C$_4$H$_4$O$_4$.0.5H$_2$O.CH$_4$O: C, 57.34; H, 7.03; N, 7.71; Found: C,57.37; H,7.31; N, 7.79.

Example 42

Preparation of 4-{N-[2-(3-(S)-Methoxymethoxypyrrolidin-1-yl)-1-(S)-phenylethyl]amino}-N'-propylbenzamide (i) Methyl 4-{N-[2-(3-(S)-methoxymethoxypyrrolidin-1-yl)-1-(S)-phenylethyl]amino}benzoate This was prepared from 2-(3-(S)-methoxymethoxypyrrolidin-1-yl)-1-(S)-phenylethanol and 2-(3-(S)-methoxymethoxypyrrolidin-1-yl)-2-(R)-phenylethanol and methyl 4-aminobenzoate in 69% yield according to a procedure similar to that described in Example 1 (i).

$^1$H NMR (270 MHz, CDCl$_3$) δ 7.75 (2H, d, J=8.8 Hz), 7.37–7.27 (5H, m), 6.47 (2H, d, J=8.8 Hz), 5.56 (1H, br. s), 4.65 (1H, d, J=6.6 Hz), 4.61 (1H, d, J=7.0 Hz), 4.35–4.28 (1H,m), 4.26–4.23 (1H, m), 3.80 (3H, s), 3.36 (3H, s), 2.90–2.76 (3H, m), 2.62–2.51 (2H, m), 2.48–2.42 (1H, m), 2.18–2.10 (1H, m), 1.84–1.82 (1H, m).

(ii) 4-{N-[2-(3-(S)-Methoxymethoxypyrrolidin-1-yl)-1-(S)-phenylethyl]amino}benzoic Acid This was prepared from methyl 4-{N-[2-(3-(S)-methoxymethoxypyrrolidin-1-yl)-1-(S)-phenylethyl]amino}benzoate in 100% yield according to a procedure similar to that described in Example 1 (ii).

$^1$H NMR (270 MHz, CDCl$_3$) δ 7.72 (2H, d, J=8.4 Hz), 7.36–7.23 (5H, m), 6.42 (2H, d, J=8.4 Hz), 5.80 (1H, br. s), 4.69–4.65 (1H, m), 4.63 (1H, d, J=7.0 Hz), 4.60 (1H, d, J=7.0 Hz), 4.39–4.37 (1H, m), 4.32–4.22 (1H,m), 3.34 (3H, s), 3.00–2.82 (3H, m), 2.66–2.48 (3H, m), 2.17–2.10 (1H, m), 1.95–1.78 (1H, m).

(iii) 4-{N-[2-(3-(S)-Methoxymethoxypyrrolidin-1-yl)-1-(S)-phenylethyl]amino}-N'-propylbenzamide This was prepared from 4-{N-[2-(3-(S)-methoxymethoxypyrrolidin-1-yl)-1-(S)-phenylethyl]amino}benzoic acid and n-propylamine in 62% yield according to a procedure sminilar to that described in Example 1 (iii).

$^1$H NMR (270 MHz, CDCl$_3$) δ 7.49 (2H, d, J=8.5 Hz), 7.38–7.24 (5H, m), 6.48 (2H, d, J=8.8 Hz), 5.95–5.80 (1H, m), 5.46 (1H, br. s), 4.65 (1H, d, J=7.0 Hz), 4.61 (1H, d, J=7.0 Hz), 4.32–4.23 (2H,m), 3.36 (3H, s), 3.38–3.31 (2H, m), 2.90–2.76 (3H, m), 2.59 (1H, dd, J=3.9, 10.8 Hz), 2.53–2.42 (2H, m), 2.18–2.11 (1H, m), 1.83–1.82 (1H, m), 1.60–1.50 (2H, m), 0.93 (3H, t, J=7.3 Hz).

Example 43

Preparation of 4-{N-[2-(3-(S)-Hydroxypyrrolidin-1-yl)-1-(S)-phenylethyl]amino}-N'-propylbenzamide This was prepared from 4-{N-[2-(3-(S)-methoxymethoxypyrrolidin-1-yl)-1-(S)-phenylethyl]amino}-N'-propylbenzamide in 67% yield according to a procedure similar to that described in Example 2.

$^1$H NMR (270 MHz, free amine, CDCl$_3$) δ 7.50 (2H, d, J=8.8 Hz), 7.38–7.22 (5H, m), 6.48 (2H, d, J=8.8 Hz), 5.95–5.80 (1H, m), 5.39 (1H, br. s), 4.39–4.29 (2H,m), 3.40–3.28 (2H, m), 2.99–2.84 (2H, m), 2.73–2.53 (3H,m), 2.40–2.31 (1H, m), 2.26–2.13 (1H, m), 1.90–1.67 (2H, m), 1.65–1.50 (2H, m), 0.94 (3H, t, J=7.3 Hz). HCl salt: amorphous solid. IR(KBr): 3350, 1610 cm$^{-1}$. Anal. Calcd for C$_{22}$H$_{29}$N$_3$O$_2$.HCl.1.1H$_2$O: C, 62.44; H, 8.05; N, 9.72; Found: C,62.36; H,7.66; N, 9.92.

Example 44

Preparation of 4-{N-[1-(S)-(3-Chlorophenyl)-2-(3-(S)-methoxymethoxypyrrolidin-1-yl)-ethyl]-N-methylamino}-N'-propylbenzamide (i) Methyl 4-{N-[1-(S)-(3-chlorophenyl)-2-(3-(S)-methoxymethoxypyrrolidin-1-yl)-ethyl]-N-methylamino}benzoate This was prepared from the nixture of 2-(R)-(3-chlorophenyl)-2-(3-(S)-methoxymethoxypyrrolidin-1-yl) ethanol and 1-(S)-(3-chlorophenyl)-2-(3-(S)-methoxymethoxypyrrolidin-1-yl)ethanol and methyl 4-methylaminobenzoate in 66% yield according to a procedure similar to that described in Example 1 (i).

$^1$H NMR (270 MHz, CDCl$_3$) δ 7.90 (2H, d, J=8.8 Hz), 7.30–7.14 (4H, m), 6.77 (2H, d, J=9.2 Hz), 5.11 (1H, dd, J=7.0, 7.7 Hz), 4.60 (1H, d, J=7.0 Hz), 4.55 (1H, d, J=7.0 Hz), 4.22–4.13 (1H, m), 3.86 (3H, s), 3.30 (3H, s), 3.12–2.94 (2H, m), 2.90–2.78 (1H, m), 2.87 (3H, s), 2.76–2.52 (3H, m), 2.15–1.98 (1H, m), 1.85–1.70 (1H, m).

(ii) 4-{N-[1-(S)-(3-Chlorophenyl)-2-(3-(S)-methoxymethoxypyrrolidin-1-yl)-ethyl]-N-methylamino}benzoic Acid This was prepared from methyl 4-{N-[1-(S)-(3-chlorophenyl)-2-(3-(S)-methoxymethoxypyrrolidin-1-yl)- ethyl]-N-methylamino}benzoate in 96% yield according to a procedure similar to that described in Example 1 (ii).

$^1$H NMR (270 MHz, CDCl$_3$) δ 7.93 (2H, d, J=9.2 Hz), 7.32–7.10 (4H, m), 6.82 (2H, d, J=9.2 Hz), 5.40–5.25 (1H,m), 4.62 (1H, d, J=7.0 Hz), 4.58 (1H, d, J=7.0 Hz), 4.30–4.18 (1H, m), 3.40–3.00 (3H, m), 3.31 (3H, s), 2.95–2.65(3H, m), 2.88 (3H, s), 2.20–2.00 (1H, m), 1.95–1.80 (1H, m).

(iii) 4-{N-[1-(S)-(3-Chlorophenyl)-2-(3-(S)-methoxymethoxypyrrolidin-1-yl)-ethyl]-N-methylamino}-N'-propylbenzamide This was prepared from 4-{N-[1-(S)-(3-chlorophenyl)-2-(3-(S)-methoxymethoxypyrrolidin-1-yl)-ethyl]-N-methylamino}benzoic acid and n-propylamine in 77% yield according to a procedure similar to that described in Example 1 (iii).

$^1$H NMR (270 MHz, CDCl$_3$) δ 7.66(2H, d, J=9.2 Hz), 7.30–7.13 (4H, m), 6.78 (2H, d, J=9.2 Hz), 6.02–5.92 (1H, m), 5.07 (1H, dd, J=6.6, 7.7 Hz), 4.60 (1H, d, J=7.0 Hz), 4.55 (1H, d, J=7.0 Hz), 4.25–4.12 (1H, m), 3.45–3.35 (2H, m), 3.30 (3H, s), 3.12–2.93 (2H, m), 2.90–2.78 (1H, m), 2.85 (3H, s), 2.75–2.52 (3H, m), 2.13–1.97 (1H, m), 1.85–170 (1H, m), 1.69–1.54 (2H, m), 0.98(3H, t, J=7.3 Hz).

Example 45

Preparation of 4-{N-[1-(S)-(3-Chlorophenyl)-2-(3-(S)-hydroxypyrrolidin-1-yl)-ethyl]-N-methylamino}-N'-propylbenzamide This was prepared from 4-{N-[(S)-3-chlorophenyl)-2-(3-(S)-methoxymethoxypyrrolidin-1-yl)-ethyl]-N-methylamino}-N'-propylbenzamide in 83% yield according to a procedure similar to that described in Example 2.

$^1$H NMR (270 MHz, free amine, CDCl$_3$) δ 7.67 (2H, d, J=9.2 Hz), 7.30–7.14 (4H, m), 6.79 (2H, d, J=8.8 Hz), 6.03–5.94 (1H, m), 5.09 (1H, dd, J=6.2, 8.8 Hz), 4.27–4.18 (1H, m), 3.45–3.35 (2H, m), 3.09 (1H, dd, J=8.8. 12.8 Hz), 3.01 (1H, dd, J=6.2, 12.8 Hz), 2.93–2.80 (1H, m), 2.84 (3H, s), 2.72 (1H, d, J=9.9 Hz), 2.57 (1H, dd, J=5.0, 9.7 Hz), 2.38–2.27 (1H, m), 2.17–2.02 (1H, m), 1.80–1.55 (4H, m), 0.98 (3H, t, J=7.3 Hz). Fumaric acid salt: amorphous solid. IR(KBr): 3350, 1610 cm$^{-1}$. MS m/z: 416(M+H)$^+$;

Example 46

Preparation of 4-{N-[2-(3-(S)-Fluoropyrrolidin-1-yl)-1-(S)-phenylethyl]-N-methlamino}-N'-propylbenzamide (i) Methyl 4-{N-[2-(3-(S)-fluoropyrrolidin-1-yl)-1-(S)-phenylethyl]-N-methylamino}benzoate This was prepared from 2-(3-(S)-fluoropyrrolidin-1-yl)-1-(S)-phenylethanol and 2-(3-(S)-fluoropyrrolidin-1-yl)-2-(R)-phenylethanol and methyl 4-methylaminobenzoate in 54% yield according to a procedure similar to that described in Example 1 (i).

$^1$H NMR (270 MHz, CDCl$_3$) δ 7.89 (2H, d, J=9.2 Hz), 7.38–7.22 (5H, m), 6.78 (2H, d, J=9.2 Hz), 5.25–4.95 (1H, m), 5.14 (1H, dd, J=6.6, 8.8 Hz), 3.84 (3H, s), 3.18–3.00 (2H, m), 2.95–2.75 (3H, m), 2.89 (3H, s), 2.60–2.50 (1H, m), 2.15–1.85 (2H, m).

(ii) 4-{N-[2-(3-(S)-Fluoropyrolidin-1-yl)-1-(S)-phenylethyl]-N-methylamino}benzoic Acid This was prepared from methyl 4-{N-[2-(3-(S)-fluoropyrrolidin-1-yl)-1-(S)-phenylethyl]-N-methylamino}benzoate in 100% yield according to a procedure similar to that described in Example 1 (ii).

$^1$H NMR (270 MHz, CDCl$_3$) δ 7.92 (2H, d, J=8.8 Hz) 7.40–7.10 (5H, m), 6.83 (2H, d, J=8.8 Hz), 5.40–5.00 (2H, m), 3.40–3.15 (2H, m), 3.10–2.70 (4H, m), 2.90 (3H, s), 2.30–1.90 (2H, m).

(iii) 4-{N-[2-(3-(S)-Fluoropyrrolidin-1-yl)-1-(S)-phenylethyl]-N-methylamino}-N'-propylbenzamide This was prepared from 4-{N-[2-(3-(S)-fluoropyrrolidin-1-yl)-1-(S)-phenylethyl]-N-methylamino}benzoic acid and n-propylamine in 73% yield according to a procedure similar to that described in Example 1 (iii).

$^1$H NMR (270 MHz, free amine, CDCl$_3$) δ 7.65 (2H, d, J=8.8 Hz), 7.37–7.22 (5H, m), 6.79 (2H, d, J=8.8 Hz), 6.03–5.92 (1H, m), 5.25–4.95 (1H, m), 5.11 (1H, dd, J=6.2, 8.4 Hz), 3.45–3.35 (2H, m), 3.18–3.02 (2H, m), 2.95–2.72 (3H, m), 2.87 (3H, s), 2.63–2.50 (1H, m), 2.18–1.85 (2H, m), 1.72–1.54 (2H, m), 0.97 (3H, t, J=7.3 Hz); HCl salt: amorphous solid. IR(KBr): 1605 cm$^{-1}$. MS m/z 384(M+H)$^+$; Anal. Calcd for C$_{23}$H$_{30}$N$_3$OF.HCl.0.3H$_2$O.CH$_4$O: C, 63.02; H, 7.84; N, 9.19; Found: C, 62.69; H, 8.17; N, 9.57.

Example 47

Preparation of 4-{N-[2-(3-(S)-Methoxymethoxypyrrolidin-1-yl)-1-(R)-phenylethyl]-N-methylamino}-N'-propylbenzamide (i) Methyl 4-{N-[2-(3-(S)-methoxymethoxypyrrolidin-1-yl)-1-phenylethyl]-N-methylamino}benzoate This was prepared from 2-(3-(S)-methoxymethoxypyrrolidin-1-yl)-1-(R)-phenylethanol and 2-(3-(S)-methoxymethoxypyrrolidin-1-yl)-2-(S)-phenylethanol and methyl 4-methylaminobenzoate in 49% yield according to a procedure similar to that described in Example 1 (i).

$^1$H NMR (270 MHz, CDCl$_3$) δ 7.88 (2H, d, J=8.8 Hz), 7.34–7.23 (5H, m), 6.73 (2H, d, J=9.2 Hz), 5.17 (1H, dd, J=7.0, 7.7 Hz), 4.58 (1H, d, J=7.0 Hz), 4.53 (1H, d, J=6.6 Hz), 4.22–4.15 (1H, m), 3.85 (3H, s), 3.68–3.52 (1H, m), 3.28 (3H, s), 3.08–3.04 (2H, m), 2.86 (3H, s), 2.76–2.67 (1H, m), 2.62–2.51 (2H, m), 2.08–1.97 (1H, m), 1.83–1.72 (1H, m).

(ii) 4-{N-[2-(3-(S)-Methoxymethoxypyrrolidin-1-yl)-1-(R)-phenylethyl]-N-methylamino}benzoic Acid This was prepared from methyl 4-{N-[2-(3-(S)-methoxymethoxypyrrolidin-1-yl)-1-(R)-phenylethyl]-N-methylamino}benzoate in 100% yield according to a procedure similar to that described in Example 1 (ii).

$^1$H NMR (270 MHz, CDCl$_3$) δ 7.89 (2H, d, J=9.2 Hz), 7.33–7.18 (5H, m), 6.75 (2H, d, J=9.2 Hz), 5.15 (1H, dd, J=7.0, 7.3 Hz), 4.57 (1H, d, J=7.0 Hz), 4.52 (1H, d, J=7.0 Hz), 4.25–4.15 (1H, m), 3.33 (3H, s), 3.05 (1H, d, J=6.6 Hz), 2.88–2.84 (1H, m), 2.85(3H, s), 2.76–2.62 (1H, m), 2.50–2.61 (3H, m), 2.07–2.02 (1H, m), 1.78–1.73 (1H, m).

(iii) 4-{N-[2-(2-(S)-Methoxymethoxypyrrolidin-1-yl)-1-(R)-phenylethyl]-N-methylamino}-N'-propylbenzamide This was prepared from 4-{N-[2-(3-(S)-methoxymethoxypyrrolidin-1-yl)-1-(R)-phenylethyl]-N-methylammino}benzoic acid and n-propylamine in 60% yield according to a procedure similar to that described in Example 1 (iii).

$^1$H NMR (270 MHz, CDCl$_3$) δ 7.63 (2H, d, J=9.2 Hz), 7.34–7.24 (5H, m), 6.79 (2H, d, J=9.2 Hz), 5.98–5.82 (1H, m), 5.13 (1H, t, J=7.3 Hz), 4.58 (1H, d, J=6.6 Hz), 4.54 (1H, d, J=7.0 Hz), 4.26–4.13 (1H,m), 3.43–3.34 (2H, m), 3.29 (3H, s), 3.06 (2H, d, J=7.3 Hz), 2.91–2.88 (1H, m), 2.85 (3H, s), 2.73–2.67 (1H, m), 2.61–2.54 (2H, m), 2.11–1.98 (1H, m), 1.84–1.72 (1H, m), 1.65–1.57 (2H, m), 0.97 (3H, t, J=7.3 Hz).

Example 48

Preparation of 4-{N-[2-(3-(S)-Hydroxypyrrolidin-1-yl)-1-phenylethyl]-N-methylamino}-N'-propylbenzamide This was prepared from 4-{N-[2-(3-(S)-methoxymethoxypyrrolidin-1-yl)-1-(R)-phenylethyl]-N- methylamino}-N'-propylbenzamide in 15% yield according to a procedure similar to that described in Example 2.

$^1$H NMR (270 MHz, free amine, CDCl$_3$) δ 7.59 (2H, d, J=9.2 Hz), 7.28–7.16 (5H, m), 6.75 (2H, d, J=8.8 Hz), 6.07–5.94 (1H, m), 5.12 (1H, t, J=7.3 Hz), 4.18–4.13 (1H, m), 3.35–3.27 (2H, m), 3.03 (2H, d, J=7.8 Hz), 2.92–2.86 (1H, m), 2.73 (3H, s), 2.66 (1H, d, J=9.9 Hz), 2.50 (1H, dd, J=4.8, 9.7 Hz), 2.38–2.33 (1H, m), 2.09–1.96 (2H, m), 1.67–1.46 (3H, m), 0.90 (3H, t, J=7.3 Hz). IR(neat): 3350, 1610 cm$^{-1}$. HCl salt: amorphous solid. Anal. Calcd for C$_{23}$H$_{31}$N$_3$O$_2$.HCl.1.9H$_2$O: C, 61.52; H, 8.37; N, 9.20. Found: C, 61.33; H, 7.97; N, 9.33.

Example 49

Preparation of 4-{N-[2-(3-(S)-Methoxymethoxypyrrolidin-1-yl)-1-(S)-phenyethyl]-N-methylamino}-pyrrolidinebenzamide This was prepared from 4-{N-[2-(3-(S)-methoxymethoxypyrrolidin-1-yl)-1-(S)-phenylethyl]-N-methylamino}benzoic acid and pyrrolidine in 77% yield according to a procedure similar to that described in Example 1 (iii).

$^1$H NMR (270 MHz, CDCl$_3$) δ 7.47 (2H, d, J=8.8 Hz), 7.33–7.21 (5H, m), 6.77 (2H, d, J=8.8 Hz), 5.11 (1H, dd, J=6.6, 7.3 Hz), 4.60 (1H, d, J=7.0 Hz), 4.56 (1H, dd, J=7.0 Hz), 4.21–4.15 (1H, m), 3.62–3.52 (4H, m), 3.30 (3H, s), 3.12–2.97 (2H, m), 2.82 (3H, s), 2.75–2.54 (4H, m), 2.09–1.74 (6H, m).

Example 50

Preparation of 4-{N-[2-(3-(S)-Hydroxypyrrolidin-1-yl)-1-(S)-phenylethyl]-N-methylamino}-pyrrolidinebenzamide This was prepared from 4-{N-[2-(3-(S)-methoxymethoxypyrrolidin-1-yl)-1-(S)-phenylethyl]-N-methylamino}-pyrrolidinebenzamide in 51% yield according to a procedure similar to that described in Example 2.

$^1$H NMR (270 MHz, free amine, CDCl$_3$) δ 7.49 (2H, d, J=9.2 Hz), 7.46–7.23 (5H, m), 6.79 (2H, d, J=8.8 Hz), 5.14 (1H, dd, J=6.2, 8.8 Hz), 4.24–4.20 (1H, m), 3.68–3.52 (4H, m), 3.12 (1H, dd, J=8.8, 12.6 Hz), 3.03 (1H, dd, J=6.2, 12.8 Hz), 2.95–2.87 (1H, m), 2.81 (3H, s), 2.75 (1H, d, J=10.3 Hz), 2.55 (1H, dd, J=4.8, 9.5 Hz), 2.35–2.27 (1H, m), 2.17–2.03 (1H, m), 1.98–1.82 (6H, m); IR(neat): 3400, 1610 cm$^{-1}$. HCl salt: amorphous solid. Anal. Calcd for C$_{24}$H$_{31}$N$_3$O$_2$.HCl.2H$_2$O: C, 61.65; H, 8.08; N, 8.83; Found: C, 61.86; H, 7.79; N, 9.02.

Example 51

Preparation of 4-{N-[2-(3-(S)-tert-Butyldimethylsilyloxypyrrolidin-1-yl)-1-(S)-phenylethyl]-N-methylamino}-N'-ethoxybenzamide (i) Methyl 4-{N-[2-(3-(S)-hydroxypyrrolidin-1-yl)-1-(S)-phenylethyl]-N-methylamino}benzoate This was prepared from methyl 4-{N-[2-(3-(S)-methoxymethoxypyrrolidin-1-yl)-1-(S)-phenylethyl]-N-methylamino}benzoate in 100% yield according to the procedures similar to those described in Example 2.

$^1$H NMR (270 MHz, CDCl$_3$) δ 7.90(2H, d, J=9.2 Hz), 7.36–7.23(5H, m), 6.80(2H, d, J=9.2 Hz), 5.18(1H, dd, J=5.9, 9.0 Hz), 4.24–4.20(1H, m), 3.85(3H, s), 3.13(1H, dd, J=5.9, 12.8 Hz), 2.94–2.88(2H, m), 2.85(3H, s), 2.73(1H, d, J=9.9 Hz), 2.56(1H, dd, J=4.8, 9.5 Hz), 2.36–2.30(1H, m), 2.27–2.05(1H, m), 1.80–1.50(2H,m).

(ii) Methyl 4-{N-[2-(3-(S)-tert-butyldimethylsilyloxypyrrolidin-1-yl)-1-(S)-phenylethyl]-N-methylamino}benzoate To a stirred solution of methyl 4-{N-[2-(3-(S)-hydroxypyrrolidin-1-yl)-1-(S)-phenylethyl]-N-methylamino}benzoate (865 mg, 2.44 mmol) in DMF (10 ml) was added imidazole (1.54 g, 24.4 mmol) and tert-butyidimethylsilylchloride (1.83 g, 12.2 mmol) at 0° C. After 3 hr stirring, saturated NaHCO$_3$ aqueous solution was added to the reaction mixture and extracted with CH$_2$Cl$_2$. The extract was washed with water and brine. dried (Na$_2$SO$_4$), and concentrated to give brown oil, which was purified by column chromatography (silica gel; 40 g, CH$_2$Cl$_2$/MeOH: 100/1–50/1) to give 760 mg (66%) of title compound.

$^1$H NMR (270 MHz, CDCl$_3$) δ 7.79 (2H, d, J=9.2 Hz), 7.24–7.14(5H, m), 6.68(2H, d, J=9.2 Hz), 5.05(1H, dd, J=6.2, 7.3 Hz), 4.21–4.12(1H, m), 3.75(3H, s), 2.97–2.92 (2H, m), 2.82–2.76(1H, m), 2.75(3H, s), 2.58–2.53(2H, m), 2.27(1H, dd, J=4.4, 9.2 Hz), 1.93–1.86 (1H, m), 1.58–1.47 (1H,m), 0.74(9H, s), 0.01(6H, s).

(iii) 4-{N-[2-(3-(S)-tert-Butyldimethylsilyioxypyrrolidin-1-yl)-1-(S)-phenylethyl]-N-methylamino}benzoic Acid This was prepared from methyl 4-{N-[2-(3-(S)-tert-butyidimethylsilyloxypyrrolidin-1-yl)-1-(S)-phenylethyl]-N-methylamino}benzoate in 32% yield according to the procedures similar to those described in Example 1-(ii).

$^1$H NMR (270 MHz, CDCl$_3$) δ 7.90(2H, d, J=9.2 Hz), 7.32–7.23(5H, m), 6.80(2H, d, J=9.2 Hz), 5.29–5.26(1H,m), 4.32–4.25(1H, m), 3.26–3.12(2H, m), 3.12–3.06(1H, m), 2.85(3H, s), 2.73–2.65(2H, m), 2.46–2.41(1H, m), 2.07–2.00(1H, m), 1.71–1.62(1H, m), 0.84(9H, s), 0.01(6H, s).

(iv) 4-{N-[2-(3-(S)-tert-Butyldimethylsilyloxypyrrolidin-1-yl)-1-(S)-phenylethyl]-N-methylamino}-N'-ethoxybenzamide This was prepared from 4-{N-[2-(3-(S)-tert-butyldimethylsilyloxypyrrolidin-1-yl)-1-(S)-phenylethyl]-N-methylamino}benzoic acid and O-ethylhydroxylamine in 41% yield according to the procedures similar to those described in Example 1-(iii).

$^1$H NMR (270 MHz, CDCl$_3$) δ 8.39(1H, br.s), 7.62(2H, d, J=8.8 Hz), 7.34–7.24(5H, m), 6.78(2H, d, J=9.2 Hz), 5.11–5.09(1H,m), 4.32–4.23(1H, m), 4.07(2H, q, J=7.0 Hz), 3.06–3.02(1H, m), 2.92–2.86(1H, m), 2.84(3H, s), 2.68–2.63(2H, m), 2.38(1H, dd, J=4.4, 9.2 Hz), 2.03–1.96 (1H, m), 1.68–1.62(2H, m), 1.32(3H, t, J=7.0 Hz), 0.84(9H, s), 0.01(6H, s).

Example 52

Preparation of 4-{N-[2-(3-(S)-Hydroxypyrrolidin-1-yl)-1-(S)-phenylethyl]-N-methylamino}-N'-ethoxybenzamide To a stirred solution of 4-{N-[2-(3-(S)-tert-butyldimethylsilyloxypyrrolidin-1-yl)-1-(S)-phenylethyl]-N-methylamino}-N'-ethoxybenzamide (44.7 mg, 0.0901 mmol) in THF (1 ml) was added 1.0M solution of tetrabutylammonium fluoride in THF (0.273 ml. 0.273 mmol) at room temperature. After 18 hr surring, saturated NaHCO$_3$ aqueous solution was added to the reaction mixture and extracted with CH$_2$Cl$_2$. The extract was washed with water and brine, dried (Na$_2$SO$_4$), and concentrated to give brown oil, which was purified by column chromatography (silica gel; 20 g, CH$_2$Cl$_2$/MeOH: 25/1–10/1) to give 28.4 mg (82%) of title compound.

$^1$H NMR (270 MHz, free amine, CDCl$_3$) δ 8.60(1H, br.s), 7.64(2H, d, J=9.2 Hz), 7.36–7.24(5H, m), 6.80(2H, d, J=9.2

Hz), 5.16(1H,dd, J=5.9, 9.2 Hz), 4.24–4.20(1H, m), 4.06 (2H, q, J=7.0 Hz), 3.14(1H, dd, J=9.2, 13.2 Hz), 3.04(1H, dd, J=5.9, 12.0 Hz), 2.89–2.83(1H, m), 2.83(3H, s), 2.76 (1H, d, J=9.5 Hz), 2.57(1H, dd, J=4.8, 9.9 Hz), 2.38–2.29 (1H, m), 2.16–2.03(1H, m), 1.90–1.56(2H, m), 1.32(3H, t, J=7.0 Hz). HCl salt: amorphous solid. Anal. Calcd for $C_{22}H_{29}N_3O_3 \cdot HCl \cdot 0.7H_2O$: C, 58.04; H, 8.00; N, 8.46; Found: C, 58.26; H, 8.40; N, 8.58.

Example 53

Preparation of 4-{N-[2-(3-(S)-Methoxymethoxypyrrolidin-1-yl)-1-(S)-phenylethyl]-N-methylamino}-morpholinebenzamide This was prepared from 4-{N-[2-(3-(S)-methoxymethoxypyrrolidin-1-yl)-1-(S)-phenylethyl]-N-methylamino}benzoic acid and morpholine in 54% yield according to the procedures similar to those described in Example 1 (iii).

$^1$H NMR (270 MHz, CDCl$_3$) δ 7.32(2H, d, J=8.8 Hz), 7.29–7.28(5H, m), 6.78(2H, d, J=8.8 Hz), 5.10(1H, dd, J=7.0, 7.7 Hz), 4.60(1H, d, J=7.0 Hz), 4.55(1H, d, J=6.6 Hz), 4.22–4.13(1H, m), 3.68–3.67(8H, m), 3.30(3H, s), 3.07–3.02(2H, m), 2.90–2.80(1H, m), 2.84(3H, s), 2.75–2.57(3H, m), 2.07–2.02(1H, m), 1.81–1.72(1H, m).

Example 54

Preparation of 4-{N-[2-(3-(S)-Hydroxypyrrolidin-1-yl)-1-(S)-phenylethyl]-N-methylamino}-morpholinebenzamide This was prepared from 4-{N-[2-(3-(S)-methoxymethoxypyrrolidin-1-yl)-1-(S)-phenylethyl]-N-methylamino}-morpholinebenzamide in 76% yield according to the procedures similar to those described in Example 2.

$^1$H NMR (270 MHz, free amine, CDCl$_3$) δ 7.34(2H, d, J=9.2 Hz), 7.30–7.24(5H, m), 6.80(2H, d, J=8.8 Hz), 5.13 (1H, dd, J=6.6, 8.8 Hz), 4.27–4.21(1H, m), 3.81–3.58(8H, m), 3.16–2.96(2H, m), 2.92–2.87(1H, m), 2.82(3H, s), 2.75 (1H, d, J=9.2 Hz), 2.55(1H, dd, J=4.4, 9.5 Hz), 2.36–2.27 (1H, m), 2.12–2.09(1H, m), 1.75–1.60(2H, m); IR(neat): 3400, 1610 cm$^{-1}$. HCl salt: amorphous solid. MS m/z: 410(M+H)$^+$;

Example 55

Preparation of 4-{N-[2-(3-(S)-Methoxymethoxypyrrolidin-1-yl)-1-(S)-phenylethyl]-N-methylamino}-N'-(3-hydroxypropyl)benzamide This was prepared from 4-{N-[2-(3-(S)-methoxymethoxypyrrolidin-1-yl)- 1-(S)-phenylethyl]-N-methylamino}benzoic acid and 3-amino-1-propanol in 48% yield according to the procedures similar to those described in Example 1 (iii).

$^1$H NMR (270 MHz, CDCl$_3$) δ 7.66(2H, d, J=9.2 Hz), 7.40–7.20(5H, m), 6.80(2H, d, J=8.8 Hz), 6.40–6.30(1H, m), 5.14(1H, dd, J=7.0, 7.7 Hz), 4.60(1H, d, J=6.6 Hz), 4.55(1H, d, J=6.6 Hz), 4.25–4.13(1H, m), 3.73–3.55(4H, m), 3.30(3H, s), 3.13–3.00(2H, m), 2.90–2.80(1H, m), 2.86(3H, s), 2.78–2.52(3H, m), 2.13–1.98(1H, m), 1.81–1.45(4H, m).

Example 56

Preparation of 4-{N-[2-(3-(S)-Hydroxypyrrolidin-1-yl)-1-(S)-phenylethyl]-N-methylamino}-N'-(3-hydroxgroyl)benzamide This was prepared from 4-{N-[2-(3-(S)-methoxymethoxypyrrolidin-1-yl)-1-(S)-phenylethyl]-N-methylamino}-N'-(3-hydroxypropyl)benzamide in 82% yield according to the procedures similar to those described in Example 2.

$^1$H NMR (270 MHz, free amine, CDCl3) δ 7.66(2H, d, J=9.2 Hz), 7.35–7.26(5H, m), 6.81(2H, d, J=9.2 Hz), 6.42–6.33(1H, m), 5.15(1H, dd, J=5.9, 8.8 Hz), 4.27–4.17 (1H, m), 3.66(2H, t, J=5.5 Hz), 3.59(2H, t, J=5.9 Hz), 3.13(1H, dd, J=9.2, 12.8 Hz), 3.03(1h, dd, J=5.9, 12.8 Hz), 2.94–2.86(1H, m), 2.84(3H, s), 2.72(1H, d, J=9.5 Hz), 2.56(1H, dd, J=4.8, 9.9 Hz), 2.36–2.28(1H, m), 2.13–2.03 (1H, m), 1.79–1.61(5H, m); IR(neat): 3350, 1610 cm$^{-1}$. HCl salt: amorphous solid. MS m/z: 398(M+H)$^+$.

Example 57

Preparation of 4-{N-[2-(3-(S)-Methoxymethoxypyrrolidin-1-yl)-1-(S)-phenylethyl]-N-methylamino}-N'-(2-(R)-hydroxypropyl)benzamide This was prepared from 4-{N-[2-(3-(S)-methoxymethoxypyrrolidin-1-yl)-1-(S)-phenylethyl]-N-methylamino}benzoic acid and (R)-(−)-1-amino-2-propanol in 83% yield according to the procedures similar to those described in Example 1 (iii).

$^1$H NMR (270 MHz, CDCl$_3$) δ 7.67(2H, d, J=8.8 Hz), 7.40–7.20(5H, m), 6.80(2H, d, J=8.8 Hz), 6.50–6.40(1H, m), 5.14(1H, dd, J=7.0, 7.7 Hz), 4.59(1H, d, J=7.0 Hz), 4.55(1H, d, J=7.0 Hz), 4.23–4.13(1H, m), 4.07–3.95(1H, m), 3.66–3.55(1H, m), 3.40–3.20(1H, m), 3.30(3H, s), 3.13–3.00(2H, m), 2.90–2.80(1H, m), 2.85(3H, s), 2.76–2.52(3H, m), 2.13–1.98(1H, m), 1.85–1.45(2H, m), 1.23(3H, d, J=6.2 Hz).

Example 58

Preparation of 4-{N-[2-(3-(S)-Hydroxypyrrolidin-1-yl)-1-(S)-phenylethy]-N-methylamino}-N'-(2-(R)-hydroxypropyl)benzamide This was prepared from 4-{N-[2-(3-(S)-methoxymethoxypyrroildin-1-yl)-1-(S)-phenylethyl]-N-methylamino}-N'-(2-(R)-hydroxypropyl)benzamide in 84% yield according to the procedures similar to those descrbed in Example 2.

$^1$H NMR (270 MHz, free amine, CDCl$_3$) δ 7.68(2H, d, J=8.8 Hz), 7.40–7.20(5H, m), 6.82(2H, d, J=8.8 Hz), 6.50–6.38(1H, m), 5.16(1H, dd, J=5.9, 8.8 Hz), 4.28–4.18 (1H, m), 4.10–3.95(1H, m), 3.66–3.55(1H, m), 3.40–3.35 (1H, m), 3.16–3.00(2H, m), 2.95–2.80(1H, m), 2.84(3H, s), 2.74(1H, d, J=9.2 Hz), 2.56(1H, dd, J=4.4, 9.5 Hz), 2.40–2.25(1H, m), 2.17–2.00(1H, m), 1.90–1.40(3H, m), 1.24(3H, d, J=6.6 Hz); IR(neat): 3350, 1610 cm$^{-1}$. HCl salt: amorphous solid. MS m/z: 398(M+H)$^+$; Anal. Calcd for $C_{23}H_{31}N_3O_3 \cdot HCl \cdot 0.85CH_4O$: C, 62.11; H, 7.74; N, 9.11; Found: C, 62.50; H, 8.13; N, 9.37.

Example 59

Preparation of 4-{N-[2-(3-(S)-Methoxymethoxypyrrolidin-1-yl)-1-(S)-phenylethyl]-N-methylamino}-N'-isobutylbenzamide This was prepared from 4-{N-[2-(3-(S)-methoxymethoxypyrrolidin-1-yl)-1-(S)-phenylethyl]-N-methylamino}benzoic acid and isobutylamine in 72% yield according to the procedures similar to those described in Example 1 (iii).

$^1$H NMR (270 MHz, CDCl$_3$) δ 7.65(2H, d, J=8.8 Hz), 7.34–7.24(5H, m), 6.80(2H, d, J=8.8 Hz), 6.04–5.92(1H, m), 5.18–5.08(1H, m), 4.59(1H, d, J=7.0 Hz), 4.55(1H, d, J=6.6 Hz), 4.22–4.13(1H, m), 3.29(3H, s), 3.28–3.23(2H, m), 3.10–3.02(2H, m), 2.84–2.80(1H, m), 2.84(3H, s), 2.72–2.57(3H, m), 2.12–1.98(1H, m), 1.89–1.79(1H, m), 1.78–1.69(1H, m), 0.96(6H, d, J=6.6 Hz).

Example 60

Preparation of 4-{N-[2-(3-(S)-Hydroxypyrrolidin-1-yl)-1-(S)-phenylethyl]-N-methylamino}-N'-isobutylbenzamide This was prepared from 4-{N-[2-(3-(S)-methoxymethoxypyrrolidin-1-yl)-1-(S)-phenylethyl]-N-methylamino}-N'-isobutylbenzamide in 86% yield according to the procedures similar to those described in Example 2.

$^1$H NMR (270 MHz, free amine, CDCl$_3$) δ 7.66(2H, d, J=8.8 Hz), 7.35–7.26(5H, m), 6.81(2H, d, J=8.8 Hz), 6.06–5.96(1H, m), 5.15(1H, dd, J=5.9, 8.8 Hz), 4.26–4.18 (1H, m), 3.26(2H, t, J=6.2 Hz), 3.13(1H, dd, J=8.8, 12.8 Hz), 3.03(1H, dd, J=5.9, 12.8 Hz), 2.92–2.85(1H, m), 2.84(3H, s), 2.73(1H, d, J=9.5 Hz), 2.56(1H, dd, J=4.6, 9.7 Hz), 2.36–2.28(1H, m), 2.16–2.04(1H, m), 1.96–1.58(3H, m), 0.97(6H, d, J=7.0 Hz). IR(neat): 3350, 1610 cm$^{-1}$. HCl salt: amorphous solid. MS m/z: 396(M+H)$^+$; Anal. Calcd for C$_{24}$H$_{33}$N3O$_2$.HCl.0.5H$_2$O: C, 65.36; H, 8.00; N, 9.53; Found: C,65.58; H, 8.17; N,9.48.

Example 61

Preparation of 4-{N-[2-(3-(S)-Methoxymethoxypyrrolidin-1-yl)-1-(S)-phenlethyl]-N-methylamino}-N'-allylbenzamide This was prepared from 4-{N-[2-(3-(S)-methoxymethoxypyrrolidin-1-yl)- 1-(S)-phenylethyl]-N-methylamino}benzoic acid and allylamine in 33% yield according to the procedures similar to those described in Example 1 (iii).

$^1$H NMR (270 MHz, CDCl$_3$) δ 7.67(2H, d, J=8.8 Hz), 7.31–7.26(5H, m), 6.79(2H, d, J=9.2 Hz), 6.01–5.88(2H, m), 5.28–5.27(1H, m), 5.21–5.11(2H, m), 4.59(1H, d, J=7.0 Hz), 4.55(1H, d, J=6.6 Hz), 4.25–4.13(1H, m), 4.09–4.04(2H, m), 3.29(3H, s), 3.07–3.03(2H, m), 2.85–2.80(1H, m), 2.85(3H, s), 2.75–2.67(1H, m), 2.64–2.56(1H,m), 2.06–2.01(1H, m), 1.76–1.60(1H, m), 1.60–1.52(1H, m).

Example 62

Preparation of 4-{N-[2-(3-(S)-Hydroxypyrrolidin-1-yl)-1-(S)-phenylethyl]-N-methylamino}-N'-allylbenzamide This was prepared from 4-{N-[2-(3-(S)-methoxymethoxypyrrolidin-1-yl)-1-(S)-phenylethyl]-N-methylamino}-N'-allylbenzamide in 52% yield according to the procedures similar to those described in Example 2.

$^1$H NMR (270 MHz, free amine, CDCl$_3$) δ 7.68(2H, d, J=8.8 Hz), 7.35–7.26(5H, m), 6.81(2H, d, J=8.8 Hz), 6.01–5.89(2H, m), 5.28–5.12(3H, m), 4.27–4.19(1H, m), 4.09–4.05(2H, m), 3.13(1H, dd, J=9.2, 12.8 Hz), 3.03(1H, dd, J=5.9, 12.8 Hz), 2.92–2.86(1H, m), 2.84(3H, s), 2.73 (1H, d, J=9.2 Hz), 2.56(1H, dd, J=4.8, 9.5 Hz), 2.33–2.30 (1H,m), 2.27–2.08(1H, m), 1.67–1.48(2H, m). IR(neat): 3350, 1610 cm$^{-1}$. HCl salt: amorphous solid. MS m/z: 380(M+H)$^+$; Anal. Calcd for C$_{23}$H$_{29}$N$_3$O$_2$.HCl.0.1H$_2$O.CH$_4$O: C, 64.09; H, 7.66; N,9.34; Found: C,63.86; H, 7.85; N,9.32.

Example 63

Preparation of 4-{N-[2-(3-(S)-Methoxymethoxypyrrolidin-1-yl)-1-(S)-phenylethyl]-N-methylamino}-N'-cyclopropylbenzamide This was prepared from 4-{N-[2-(3-(S)-methoxymethoxypyrrolidin-1-yl)-1-(S)-phenylethyl]-N-methylamino}benzoic acid and cyclopropylamine in 48% yield according to the procedures similar to those described in Example 1 (iii).

$^1$H NMR (270 MHz, CDCl$_3$) δ 7.61(2H, d, J=8.8 Hz), 7.33–7.22(5H, m), 6.78(2H, d, J=8.8 Hz), 6.11–6.02(1H, m), 5.15–5.11(1H, m), 4.59(1H, d, J=6.6 Hz), 4.55(1H, d, J=6.6 Hz), 4.19–4.14(1H, m), 3.29(3H, s), 3.07–3.03(2H, m), 2.90–2.80(1H, m), 2.84(3H, s), 2.72–2.66(1H, m), 2.64–2.56(2H,m), 2.08–2.01(1H, m), 1.79–1.73(1H, m), 1.37–1.25(1H, m), 0.94–0.80(2H, m), 0.60–0.54(2H, m).

Example 64

Preparation of 4-{N-[2-(3-(S)-Hydroxypyrrolidin-1-yl)-1-(S)-phenylethyl]-N-methylamino}-N'-cyclopropylbenzamide This was prepared from 4-{N-[2-(3-(S)-methoxymethoxypyrrolidin-1-yl)-1-(S)-phenylethyl]-N-methylamino}-N'-cyclopropylbenzamide in 76% yield according to the procedures similar to those described in Example 2.

$^1$H NMR (270 MHz, free amine, CDCl$_3$) δ 7.63(2H, d, J=9.2 Hz), 7.35–7.23(5H, m), 6.79(2H, d, J=8.8 Hz), 6.12–6.04(1H, m), 5.15(1H, dd, J=5.9, 8.8 Hz), 4.24–4.19 (1H, m), 3.13(1H, dd, J=9.2, 12.8 Hz), 3.03(1H, dd, J=5.9, 10.3 Hz), 2.94–2.84(2H, m), 2.83(3H, s), 2.78(1H, d, J=9.5 Hz), 2.58–2.53(1H,m), 2.33–2.31(1H, m), 2.11–2.08 (1H, m), 1.68–1.61(2H, m), 0.87–0.80(2H, m), 0.60–0.54(2H, m). IR(neat): 3350, 1610 cm$^{-1}$. HCl salt: amorphous solid. MS m/z: 380(M+H)$^-$; Anal. Calcd for C$_{23}$H$_{29}$N$_3$O$_2$.HCl.0.8H$_2$O: C, 64.19; H, 7.40; N, 9.76; Found: C,64.04; H, 7.50; N,9.83.

Example 65

Preparation of 4-{N-[2-(3-(S)-Methoxymethoxypyrrolidin-1-yl)-1-(S)-phenylethyl]-N-methylamino}-N'-(S)-sec-butylbenzamide This was prepared from 4-{N-[2-(3-(S)-methoxymethoxypyrrolidin-1-yl)-1-(S)-phenylethyl]-N-methylamino}benzoic acid and (S)-sec-butylamine in 18% yield according to the procedures similar to those described in Example 1 (iii).

$^1$H NMR (270 MHz, CDCl$_3$) δ 7.65(2H, d, J=8.8 Hz), 7.40–7.20(5H, m), 6.79(2H, d, J=8.8 Hz), 5.74(1H, d, J=8.4 Hz), 5.13(1H, dd, J=6.6, 8.1 Hz), 4.59(1H, d, J=7.0 Hz), 4.55(1H, d, J=7.0 Hz), 4.25–4.05(2H, m), 3.30(3H, s), 3.15–2.95(2H, m), 2.90–2.80(1H, m), 2.85(3H, s), 2.76–2.55(3H, m), 2.13–1.98(1H, m), 1.85–1.70(1H, m), 1.65–1.50(2H, m), 1.20(3H, d, J=6.6 Hz), 0.95(3H, t, J=7.7 Hz).

Example 66

Preparation of 4-{N-[2-(3-(S)-Hydroxypyrrolidin-1-yl)-1-(S)-phenylethyl]-N-methylamino}-N'-(S)-sec-butylbenzamide This was prepared from 4-{ N-[2-(3-(S)-methoxymethoxypyrrolidin-1-yl)-1-(S)-phenylethyl]-N- methylamino}-N'-(S)-sec-butylbenzamide in 100% yield according to the procedures similar to those described in Example 2.

$^1$H NMR (270 MHz, free amine, CDCl$_3$) δ 7.65(2H, d, J=9.2 Hz), 7.40–7.20(5H, m), 6.80(2H, d, J=9.2 Hz), 5.76 (1H, d, J=8.4 Hz), 5.14(1H, dd, J=6.2, 8.8 Hz), 4.25–4.05 (2H, m), 3.17–2.98(2H, m), 2.95–2.78(1H, m), 2.83(3H, s), 2.72(1H, d, J=9.5 Hz), 2,57(1H, dd, J=4.8, 9.5 Hz), 2.40–2.28(1H, m), 2.20–1.95(2H, m), 1.70–1.50(3H, m), 1.20(3H, d, J=6.6 Hz), 0.95(3H, t, J=7.3 Hz). HCl salt: amorphous solid. MS m/z: 396(M+H)$^+$; Anal. Calcd for C$_{24}$H$_{33}$N$_3$O$_2$.HCl.0.3H$_2$O.CH$_4$O: C, 63.96; H, 8.29; N, 8.95; Found: C,64.14; H, 8.01; N,8.70.

Example 67

Preparation of 4-{N-[2-(3-(S)-Methoxymethoxypyrrolidin-1-yl)- 1-(S)-phenylethyl]-N-methylamino}-N'-(R)-sec-butylbenzamide This was prepared from 4-{N-[2-(3-(S)-methoxymethoxypyrrolidin-1-yl)-1-(S)-phenylethyl]-N-methylamino}benzoic acid and (R)-sec-butylamine in 18% yield according to the procedures similar to those described in Example 1 (iii).

$^1$H NMR (270 MHz, CDCl$_3$) δ 7.65(2H, d, J=8.8 Hz), 7.33–7.23(5H, m), 6.79(2H, d, J=9.2 Hz), 5.74(1H, d, J=8.1 Hz), 5.13(1H, dd, J=6.6, 7.7 Hz), 4.59(1H, d, J=6.6 Hz), 4.55(1H, d, J=6.6 Hz), 4.19–4.08(2H, m), 3.29(3H, s), 3.09–2.98(2H, m), 2.90–2.80(1H, m), 2.84(3H, s), 2.72–2.57(3H, m), 2.13–1.98(1H, m), 1.78–1.75(1H, m), 1.60–1.49(2H, m), 1.20(3H, d, J=6.6 Hz), 0.94(3H, t, J=7.7 Hz).

Example 68

Preparation of 4-{N-[2-(3-(S)-Hydroxypyrrolidin-1-yl)-1-(S)-phenylethyl]-N-methylamino}-N'-(R)-sec-butylbenzamide This was prepared from 4-{N-[2-(3-(S)-methoxymethoxypyrrolidin-1-yl)-1-(S)-phenylethyl]-N-methylamino}-N'-(R)-sec-butylbenzamide in 95% yield according to the procedures similar to those described in example 2.

$^1$H NMR (270 MHz, free amine, CDCl$_3$) δ 7.65(2H, d, J=8.8 Hz), 7.40–7.20(5H, m), 6.80(2H, d, J=8.8 Hz), 5.78 (1H, d, J=8.3 Hz), 5.14(1H, dd, J=5.9, 8.8 Hz), 4.25–4.03 (2H, m), 3.17–2.98(2H, m), 2.95–2.78(1H, m), 2.83(3H, s), 2.71(1H, d, J=9.5 Hz), 2.58(1H, dd, J=4.8, 9.5 Hz), 2.42–2.30(1H, m), 2.23(1H, br.s), 2.15–2.00(1H, m), 1.70–1.50(3H, m), 1.20(3H, d, J=6.6 Hz), 0.95(3H, J=7.3 Hz). HCl salt: amorphous solid. MS m/z: 396(+H)$^+$; Anal. Calcd for C$_{24}$H$_{33}$N$_3$O$_2$.HCl.0.4H$_2$O.CH$_4$O: C, 63.72; H, 8.30, N, 8.92; Found: C,63.96; H, 8.08; N,9.08.

Example 69

Preparation of 4-{N-[2-(3-(S)-Methoxymethoxypyrrolidin-1-yl)-1-(S)-phenylethyl]-N-methylamino}-N'-propargylbenzamide This was prepared from 4-{N-[2-(3-(S)-methoxymethoxypyrrolidin-1-yl)-1-(S)-phenylethyl]-N-methylamino}benzoic acid and propargylamine in 18% yield according to the procedures similar to those described in Example 1 (iii).

$^1$H NMR (270 MHz, CDCl$_3$) δ 7.65(2H, d, J=8.8 Hz), 7.34–7.24(5H, m), 6.80(2H, d, J=9.2 Hz), 6.12–6.03(1H, m), 5.14(1H, dd, J=6.6, 7.3 Hz), 4.59(1H, d, J=7.0Hz), 4.55(1H, d, J=7.0 Hz), 4.23(2H, q, J=2.6 Hz), 4.19–4.14(1H, m), 3.29(3H, s), 3.07–3.03(2H, m), 2.85–2.80(1H, m), 2.85(3H, s), 2.75–2.70(1H, m), 2.67–2.56(2H, m), 2.25(1H, t, J=2.6 Hz), 2.08–2.01(1H, m), 1.87–1.70(1H, m).

Example 70

Preparation of 4-{N-[2-(3-(S)-Hydroxypyrrolidin-1-yl)-1-(S)-phenylethyl]-N-methylamino}-N'-propargylbenzamide This was prepared from 4-{N-[2-(3-(S)-methoxymethoxypyrrolidin-1-yl)-1-(S)-phenylethyl]-N-methylamino}-N'-propargylbenzamide in 77% yield according to the procedures similar to those described in Example 2.

$^1$H NMR (270 MHz, free amine, CDCl$_3$) δ 7.67(2H, d, J=8.8 Hz), 7.35–7.24(5H, m), 6.81(2H, d, J=8.8 Hz), 6.13–6.03(1H, m), 5.16(1H, dd, J=5.9, 9.0 Hz), 4.24–4.21 (3H, m), 3.13(1H, dd, J=9.5, 12.8 Hz), 3.03(1H, dd, J=5,9, 12.8 Hz), 2.93–2.86(1H, m), 2.84(3H, s), 2.73(1H, d, J=8.3 Hz), 2.58–2.53(1H, m), 2.32–2.24(2H, m), 2.11–2.05(1H, m), 1.76–1.58(2H, m). IR(neat): 3300, 1610 cm$^{-1}$. HCl salt: amorphous solid. MS m/z: 378(M+H)$^+$; Anal. Calcd for C$_{23}$H$_{27}$N$_3$O$_2$.HCl.0.8H$_2$O.CH$_4$O: C, 62.61; H, 7.36; N, 9.13; Found: C,62.23; H, 7.26; N,9.50.

Example 71

Preparation of 4-{N-[2-(3-(S)-Methoxymethoxypyrrolidin-1-yl)-1-(S)-phenylethyl]-N-methylamino}-N'-(3,3,3,-trifluoropropyl)benzamide This was prepared from 4-{N-[2-(3-(S)-methoxymethoxypyrrolidin-1-yl)-1-(S)-phenylethyl]-N-methylamino}benzoic acid and 3,3,3,-trifluoropropylamine in 39% yield according to the procedures similar to those described in Example 1 (iii).

$^1$H NMR (270 MHz, CDCl$_3$) δ 7.63(2H, d, J=8.8 Hz), 7.31–7.24(5H, m), 6.80(2H, d, J=9.2 Hz), 6.21–6.12 (1H, m), 5.14(1H, dd, J=7.0, 8.1 Hz), 4.59(1H, d, J=7.0 Hz), 4.55(1H, d, J=7.0 Hz), 4.21–4.12(1H, m), 3.69(2H, q, J=6.2 Hz), 3.29(3H, s), 3.07–3.03(2H, m), 2.85(3H, s), 2.84–2.80 (1H, m), 2.72–2.67(1H, m), 2.64–2.56(2H, m), 2.50–2.38 (2H, m), 2.08–2.01(1H, m), 1.77–1.76(1H, m).

Example 72

Preparation of 4-{N-[2-(3-(S)-Hydroxypyrrolidin-1-yl)-1-(S)-phenylethyl]-N-methylamino}-N'-(3,3,3,-trifluoropropyl)benzamide This was prepared from 4-{N-[2-(3-(S)-methoxymethoxypyrrolidin-1-yl)-1-(S)-phenylethyl]-N-methylamino}-N'-(3,3,3,-trifluoropropyl)benzamide in 69% yield according to the procedures similar to those described in Example 2.

$^1$H NMR (270 MHz, free amine, CDCl$_3$) δ 7.65(2H, d, J=8.8 Hz), 7.36–7.26(5H, m), 6.81(2H, d, J=9.2 Hz), 6.26–6.20 (1H, m), 5.16(1H, dd, J=5.9, 9.2 Hz), 4.25–4.19 (1H, m), 3.69(2H, q, J=6.2 Hz), 3.17–3.02(2H, m), 2.99–2.88(1H, m), 2.84(3H, s), 2.80–2.72(1H, m), 2.59–2.53(1H, m), 2.52–2.38(2H, m), 2.37–2.28(1H, m), 2.16–2.05(1H, m), 1.80–1,75(2H, m). IR(neat): 3350, 1610 cm$^{-1}$. HCl salt: amorphous solid. MS m/z: 436(M+H)$^+$;

Anal. Calcd for $C_{23}H_{28}N_3O_2F_3 \cdot HCl \cdot 0.4H_2O$: C, 57.65; H, 6.27; N, 8.77; Found: C,57.60; H, 6.26; N,8.50.

Example 73

Preparation of 4-{N-[2-(3-(S)-Methoxymethoxypyrrolidin-1-yl)-1-(S)-phenylethyl]-N-methylamino}-N'-(2-(S)-hydroxypropyl)benzamide This was prepared from 4-{N-[2-(3-(S)-methoxymethoxypyrrolidin-1-yl)-1-(S)-phenylethyl]-N-methylamino}benzoic acid and (S)-(−)-1-amino-2-propanol in 55% yield according to the procedures similar to those described in Example 1 (iii).
$^1$H NMR (270 MHz, CDCl$_3$) δ 7.67(2H, d, J=9.2 Hz), 7.40–7.20(5H, m), 6.80(2H, d, J=8.8 Hz), 6.50–6.40(1H, m), 5.14(1H, dd, J=7.0, 7.7 Hz) 4.60(1H, d, J=6.6 Hz), 4.55(1H, d, J=7.0 Hz), 4.23–4.13(1H, m), 4.07–3.95(1H, m), 3.66–3.55(1H, m), 3.40–3.25(1H, m), 3.30(3H, s), 3.13–3.00(2H, m), 2.90–2.80(1H, m), 2.86(3H, s), 2.76–2.52(3H, m), 2.13–1.98(1H, m), 1.85–1.45(2H, m), 1.23(3H, d, J=6.2 Hz).

Example 74

Preparation of 4-{N-[2-(3-(S)-Hydroxypyrrolidin-1-yl)-1-(S)-phenylethyl]-N-methylamino}-N'-(2-(S)-hydroxypropyl)benzamide This was prepared from 4-{N-[2-(3-(S)-methoxymethoxypyrrolidin-1-yl)-1-(S)-phenylethyl]-N-methylamino}-N'-(2-(S)-hydroxypropyl)benzamide in 81% yield according to tihe procedures similar to those described in Example 2.
$^1$H NMR (270 MHz, free amine, CDCl$_3$) δ 7.68(2H, d, J=8.8 Hz), 7.40–7.20(5H, m), 6.80(2H, d, J=8.8 Hz), 6.60–6.50(1H, m), 5.15(1H, dd, J=5.9, 9.2 Hz), 4.28–4.18 (1H, m), 4.07–3.93(1H, m), 3.66–3.55(1H, m), 3.35–3.23 (1H, m), 3.13(1H, dd, J=9.2, 12.8 Hz), 3.03(1H, dd, J=5.9, 12.8 Hz), 2.95–2.80(1H, m), 2.83(3H, s), 2.72(1H, d, J=9.5 Hz), 2.56(1H, dd, J=4.8, 9.9 Hz), 2.40–2.25(1H, m), 2.20–1.75(3H, m), 1.70–1.55(1H, m), 1.22(3H, d, J=6.2 Hz). IR(neat): 3350, 1610 cm$^{-1}$. Maleic acid salt: amorphous solid. MS m/z: 396(M−H)$^-$; Anal. Calcd for $C_{23}H_{31}N_3O_3 \cdot C_4H_4O_4 \cdot 0.3H_2O$: C, 62.49; H, 6.91; N, 8.10; Found: C,62.65; H, 7.24; N,7.90.

Example 75

Preparation of 4-{N-[1-(R)-(3-Methoxymethoxyphenyl)-2-(3-(S)-methoxymethoxypyrrolidin-1-yl)-ethyl]-N-methylamino}-N'-propylbenzamide (i) Methyl 4-{N-[1-(R)-(3-methoxymethoxyphenyl)-2-(3-(S)-methoxymethoxypyrrolidin-1-yl)-ethyl]-N-methylamino}benzoate 2-(S)-(3-Methoxymethoxyphenyl)-2-(3-(S)-methoxymethoxypyrrolidin-1-yl)ethanol and 1-(R)-(3-methoxymethoxyphenyl)-2-(3-(S)-methoxymethoxypyrrolidin-1-yl)ethanol were prepared from (R)-1-(3-methoxymethoxyphenyl)-1,2-ethanediol-2-tosylate in 58% yield as a mixture according to the procedures similar to those described in Preparation 3. Title compound was prepared by reactin, the mixture of 2-(S)-(3-methoxymethoxyphenyl)-2-(3-(S)-methoxymethoxypyrrolidin-1-yl)ethanol and 1-(R)-(3-methoxymethoxyphenyl)-2-(3-(S)-methoxymethoxypyrrolidin-1-yl)ethanol wth methyl 4-methylaminobenzoate in 54% yield according to the procedures similar to those described in Example 1 (i).
$^1$H NMR (270 MHz, CDCl$_3$) δ 7.88 (2H, d, J=8.8 Hz), 7.23–7.19 (1H, m), 6.95–6.90(3H, m), 6.77(2H, d, J=8.8 Hz), 5.13(2H, s), 5.12–5.08(1H, m), 4.58 (1H, d, J=6.6 Hz), 4.53 (1H, d, J=6.6 Hz), 4.22–4.15 (1H, m), 3.84 (3H, s), 3.45(3H, s), 3.28 (3H, s), 3.13–2.92(2H, m), 2.88 (3H, s), 2.90–2.84(1H, m), 2.75–2.66(1H, m), 2.61–2.50(2H, m), 2.06–1.99(1H, m), 1.83–1.74(1H, m).
(ii) 4-{N-[1-(R)-(3-Methoxymethoxyphenyl)-2-(3-(S)-methoxymethoxypyrrolidin-1-yl)-ethyl]-N-methylamino}benzoic Acid This was prepared from methyl 4-{N-[1-(R)-(3-methoxymethoxyphenyl)-2-(3-(S)-methoxymethoxypyrrolidin-1-yl)-ethyl]-N-methylamino}benzoate in 91% yield according to the procedures similar to those described in Example 1 (ii).
$^1$H NMR (270 MHz, CDCl$_3$) δ 7.91 (2H, d, J=8.8 Hz), 7.30–7.12(1H, m), 6.98–6.84(3H, m), 6.82(2H, d, J=9.2 Hz), 5.35–5.25(1H, m), 5.14(2H, s), 4.60(1H, d, J=7.0 Hz), 4.55(1H, d, J=7.0 Hz), 4.30–4.20(1H, m), 3.45(3H, s), 3.30(3H, s), 3.25–3.05(2H, m), 2.90(3H, s), 2.90–2.60(4H, m), 2.20–2.00(1H, m), 1.90–1.80(1H, m).
(iii) 4-{N-[1-(R)-(3-Methoxymethoxyphenyl)-2-(3-(S)-methoxymethoxypyrrolidin-1-yl)-ethyl]-N-methylamino}-N'-propylbenzamide This was prepared from 4-{N-[1-(R)-(3-methoxymethoxyphenyl)-2-(3-(S)-methoxymethoxypyrrolidin-1-yl)-ethyl]-N-methylamino}benzoic acid and n-propylamine in 71% yield according to the procedures similar to those described in Example 1 (iii).
$^1$H NMR (270 MHz, CDCl$_3$) δ 7.64(2H, d, J=8.8 Hz), 7.28–7.18(1H, m), 6.98–6.88(3H, m), 6.78(2H, d, J=9.2 Hz), 6.00–5.90(1H, m), 5.14(2H, s), 5.09(1H, t, J=7.7 Hz), 4.58 (1H, d, J=7.0 Hz), 4.54(1H, d, J=7.0 Hz), 4.25–4.12(1H, m), 3.46(3H, s), 3.45–3.35(2H, m), 3.29(3H, s), 3.08–2.96(2H, m), 2.92–2.80(1H, m), 2.86(3H, s), 2.75–2.50(3H, m), 2.12–1.95(1H, m), 1.85–1.52(3H, m), 0.97(3H, t, J=7.3 Hz).

Example 76

Preparation of 4-{N-[1-(R-(3-t-Butoxycarbonylmethoxyphenyl)-2-(3-(S)-hydroxypyrrolidin-1-yl)-ethyl]-N-methylamino}-N'-propylbenzamide This was prepared from 4-{N-[1-(R)-(3-methoxymethoxyphenyl)-2-(3-(S)-methoxymethoxypyrrolidin-1-yl)-ethyl]-N-methylamino}-N'-propylbenzamide in 11% over all yield according to the procedures similar to those described in Example 2 and Example 36.
$^1$H NMR (270 MHz, CDCl$_3$) δ 7.65(2H, d, J=8.8 Hz), 7.26–7.20(1H, m), 6.92–6.89 (2H, m), 6.79(2H, d, J=9.2 Hz), 6.79–6.75(1H, m), 6.01–5.92(1H, m), 5.11(1H, dd, J=7.0, 7.2 Hz), 4.47(2H, s), 4.26–4.17(1H, m), 3.45–3.35 (2H, m), 3.04(2H, d, J=7.3 Hz), 2.98–2.91(1H, m), 2.81(3H, s), 2.69(1H, d, J=9.2 Hz), 2.49(1H, dd, J=4.8, 9.9 Hz), 2.40–2.25(1H, m), 2.17–2.06(1H, m), 1.75–1.52(4H, m), 1.45(9H, s), 0.98(3H, t, J=7.3 Hz).

Example 77

Preparation of 4-{N-[1-(R)-(3-Carboxymethoxyphenyl)-2-(3-(S)-hydroxypyrrolidin-1-yl)-ethyl]-N-methylamino}-N'-propylbenzamide This was prepared from 4-{N-[1-(R)-(3-t-butoxycarbonylmethoxyphenyl)-1-(3-(S)- hydroxypyrrolidin-1-yl)-ethyl]-N-methylamino}-N'-propylbenzamide in 86% yield according to the procedures similar to those described in Example 3. HCl salt: ligt brown solid.

$^1$H NMR (270 MHz, DMSO-d6) δ 10.55–10.15(1H, m), 8.32–8.24(1H, m), 7.91–7.80(2H, m), 7.34(1H, t, J=7.7 Hz), 7.21–7.09(2H,m), 6.98–6.84(3H, m), 5.95–5.80(1H, m), 4.72(2H, s), 4.60–4.40(1H, m), 4.40–3.20(7H, m), 2.82 (1.2H, s), 2.81(1.8H,s), 2.50–2.30(2H, m), 2.15–1.85(2H, m), 1.70–1.50(2H, m), 0.96(3H, t, J=7.3 Hz). IR(KBr): 3400, 1730, 1610 cm$^{-1}$. MS m/z: 456(M+H)$^+$. Anal. Calcd for C$_{25}$H$_{33}$N$_3$O$_5$.HCl.3.5H$_2$O: C, 54.10; H, 7.45; N, 7.57; Found: C, 54.49; H, 7.85; N, 7.76.

Example 78

Preparation of 3-Fluoro-4-{N-[2-(3-(S)-methoxymethoxypyrrolidin-1-yl)-1-(S)-phenylethyl]-N-methylamino}-N'-propylbenzamide (i) Methyl 3-fluoro-4-{N-[2-(3-(S)-methoxymethoxypyrrolidin-1-yl)-1-(S)-phenylethyl]-N-methylamino}benzoate This was prepared from 2-(3-(S)-methoxymethoxypyrrolidin-1-yl)-1-(S)-phenylethanol and 2-(3-(S)-methoxymethoxypyrrolidin-1-yl)-2-(R)-phenylethanol and methyl 3-fluoro-4-methylaminobenzoate in 52% yield according to the procedures similar to those described in Example 29 (i).

$^1$H NMR (270 MHz, CDCl$_3$) δ 7.72–7.62(2H, m), 7.38–7.22 (5H, m), 6.81(1H, t, J=8.8 Hz), 5.12–5.02(1H, m), 4.58 (1H, d, J=7,0 Hz), 4.55(1H, d, J=7.0 Hz), 4.15–4.03 (1H,m), 3.88(3H, s), 3.30(3H, s), 3.18–2.95(2H, m), 2.88–2.78(1H, m), 2.71(3H, d, J=0.7 Hz), 2.67–2.45(3H, m), 2.05–1.90(1H, m), 1.75–1.60(1H, m).

(ii) 3-Fluoro-4-{N-[2-(3-(S)-methoxymethoxypyrrolidir-1-yl)-1-(S)-phenylethyl]-N-methylamino}benzoic Acid This was prepared from methyl 3-fluoro-4-{N-[2-(3-(S)-methoxymethoxypyrrolidin-1-yl)-1-(S)-phenylethyl]-N-methylamino}benzoate in 100% yield according to the procedures similar to those described in Example 1 (ii).

$^1$H NMR (270 MHz, CDCl$_3$) δ 7.63–7.54(2H, m), 7.38–7.22 (5H, m), 6.76(1H, t, J=8.4 Hz), 5.27–5.17(1H,m), 4.61 (1H, d, J=7.0 Hz), 4.58(1H, d, J=7.0 Hz), 4.30–4.20 (1H,m), 3.55–3.43(1H, m), 3.40–3.15(3H, m), 3.31(3H, s), 2.95–2.73(2H, m), 2.74(3H, s), 2.22–2.05(1H, m), 1.95–1.80(1H, m).

(iii) 3-Fluoro-4-{N-[2-(3-(S)-methoxymethoxypyrrolidin-1-yl)-1-(S)-phenylethyl]-N-methylamino}-N'-propylbenzamide This was prepared from 3-fluoro-4-{N-[2-(3-(S)-methoxymethoxypyrrolidin-1-yl)-1-(S)-phenylethyl]-N-methylamino}benzoic acid and n-propylamine in 80% yield according to the procedures similar to those described in Example 1 (iii).

$^1$H NMR (270 MHz, CDCl$_3$) δ 7.48 (1H, dd, J=1.8, 14.3 Hz), 7.41–7.20(6H, m), 6.80(1H, t, J=8.8 Hz), 6.08–6.00 (1H,m), 5.03–4.92(1H,m), 4.58 (1H, d, J=7.0 Hz), 4.54(1H, d, J=6.6 Hz), 4.13–4.03(1H,m), 3.45–3.35(2H, m), 3.30(3H, s), 3.18–3.07(1H, m), 3.02(1H, dd, J=6.6, 12.8 Hz), 2.83 (1H, dd, J=6.2, 9.9 Hz), 2.68(3H, s), 2.65–2.45((3H, m), 2.07–1.93 (1H, m), 1.75–1.55(3H, m), 0.99(3H, t, J=7.3 Hz).

Example 79

Preparation of 3-Fluoro-4-{N-[2-(3-(S)-hydroxypyrrolidin-1-yl)-1-(S)-phenylethyl]-N-methylamino}-N'-propylbenzamide This was prepared from 3-fluoro-4-{N-[2-(3-(S)-methoxymethoxypyrrolidin-1-yl)-1-(S)-phenylethyl]-N-methylamino}-N'-propylbenzamide in 40% yield according to the procedures similar to those described in Example 2.

$^1$H NMR (270 MHz, free amine, CDCl$_3$) δ 7.53 (1H, dd, J=2.2, 14.3 Hz), 7.41–7.24(6H, m), 6.83(1H, t, J=8.8 Hz), 6.11–6.02(1H,m), 5.12–5.02(1H,m), 4.22–4.13(1H,m), 3.45–3.35(2H, m), 3.35–3.23(1H, m), 3.00(1H, dd, J=5.5, 12.5 Hz), 2.92–2.73(2H, m), 2.68(3H, s), 2.60–2.50(1H, m), 2.33–2.18(1H, m), 2.13–1.95(1H, m), 1.90 (1H, br. s), 1.70–1.48(3H, m), 0.99(3H, t, J=7.3 Hz); Maleic acid salt: amorphous solid. IR(KBr): 3350, 1620 cm$^-$. MS: 400(M+H)$^+$; Anal. Calcd for C$_{23}$H$_{30}$N$_3$O$_2$F.C$_4$H$_4$O$_4$.0.5H$_2$O: C, 61.82; H, 6.72; N, 8.01; Found: C, 61.52; H,6.70; N, 8.02.

Example 80

Preparation of 4-{N-[2-(3-(S)-Methoxymethoxypyrrolidin-1-yl)-1-(S)-phenylethy]-N-methylamino}-N'-(2,2,3,3,-pentafluoropropyl) benzamide This was prepared from 2-(3-(S)-methoxymethoxypyrrolidin-1-yl)-1-(S)-phenylethanol and 2-(3-(S)-methoxymethoxypyrrolidin-1-yl)-2-(R)-phenylethanol and 4-methylamino-N'-(2,2,3,3,-pentafluoropropyl)benzamide in 32% yield according to the procedures similar to those described in Example 1 (i).

$^1$H NMR (270 MHz, CDCl$_3$) δ 7.67(2H, d, J=8.8 Hz), 7.34–7.25 (5H, m), 6.81(2H, d, J=9.2 Hz), 6.30–6.13(1H, m), 5.15(1H, t, J=7.7 Hz), 4.59 (1H, d, J=6.6 Hz), 4.55(1H,d, J=6.6 Hz), 4.23–4.10(3H, m), 3.30(3H, s), 3.07–3.04(2H, m), 2.87(3H, m), 2.84–2.80(1H, m), 2.76–2.67(1H, m), 2.64–2.53(2H, m), 2.09–2.01(1H, m), 1.77–1.70(1H, m).

Example 81

Preparation of 4-{N-[2-(3-(S)-Hydroxypyrrolidin-1-yl)-1-(S)-phenylethy]-N-methylamino}-N'-(2,2,3,3, 3,-pentafluoropropyl)benzamide This was prepared from 4-{N-[2-(3-(S)-methoxymethoxypyrroldin-1-yl)-1-(S)-phenylethyl]-N-methylamino}-N'-(2,2,3,3,3,-pentafluoropropyl)benzamide in 97% yield according to the procedures similar to those described in Example 2.

$^1$H NMR (270 MHz, free amine, CDCl$_3$) δ 7.69(2H, d, J=8.8 Hz), 7.36–7.26 (5H, m), 6.82(2H, d, J=8.8 Hz), 6.20–6.16(1H, m), 5.16(1H, dd, J=5.5, 8.8 Hz), 4.25–4.21 (1H, m), 4.14(2H, dd, J=62, 14.7 Hz), 3.14(1H, dd, J=9.2, 12.8 Hz), 3.04(1H, dd, J=5.9, 12.8 Hz), 2.95–2.88(1H, m), 2.86(3H, s), 2.73(1H, d, J=9.5 Hz), 2.57(1H, dd, J=4.8, 9.5 Hz), 2.37–2.29(1H, m), 2.16–2.05(1H, m), 1.80–1.60(2H, m); IR(neat): 3350, 1610 cm$^{-1}$; HCl salt: amorphous solid. MS m/z: 470(M−H)$^-$; Anal. Calcd for C$_{23}$H$_{26}$N$_3$O$_2$F$_5$.HCl.0.4CH$_4$O: C, 53.63; H, 5.44; N, 8.16; Found: C,53.90; H, 5.33; N,7.79.

Example 82

Preparation of 4-{N-[2-(3-(S)-Methoxymethoxypyrrolidin-1-yl)-1-(S)-phenylethyl]-N-methylamino}-N'-tert-amylbenzamide This was prepared from 2-(3-(S)-methoxymethoxypyrrolidin-1-yl)-1-(S)-phenylethanol and 2-(3-(S)-methoxymethoxypyrrolidin-1-yl)-2-(R)-phenylethanol and 4-methylamino-N'-tert-amylbenzamide in 36% yield according to the procedures similar to those described in Example 1 (i).

¹H NMR (270 MHz, CDCl₃) δ 7.60(2H, d, J=8.8 Hz), 7.34–7.23 (5H, m), 6.78(2H, d, J=8.8 Hz), 5.73–5.62(1H, m), 5.13(1H, dd, J=6.2, 8.4 Hz), 4.60 (1H, d, J=7.0 Hz), 4.55(1H, d, J=7.0 Hz), 4.17–4.15(1H, m), 3.30(3H, s), 3.07–3.02(2H, m), 2.83(3H, s), 2.86–2.80(1H, m), 2.72–2.64(1H, m), 2.63–2.57(2H, m), 2.09–2.01(1H, m), 1.87–1.79(1H, m), 1.83(2H, q, J=7.3 Hz), 1.39(6H, s), 0.88(3H, t, J=7.3 Hz).

Example 83

Preparation of 4-{N-[2-(3-(S)-Hydroxypyrrolidin-1-yl)-1-(S)-phenylethyl]-N-methylamino}-N'-tert-amylbenzamide This was prepared from 4-{N-[2-(3-(S)-methoxymethoxypyrroidin-1-yl)-1-(S)-phenylethyl]-N-methylamino}-N'-tert-amylbenzamide in 88% yield according to the procedures similar to those described in Example 2.

¹H NMR (270 MHz, free amine, CDCl₃) δ 7.62(2H, d, J=8.8 Hz), 7.35–7.22 (5H, m), 6.79(2H, d, J=8.8 Hz), 5.73–5.63(1H, m), 5.14(1H, dd, J=5.9, 9.2 Hz), 4.24–4.20 (1H,m), 3.12(1H, dd, J=8.8, 12.8 Hz), 3.03(1H, dd, J=5.9, 12.8 Hz), 2.93–2.86(1H, m), 2.83(3H, s), 2.73(1H, d, J=9.9 Hz), 2.56(1H, dd, J=4.8, 9.5 Hz), 2.36–2.27(1H, m), 2.14–2.04(1H, m), 1.83(2H, q, J=7.3 Hz), 1.80–1.60(2H,m), 1.40(6H, s), 0.88(3H, t, J=7.3 Hz). IR(neat): 3350, 1610 cm⁻¹. HCl salt: amorphous solid. MS mz: 410(M+H)⁺; Anal. Calcd for $C_{25}H_{35}N_3O_2 \cdot HCl \cdot 0.2CH_4O$: C, 66.78; H, 8.16; N, 9.35; Found: C,66.67; H, 8.43; N,9.33.

Example 84

Preparation of 4-{N-[2-(3-(S)-Methoxymethoxypyrrolidin-1-yl)-1-(S)-phenylethyl]-N-methylamino}-N'-tert-butylbenzamide This was prepared from 2-(3-(S)-methoxymethoxypyrrolidin-1-yl)-1-(S)-phenylethanol and 2-(3-(S)-methoxymethoxypyrrolidin-1-yl)-2-(R)-phenylethanol and 4-methylamino-N'-tert-butylbenzamide in 66% yield according to the procedures similar to those described in Example 1 (i).

¹H NMR (270 MHz, CDCl₃) δ 7.61(2H, d, J=8.8 Hz), 7.40–7.20 (5H, m), 6.78(2H, d, J=9.2 Hz), 5.90–5.65(1H, m), 5.18–5.10(1H, m), 4.60 (1H, d, J=6.6 Hz), 4.56(1H, d, J=7.0 Hz), 4.24–4.14(1H,m), 3.30(3H, s), 3.10–2.98(2H, m), 2.90–2.78(1H, m), 2.84(3H, s), 2.76–2.54(3H, m), 2.15–1.95(1H, m), 1.80–1.60(1H, m), 1.45(9H, s).

Example 85

Preparation of 4-{N-[2-(3-(S)-Hydroxypyrrolidin-1-yl)-1-(S)-phenylethyl]-N-methylamino}-N'-tert-butylbenzamide This was prepared from 4-{N-[2-(3-(S)-methoxymethoxypyrrolidin-1-yl)-1-(S)-phenylethyl]-N-methylamino}-N'-tert-butylbenzamide in 52% yield according to the procedures similar to those described in Example 2.

¹H NMR (270 MHz, free amine, CDCl₃) δ 7.62(2H, d, J=8.8 Hz), 7.35–7.24 (5H, m), 6.79(2H, d, J=9.2 Hz), 5.83–5.77(1H, m), 5.14(1H, dd, J=5.5, 8.8 Hz), 4.26–4.18 (1H,m), 3.13(1H, dd, J=9.2, 12.8 Hz), 3.03(1H, dd, J=5.9, 12.8 Hz), 2.92–2.86(1H, m), 2.83(3H, s), 2.74(1H, d, J=9.9 Hz), 2.55(1H, dd, J=4.8, 9.9 Hz), 2.36–2.27(1H, m), 2.11–2.08(1H, m), 1.72–1.54(2H, m), 1.45(9H, s). IR(neat): 3350, 1610 cm⁻¹. HCl salt: amorphous solid. MS m/z: 396(M+H)⁺; Anal. Calcd for $C_{24}H_{33}N_3O_2 \cdot HCl \cdot 1.2H_2O$: C, 63.55; H, 8.09; N, 9.26; Found: C,63.34, H,7.93; N,9.01.

Example 86

Preparation of 5-{N-[2-(3-(S)-Hydroxypyrrolidin-1-yl)-1-(S)-phenylethyl]-N-methylamino}-N'-propylpicolinamide This was prepared from 2-(3-(S)-methoxymethoxypyrrolidin-1-yl)-1-(S)-phenylethanol and 2-(3-(S)-methoxymethoxypyrrolidin-1-yl)-2-(R)-phenylethanol and 5-methylamino-N'-propylpicolinamide in 24% over all yield according to the procedures similar to those described in Example 1 (i) and Example 2.

¹H NMR (270 MHz, free amine, CDCl₃) δ 8.12(1H, d, J=3.3 Hz), 8.02(1H, d, J=8.8 Hz), 7.82–7.74(1H, m), 7.38–7.24 (5H, m), 7.13(1H, dd, J=3.3, 8.8 Hz), 5.10(1H, dd, J=5.5, 9.5 Hz), 4.30–4.20(1H, m), 3.45–3.35(2H, m), 3.17(1H, dd, J=9.5, 12.8 Hz), 3.01(1H, dd, J=5.5, 12.8 Hz), 2.95–2.84(1H, m), 2.91(3H, s), 2.70(1H, d, J=9.2 Hz), 2.61(1H, dd, J=4.8, 9.5 Hz), 2.42–2.30(1H, m), 2.18–2.02 (1H, m), 1.80–1.55(4H,m), 0.98(3H, t, J=7.3 Hz). Fumaric acid salt: amorphous solid. IR(KBr): 3400, 1650 cm⁻¹. MS m/z: 383(M+H)⁺; Anal. Calcd for $C_{22}H_{30}N_4O_2 \cdot C_4H_4O_4 \cdot 0.5H_2O$: C, 61.52; H, 6.95; N, 11.04; Found: C, 61.75; H, 7.09; N, 10.95.

Example 87

Preparation of 4-{N-Hydroxy-N-[2-(3-(S)-methoxymethoxypyrrolidin-1-yl)-1-(S)-phenylethyl]amino}-N'-propylbenzamide This was prepared from 2-(3-(S)-methoxymethoxypyrrolidin-1-yl)-1-(S)-phenylethanol and 2-(3-(S)-methoxymethoxypyrrolidin-1-yl)-2-(R)-phenyiethanol and methyl 4-hydroxyaminobenzoate in 33% over all yield according to the procedures similar to those described in Example 1 (i), (ii) and (iii).

¹H NMR (270 MHz, CDCl₃) δ 7.55(2H, d, J=8.8 Hz), 7.43–7:18 (5H, m), 6.90(2H, d, J=8.8 Hz), 6.05–5.95(1H, m), 4.87(1H, dd, J=5.1, 10.3 Hz), 4.63 (1H, d, J=7.0 Hz), 4.60(1H, d, J=7.0 Hz), 4.30–4.20(1H, m), 3.58–3.46(2H, m), 3.43–3.25(2H, m), 3.35(3H, s), 2.95–2.50(4H, m), 2.20–1.80(2H, m), 1.70–1.50(2H, m), 0.96(3H, t, J=7.3 Hz).

Example 88

Preparation of 4-{N-Hydroxy-N-[2-(3-(S)-hydroxypyrrolidin-1-yl)-1-(S)-phenylethyl]amino}-N'-propylbenzamide This was prepared from 4-{N-hydroxy-N-[2-(3-(S)-methoxymethoxypyrrolidin-1-yl)-1-(S)-phenylethyl]amino}-N'-propylbenzamide in 63% yield according to the precedures similar to those described in Example 2.

¹H NMR (270 MHz, free amine, CDCl₃) δ 8.86(1H, s), 8.18–8.08(1H, m), 7.64(2H, d, J=8.8 Hz), 7.42(2H, d, J=6.6 Hz), 7.27–7.12 (3H, m), 7.07(2H, d, J=8.8 Hz), 4.06(1H, dd, J=6.6, 7.3 Hz), 4.62 (1H, d, J=4.8 Hz), 4.15–4.05(1H,m), 3.20–3.10(2H, m), 3.07–2.92(2H, m), 2.74(1H, dd, J=6.2, 9.5 Hz), 2.56(2H, t, J=7.3 Hz), 2.36(1H, dd, J=9.5 Hz), 2.00–1.80(1H, m), 1.55–1.40(3H, m), 0.86(3H, t, J=7.3 Hz). Fumaric acid salt: amorphous solid. IR(KBr): 3300, 1630 cm⁻¹. MS m/z: 384(M+H)⁺; Anal. Calcd for $C_{22}H_{29}N_3O_3 \cdot C_4H_4O_4 \cdot 0.5H_2O$: C, 61.40; H, 6.74; N, 8.26; Found: C, 61.40; H,6.78; N, 8.08.

Example 89

Preparation of 4-{N-[2-(3-(S)-Fluoropyrrolidin-1-yl)-1-(S)-phenylethyl]-N-methylamino}-N'-(2-(S)-hydroxypropyl)benzamide This was prepared from 4-{N-[2-(3-(S)-fluoropyrrolidin-1-yl)-1-(S)-phenylethyl]-N-methylamino}benzoic acid and (S)-(+)-1-amino-2-propanol in 38% yield according to the procedures similar to those described in Example 1 (iii).

$^1$H NMR (270 MHz, free amine, CDCl$_3$) δ 7.67(2H, d, J=8.8 Hz), 7.35–7.23 (5H, m), 6.78(2H, d, J=8.8 Hz), 6.47–6.42 (1H, m), 5.21–4.94(1H, m), 5.11(1H, dd, J=6.2, 8.4 Hz), 4.03–3.97(1H, m), 3.64–3.56(1H, m), 3.35–3.25 (1H, m), 3.16–3.01(2H, m), 2.89–2.76(3H, m), 2.87(3H, s), 2.58–2.50(1H, m), 2.11–1.90(1H, m), 1.76–1.55(2H, m), 1.22(3H, d, J=6.6 Hz); Fumaric acid salt: amorphous solid. MS m/z: 400(M+H)$^+$; Anal. Calcd for C$_{23}$H$_{30}$N$_3$O$_2$F.C$_4$H$_4$O$_4$.0.8CH$_4$O: C, 61.70; H, 6.93; N, 7.76. Found: C, 61.52; H, 6.59; N,7.64.

Example 90

Preparation of 2-Chloro-4-{N-[2-(3-(S)-fluoropyrrolidin-1-yl)-1-(S)-phenylethyl]-N-methylamino}-N'-propylbenzamide This was prepared from 2-(3-(S)-fluoropyrrolidin-1-yl)-1-(S)-phenylethanol and 2-(3-(S)-fluoropyrrolidin-1-yl)-2-(R)-phenylethanol and 2-chloro-4-methylamino-N'-propylbenzamide in 13% yield according to the procedures similar to those described in Example 1 (i).

$^1$H NMR (270 MHz, free amine, CDCl$_3$) δ 7.75(1H, d, J=8.4 Hz), 7.38–20 (5H, m), 6.78–6.70(2H, m), 6.58–6.50 (1H, m), 5.25–4.95(1H, m), 5.04(1H, dd, J=6.2, 8.4Hz), 3.50–3.37(2H, m), 3.12(1H, dd, J=9.2, 12.8 Hz), 3.03(1H, dd, J=5.9, 12.8 Hz), 2.90–2.75(2H, m), 2.85(3H, s), 2.60–2.50(1H, m), 2.17–1.85 (2H, m), 1.70–1.55(3H, m), 0.99(3H, t, J=7.3 Hz). Fumaric acid salt: amorphous solid. MS m/z: 418(M+H)$^+$; Anal. Calcd for C$_{23}$H$_{29}$N$_3$OFCl.C$_4$H$_4$O$_4$.0.1H$_2$O: C, 60.52; H, 6.25; N, 7.84. Found: C, 60.16; H, 6.61; N,7.64.

Example 91

Preparation of 4-{N-[2-(3-(S)-Fluoropyrrolidin-1-yl)-1-(S)-phenylethyl]-N-hydroxyamino}-N'-propylbenzamide This was prepared from 2-(3-(S)-fluoropyrrolidin-1-yl)-1-(S)-phenylethanol and 2-(3-(S)-fluoropyrrolidin-1-yl)-2-(R)-phenylethanol and 4-hydroxyamino-N'-propylbenzamide in 56% yield according to the procedures similar to those described in Example 1 (i).

HCl salt: mp: 195–200° C.

$^1$H NMR (270 MHz, DMSO) δ 10.67(1H, br. s), 9.35–9.20(1H, m), 8.30–8.20(1H, m), 7.70(2H, d, J=8.4 Hz), 7.50–7.15 (7H, m), 5.70–5.35(2H, m), 4.25–3.30(6H, m), 3.25–3.10(2H, m), 2.70–2.10(2H, m), 1.60–1.40(2H, m), 0.86(3H, t, J=7.3 Hz); IR(KBr): 1600 cm$^{-1}$; MS m/z: 384(M−H)$^+$; Anal. Calcd for C$_{22}$H$_{28}$N$_3$O$_2$F.HCl: C, 62.63; H, 6.93; N, 9.96. Found: C, 62.23; H, 7.10; N,9.79.

Example 92

Preparation of 5-{N-[2-(3-(S)-Fluoropyrrolidin-1-yl)-1-(S)-phenylethyl]-N-methylamino}-N'-propylpicolinamide This was prepared from 2-(3-(S)-fluoropyrrolidin-1-yl)-1-(S)-phenylethanol and 2-(3-(S)-fluoropyrrolidin-1-yl)-2-(R)-phenylethanot and 5-methylamino-N'-propylpicolinamide in 26% yield according to the procedures similar to those described in Example 1 (i).

$^1$H NMR (270 MHz, free analine, CDCl$_3$) δ 8.10(1H, d, J=2.9 Hz), 8.01(1H, d, J=8.8 Hz), 7.82–7.74(1H, m), 7.38–7.24 (5H, m), 7.11(1H, dd, J=2.9, 8.8 Hz), 5.23–4.95 (1H, m), 5.07(1H, dd, J=5.9, 9.5 Hz), 3.45–3.35(2H, m), 3.18(1H, dd, J=9.5, 12.8 Hz), 3.03(1H, dd, J=5.9, 12.8 Hz), 2.95–2.75(2H, m), 2.93(3H, s), 2.60–2.50(1H, m), 2.18–1.90(2H, m), 1.70–1.55(3H, m), 0.98(3H, t, J=7.3 Hz). Fumaric acid salt: amorphous solid. IR(KBr): 1650 cm$^{-1}$. MS m/z: 385(M+H)$^+$; Anal. Calcd for C$_{22}$H$_{29}$N$_4$OF.C$_4$H$_4$O$_4$.0.6H$_2$O: C, 61.07; H, 6.74; N, 10.96; Found: C, 60.87; H, 6.35; N, 10.89.

Example 93

Preparation of 4-{N-Methylamino-N-[2-(3-pyrrolin-1-yl)-1-(S)-phenylethyl]}-N'-propylbenzamide This was prepared from 2-(R)-phenyl-2-(3-pyrrolin-1-yl)ethanol and 4-methylamino-N'-propylbenzamide in 12% yield according to the procedures similar to those described in Example 1 (i).

$^1$H NMR (270 MHz, free amine, CDCl$_3$) δ 7.65(2H, d, J=9.2 Hz), 7.35–7.24 (5H, m), 6.80(2H, d, J=9.2 Hz), 5.97 (1H,br. s), 5.72(2H, s), 5.12(1H, dd, J=7.0, 7.7 Hz), 3.58–3.49(4H, m), 3.38(2H, dd, J=5.9, 7.3 Hz), 3.25–3.21 (2H, m), 2.86(3H, s), 1.61(2H, dd, J=7.3, 14.7 Hz), 0.97(3H, t, J=7.3 Hz); IR(neat): 2950, 1650 cm$^{-1}$. HCl salt: amorphous solid. MS m/z: 363(M$^+$); Anal. Calcd for C$_{23}$H$_{29}$N$_3$O.HCl.0.1CH$_4$O.0.9H$_2$O: C, 66.16; H, 7.74, N, 10.02. Found: C, 66.56; H,7.64; N,9.65.

Example 94

Preparation of 4-{N-[2-(3-(R)-fluoropyrrolidin-1-yl)-1-(S)-phenylethyl]-N-methylamino}-N'-propylbenzamide This was prepared from 2-(3-(R)-fluoropyrrolidin-1-yl)-1-(S)-phenylethanol and 2-(3-(R)-fluoropyrrolidin-1-yl)-2-(R)-phenylethanol and 4-methylamino-N'-propylbenzamide in 47% yield according to the procedures similar to those described in Example 1 (i).

$^1$H NMR (270 MHz, free amine, CDCl$_3$) δ 7.67(2H, d, J=8.8 Hz), 7.34–7.24 (5H, m), 6.79(2H, d, J=8.8 Hz), 6.13 (1H, br. s), 5.25–4.95(1H, m), 5.13(1H, dd, J=6.2, 8.4 Hz), 3.41–3.34(2H, m), 3.17–3.05(2H, m), 3.02–2.77(3H, m), 2.82(3H, s), 2.59–2.51(1H, m), 2.09–1.91(2H, m), 1.72–1.54(2H, m), 0.95(3H, t, J=7.3 Hz); HCl salt: amorphous solid. MS m/z: 383(M$^+$); Anal. Calcd for C$_{23}$H$_{30}$N$_3$OF.HCl.0.5H$_2$O: C, 64.40; H, 7.52; N, 9.80. Found: C, 64.51; H,7.74; N, 9.46.

Example 95

Preparation of 4-{N-[2-(3-(S)-fluoropyrrolidin-1-yl)-1-(R)-phenylethyl]-N-methylamino}-N'-propylbenzamide This was prepared from 2-(3-(S)-fluoropyrrolidin-1-yl)-1-(R)-phenylethanol and 2-(3-(S)-fluoropyrrolidin-1-yl)-2-(S)-phenylethanol and 4-methylamino-N'-propylbenzamide in 28% yield according to the procedures similar to those described in Example 1 (i).

$^1$H NMR (270 MHz, free amine, CDCl$_3$) δ 7.65(2H, d, J=8.4 Hz), 7.30–7.24 (5H, m), 6.80(2H, d, J=8.4 Hz), 6.00

(1H, br. s), 5.25–4.95(2H, m), 3.43–3.36(2H, m), 3.13–3.07 (2H, m), 3.01–2.89(2H, m), 2.83(3H, s), 2.58–2.55(1H, m) 2.10–2.00(1H, m), 2.00–1.92(1H, m), 1.73–1.55(3H, m), 0.97(3H, t, J=7.3 Hz); HCl salt: amorphous solid. MS m/z: 383(M$^+$); Anal. Calcd for $C_{23}H_{30}N_3OF \cdot HCl \cdot 2H_2O$: C, 60.58; H, 7.74, N, 9.21. Found: C, 60.59; H, 7.36; N, 9.23.

Example 96

Preparation of 4-{N-[2-(3-(S)-Chloropyrrolidin-1-yl)-1-(S)-phenylethyl]-N-methylamino}-N'-propylbenzamide This was prepared from 2-(3-(S)-chloropyrrolidin-1-yl)-1-(S)-phenylethanol and 2-(3-(S)-chloropyrrolidin-1-yl)-2-(R)-phenylethanol and 4-methylamino-N'-propylbenzamide in 40% yield according to the procedures similar to those described in Example 1 (i).

$^1$H NMR (270 MHz, free amine, CDCl$_3$) δ 7.68(2H, d, J=8.8 Hz), 7.33–7.27 (5H, m), 6.78(2H, d, J=8.8 Hz), 6.23 (1H, br. s), 5.08(1H, dd, J=7.3, 7.7 Hz), 4.30–4.25(1H, m), 3.40–3.33(2H, m), 3.13–3.08(3H, m), 2.84(3H, s), 2.81–2.65(3H, m), 2.36–2.22(1H, m), 2.02–1.95(1H, m), 1.63–1.53(2H, m), 0.94(3H, t, J=7.3 Hz). HCl salt: amorphous solid. MS m/z: 399(M$^+$); Anal. Calcd for $C_{23}H_{30}N_3OCl \cdot HCl \cdot 2.5H_2O$: C, 57.38; H, 7.54; N, 8.73. Found: C, 57.10; H, 7.42; N, 8.48.

Example 97

Preparation of 4-{N-[2-(3-(S)-Chloropyrrolidin-1-yl)-1-(S)-phenylethyl]-N-methylamino}-N'-(2-(S)-hydroxypropyl)benzamide This was prepared from 2-(3-(S)-chloropyrrolidin-1-yl)-1-(S)-phenylethanol and 2-(3-(S)-chloropyrrolidin-1-yl)-2-(R)-phenylethanol and 4-methylamino-N'-(2-(S)-hydroxypropyl)benzamide in 45% yield according to the procedures similar to those described in Example 1 (i).

$^1$H NMR (270 MHz, free amine, CDCl$_3$) δ 7.68(2H, d, J=9.2 Hz), 7.35–7.28 (5H, m). 6.79(2H, d, J=8.8 Hz), 6.52 (1H, br. s), 5.10(1H, t, J=7.3 Hz), 4.32–4.27(1H, m), 4.02–3.97(1H, m), 3.64–3.56(1H, m), 3.35–3.24(1H, m), 3.14–3.10(3H, m), 2.86(3H, s), 2.82–2.76(2H, m), 2.74–2.69(1H, m), 2.38–2.27(1H, m), 2.05–1.80(2H, m), 1.22(3H, d, J=6.2 Hz); HCl salt: amorphous solid. MS m/z: 415(M$^+$).

Example 98

Preparation of 4-{N-[2-(3-(S)-Chloropyrrolidin-1-yl)-1-(S)-phenylethyl]-N-methylamino}-N'-(2-(R)-hydroxypropyl)benzamide This was prepared from 2-(3-(S)-chloropyrrolidin-1-yl)-1-(S)-phenylethanol and 2-(3-(S)-chloropyrrolidin-1-yl)-2-(R)-phenylethanol and 4-methylamino-N'-(2-(R)-hydroxypropyl)benzamide in 44% yield according to the procedures similar to those described in Example 1 (i).

$^1$H NMR (270 MHz, free amine, CDCl$_3$) δ 7.68(2H, d, J=9.2 Hz), 7.35–7.23 (5H, m), 6.79(2H, d, J=9.2 Hz), 6.53 (1H, br. s), 5.11(1H, t, J=7.3 Hz), 4.33–4.27(1H, m), 4.03–3.98(1H, m), 3.64–3.56(1H, m), 3.35–3.25(1H, m), 3.16–3.11(1H, m), 3.12(2H, d, J=7.3 Hz), 2.85(3H, s), 2.83–2.71(3H, m), 2.36–2.27(1H, m), 2.04–1.98(1H, m), 1.22(3H, d, J=6.2 Hz); HCl salt: amorphous solid. MS m/z: 416(M+H)$^+$; Anal. Calcd for $C_{23}H_{30}N_3O_2Cl \cdot HCl \cdot H_2O$: C, 58.72; H, 7.07; N, 8.93. Found: C, 58.56; H, 7.00; N, 8.76.

Example 99

Preparation of 4-{N-[2-(3-Oxopyrrolidin-1-yl)-1-(S)-phenylethyl]-N-methylamino}-N'-propylbenzamide To a stirred solution of oxalylchloride (0.26 ml, 3.0 mmol) in CH$_2$Cl$_2$ (15 ml) was added a solution of DMSO (0.29 ml, 4.0 mmol) in CH$_2$Cl$_2$ (1 ml) at –78° C. The reaction mixture was stirred for 10 min and a solution of 4-{N-[2-(3-(S)-hydroxypyrrolidin-1-yl)-1-(S)-phenylethyl]-N-methylamino}-N'-propylbenzamide (573 mg, 1.5 mmol) in CH$_2$Cl$_2$ (5 ml) was added and stirring was continued for an additional 15 min at –78° C. 60 min at –45° C. Triethylamine (1.6 m, 11.0 mmol) was added and then the reaction mixture was allowed to warm to room temperature. Saturated NH$_4$Cl aqueous solution was added and extracted with AcOEt. The extract was washed with water and brine, dried (Na$_2$SO$_4$), and concentrated to give brown oil, which was purified by column chromatography (silica gel; 70 g, CH$_2$Cl$_2$/MeOH: 50/1–40/1) to give 195 mg (34%) of paie yellow oil.

$^1$H NMR (270 MHz, free amine, CDCl$_3$) δ 7.66(2H, d, J=9.2 Hz), 7.36–7.25 (5H, m), 6.80(2H, d, J=9.2 Hz), 6.01 (1H, br. s), 5.17(1H, t, J=7.3 Hz), 3.43–3.36(2H, m), 3.17–3.13(2H, m), 3.07–2.92(4H, m), 2.85(3H, s), 2.35(2H, t, J=7.0 Hz), 1.6–1.53(2H, m), 0.97(3H, t, J=7.7 Hz). HCl salt: amorphous solid. MS m/z: 379(M$^+$).

Example 100

Preparation of 4-{N-[2-(3-(S)-Hydroxypyrrolidin-1-yl)-1-(S)-phenylethyl]-N-methylamino}-N'-propylbenzamide 4-{N-[2-(3-(S)-Methoxymethoxypyrrolidin-1-yl)-1-(S)-phenylethyl]-N-methylamino}-N'-propylbenzamide was prepared from 2-(3-(S)-methoxymethoxypyrrolidin-1-yl)-1-(S)-phenylethanol and 2-(3-(S)-methoxymethoxypyrrolidin-1-yl)-2-(R)-phenylethanol and 4-methylamino-N'-propylbenzamide according to the procedures similar to those described in Example 1 (i). Title compound was prepared from 4-{N-[2-(3-(S)-methoxymethoxypyrrolidin-1-yl)-1-(S)-phenylethyl]-N-methylamino}-N'-propylbenzamide in 65% over all yield according to the procedures similar to those described in Example 2. The title compound was the same as one obtained in Example 2.

$^1$H NMR (270 MHz, free amine, CDCl$_3$) δ 7.66(2H, d, J=8.8 Hz), 7.40–7.20(5H, m), 6.80(2H, d, J=9.2 Hz), 6.05–5.90(1H, m), 5.14(1H, dd, J=5.9, 9.2 Hz), 4.28–4.16 (1H, m), 3.46–3.32(2H, m), 3.12(1H, dd, J=9.2, 12.8 Hz), 3.03(1H, dd, J=5.9, 12.8 Hz), 2.95–2.80(1H,m), 2.83(3H, s), 2.72(1H, d, J=9.5 Hz), 2.56(1H, dd, J=4.8, 9.9 Hz), 2.33(1H, ddd, J=6.2, 8.8, 8.8 Hz), 2.18–2.00(1H, m), 1.89(1H, br. s), 1.70–1.50(3H, m), 0.97(3H, t, J=7.3 Hz); HCl salt: amorphous solid. MS m/z: 382(M+H)$^+$; Anal. Calcd for $C_{23}H_{31}N_3O_2 \cdot HCl \cdot 1.5H_2O \cdot CH_4O$: C, 60.43; H, 8.24; N, 8.812; Found: C,60.23; H,8.62; N,9.03.

The chemical structures of the compounds prepared in Examples 1 to 100 are summarized in the following tables. In the tables, H— represents hydrogen; Me-, Et-, Pr-, Bu-, Pe- and Am- represent methyl, ethyl, propyl, butyl, pentyl and amyl respectively; F— and Cl— represent fluorine and chlorine respectively; All- and PrD- represent allyl and propargyl respectively; MeO- and EtO- represent methoxy and ethoxy respectively; HO- represents hydroxy; Car- represents carboxy; Ph-, Py-, Th- and Bn- represent phenyl, pyridyl, thienyl and benzyl respectively; MOM-, t-Boc-, 2-THP- and TBDMS- represent methoxymethyl, t-butoxycarbonyl, tetrahydropyran-2-yl and t-butyldimethylsilyl respectively; tri-F-Pr-, penta-F-Pr- and 2-HO-Pr-represent 3,3,3-trifluoropropyl, 2,2,3,3,3-pentafluoropropyl and 2-hydroxypropyl respectively; O═ represents oxo; and cyc represents cyclic.

TABLE 1

(I)

| Ex.-# | A | Ar¹ | Ar² | R¹ | R² | R³ |
|---|---|---|---|---|---|---|
| 1 | (S)-MOM—O— | (S)-Ph— | 1,4-Ph— | Me— | Pr— | H— |
| 2 | (S)-HO— | (S)-Ph— | 1,4-Ph— | Me— | Pr— | H— |
| 3 | (S)-MOM—O— | (S)-Ph— | 1,4-Ph— | Me— | Me— | H— |
| 4 | (S)-HO— | (S)-Ph— | 1,4-Ph— | Me— | Me— | H— |
| 5 | (S)-MOM—O— | (S)-Ph— | 1,4-Ph— | Me— | Et— | H— |
| 6 | (S)-HO— | (S)-Ph— | 1,4-Ph— | Me— | Et— | H— |
| 7 | (S)-MOM—O— | (S)-Ph— | 1,4-Ph— | Me— | Bu— | H— |
| 8 | (S)-HO— | (S)-Ph— | 1,4-Ph— | Me— | Bu— | H— |
| 9 | (S)-2-THP—O— | (S)-Ph— | 1,4-Ph— | Me— | Pe— | H— |
| 10 | (S)-HO— | (S)-Ph— | 1,4-Ph— | Me— | Pe— | H— |
| 11 | (S)-MOM—O— | (S)-Ph— | 1,4-Ph— | Me— | i-Pr— | H— |
| 12 | (S)-HO— | (S)-Ph— | 1,4-Ph— | Me— | i-Pr— | H— |
| 13 | (S)-MOM—O— | (S)-Ph— | 1,4-Ph— | Me— | Ph— | H— |
| 14 | (S)-HO— | (S)-Ph— | 1,4-Ph— | Me— | Ph— | H— |
| 15 | (S)-MOM—O— | (S)-Ph— | 1,4-Ph— | Me— | 2-Cl—Bn— | H— |
| 16 | (S)-HO— | (S)-Ph— | 1,4-Ph— | Me— | 2-Cl—Bn— | H— |
| 17 | (S)-MOM—O— | (S)-Ph— | 1,4-Ph— | Me— | Me— | Me— |
| 18 | (S)-HO— | (S)-Ph— | 1,4-Ph— | Me— | Me— | Me— |
| 19 | (S)-2-THP—O— | (S)-Ph— | 1,4-Ph— | Me— | Pr— | Me— |
| 20 | (S)-HO— | (S)-Ph— | 1,4-Ph— | Me— | Pr— | Me— |
| 21 | (S)-MOM—O— | (S)-Ph— | 1,3-Ph— | Me— | Pr— | H— |
| 22 | (S)-HO— | (S)-Ph— | 1,3-Ph— | Me— | Pr— | H— |
| 33 | (S)-MOM—O— | (S)-3-MOM—O—Ph— | 1,4-Ph— | Me— | Pr— | H— |
| 34 | (S)-HO— | (S)-3-HO—Ph— | 1,4-Ph— | Me— | Pr— | H— |
| 35 | (S)-HO— | (S)-3-MeO—Ph— | 1,4-Ph— | Me— | Pr— | H— |
| 36 | (S)-HO— | (S)-3-t-Boc—MeO— | 1,4-Ph— | Me— | Pr— | H— |
| 37 | (S)-HO— | (S)-3-Car—MeO—Ph— | 1,4-Ph— | Me— | Pr— | H— |
| 38 | H— | (S)-Ph— | 1,4-Ph— | Me— | Pr— | H— |
| 40 | (S)-MOM—O— | (S)-Ph— | 2,5-Th— | Me— | Pr— | H— |
| 41 | (S)-HO— | (S)-Ph— | 2,5-Th— | Me— | Pr— | H— |
| 42 | (S)-MOM—O— | (S)-Ph— | 1,4-Ph— | H— | Pr— | H— |
| 43 | (S)-HO— | (S)-Ph— | 1,4-Ph— | H— | Pr— | H— |
| 44 | (S)-MOM—O— | (S)-3-Cl—Ph— | 1,4-Ph— | Me— | Pr— | H— |
| 45 | (S)-HO— | (S)-3-Cl—Ph— | 1,4-Ph— | Me— | Pr— | H— |
| 46 | (S)-F— | (S)-Ph— | 1,4-Ph— | Me— | Pr— | H— |
| 47 | (S)-MOM—O— | (R)-Ph— | 1,4-Ph— | Me— | Pr— | H— |
| 48 | (S)-HO— | (R)-Ph— | 1,4-Ph— | Me— | Pr— | H— |
| 51 | (S)-TBDMS—O— | (S)-Ph— | 1,4-Ph— | Me— | EtO— | H— |
| 52 | (S)-HO— | (S)-Ph— | 1,4-Ph— | Me— | EtO— | H— |
| 55 | (S)-MOM—O— | (S)-Ph— | 1,4-Ph— | Me— | 3-HO—Pr— | H— |
| 56 | (S)-HO— | (S)-Ph | 1,4-Ph— | Me— | 3-HO—Pr— | H— |
| 57 | (S)-MOM—O— | (S)-Ph | 1,4-Ph— | Me— | 2-(R)-HO—Pr— | H— |
| 58 | (S)-HO— | (S)-Ph— | 1,4-Ph— | Me— | 2-(R)-HO—Pr— | H— |
| 59 | (S)-MOM—O— | (S)-Ph— | 1,4-Ph— | Me— | i-Bu— | H— |
| 60 | (S)-HO— | (S)-Ph— | 1,4-Ph— | Me— | i-Bu— | H— |
| 61 | (S)-MOM—O— | (S)-Ph— | 1,4-Ph— | Me— | All— | H— |
| 62 | (S)-HO— | (S)-Ph— | 1,4-Ph— | Me— | All— | H— |
| 63 | (S)-MOM—O— | (S)-Ph— | 1,4-Ph— | Me— | cyc—Pr— | H— |
| 64 | (S)-HO— | (S)-Ph— | 1,4-Ph— | Me— | cyc—Pr— | H— |
| 65 | (S)-MOM—O— | (S)-Ph— | 1,4-Ph— | Me— | (S)-sec—Bu— | H— |
| 66 | (S)-HO— | (S)-Ph— | 1,4-Ph— | Me— | (S)-sec—Bu— | H— |
| 67 | (S)-MOM—O— | (S)-Ph— | 1,4-Ph— | Me— | (R)-sec—Bu— | H— |
| 68 | (S)-HO— | (S)-Ph— | 1,4-Ph— | Me— | (R)-sec—Bu— | H— |
| 69 | (S)-MOM—O— | (S)-Ph— | 1,4-Ph— | Me— | Prp— | H— |
| 70 | (S)-HO— | (S)-Ph— | 1,4-Ph— | Me— | Prp— | H— |
| 71 | (S)-MOM—O— | (S)-Ph— | 1,4-Ph— | Me— | tri-F—Pr— | H— |
| 72 | (S)-HO— | (S)-Ph— | 1,4-Ph— | Me— | tri-F—Pr— | H— |
| 73 | (S)-MOM—O— | (S)-Ph | 1,4-Ph | Me | 2-(S)-HO—Pr | H |
| 74 | (S)-OH | (S)-Ph— | 1,4-Ph— | Me— | 2-(S)-HO—Pr— | H— |
| 75 | (S)-MOM—O— | (R)-3-MOM—O—Ph— | 1,4-Ph— | Me— | Pr— | H— |
| 76 | (S)-HO— | (R)-3-t-Boc—MeO—Ph— | 1,4-Ph— | Me— | Pr— | H— |
| 77 | (S)-HO— | (R)-3-Car—MeO—Ph— | 1,4-Ph— | Me— | Pr— | H— |
| 80 | (S)-MOM—O— | (S)-Ph— | 1,4-Ph— | Me— | penta-F—Pr— | H— |
| 81 | (S)-HO— | (S)-Ph— | 1,4-Ph— | Me— | penta-F—Pr— | H— |
| 82 | (S)-MOM—O— | (S)-Ph— | 1,4-Ph— | Me— | t-Am— | H— |
| 83 | (S)-HO— | (S)-Ph— | 1,4-Ph— | Me— | t-Am— | H— |

TABLE 1-continued
(I)
| Ex.-# | A | Ar¹ | Ar² | R¹ | R² | R³ |
|---|---|---|---|---|---|---|
| 84 | (S)-MOM—O— | (S)-Ph— | 1,4-Ph— | Me— | t-Bu— | H— |
| 85 | (S)-HO— | (S)-Ph— | 1,4-Ph— | Me— | t-Bu— | H— |
| 87 | (S)-MOM—O— | (S)-Ph— | 1,4-Ph— | HO— | Pr— | H— |
| 88 | (S)-HO— | (S)-Ph— | 1,4-Ph— | HO— | Pr— | H— |
| 89 | (S)-F— | (S)-Ph— | 1,4-Ph— | Me— | 2-(S)-HO—Pr— | H— |
| 91 | (S)-F— | (S)-Ph— | 1,4-Ph— | HO— | Pr— | H— |
| 94 | (R)-F— | (S)-Ph— | 1,4-Ph— | Me— | Pr— | H— |
| 95 | (S)-F— | (R)-Ph— | 1,4-Ph— | Me— | Pr— | H— |
| 96 | (S)-Cl— | (S)-Ph— | 1,4-Ph— | Me— | Pr— | H— |
| 97 | (S)-Cl— | (S)-Ph— | 1,4-Ph— | Me— | 2-(S)-HO—Pr— | H— |
| 98 | (S)-Cl— | (S)-Ph— | 1,4-Ph— | Me— | 2-(R)-HO—Pr— | H— |
| 99 | O= | (S)-Ph— | 1,4-Ph— | Me— | Pr— | H— |
| 100 | (S)-HO— | (S)-Ph— | 1,4-Ph— | Me— | Pr— | H— |
TABLE 2
Example 23
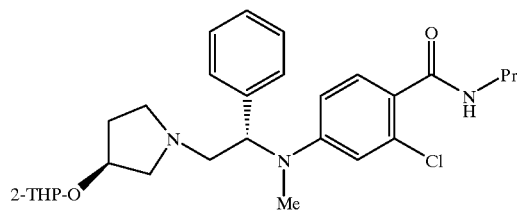
Example 24
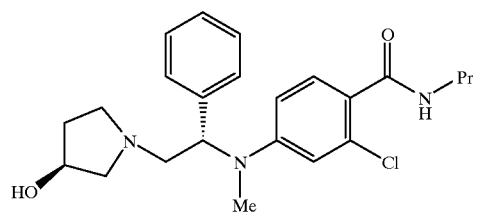
Example 25
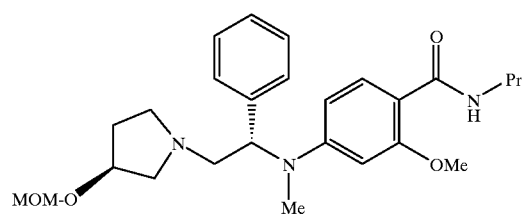
TABLE 2-continued
Example 26
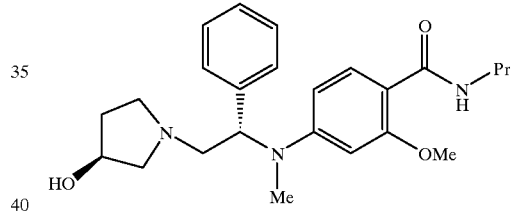
Example 27
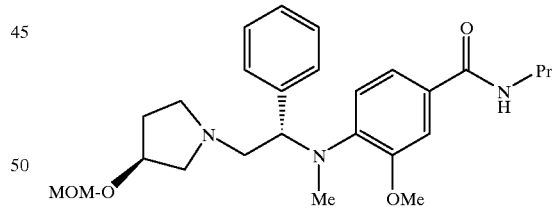
Example 28
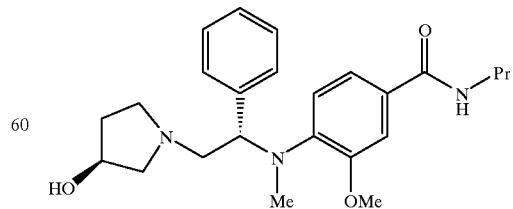

TABLE 2-continued
Example 29
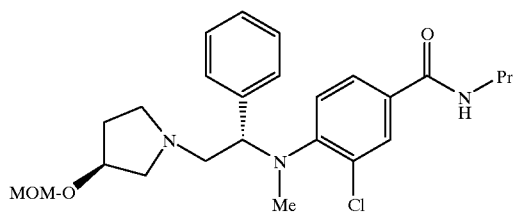
Example 30
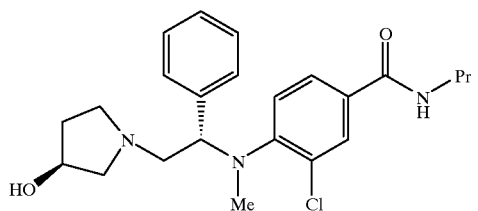
Example 31
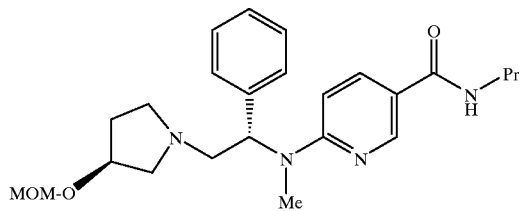
Example 32
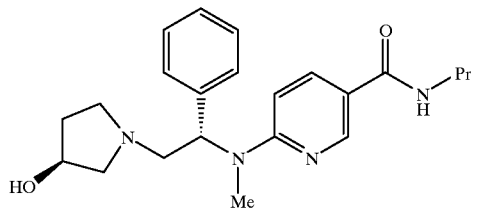
Example 39
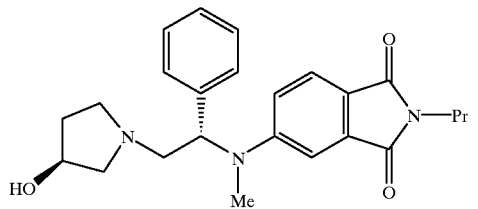
Example 49
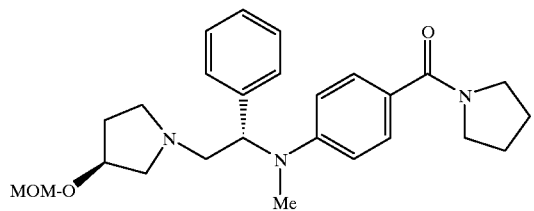
TABLE 2-continued
Example 50
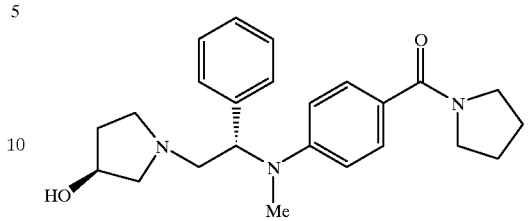
Example 53
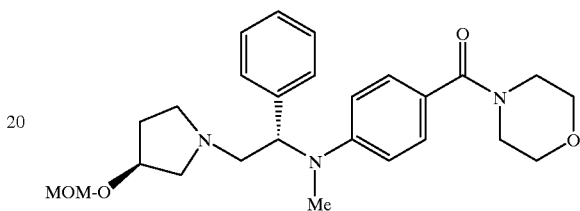
Example 54
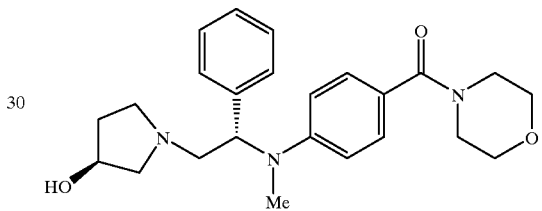
Example 78
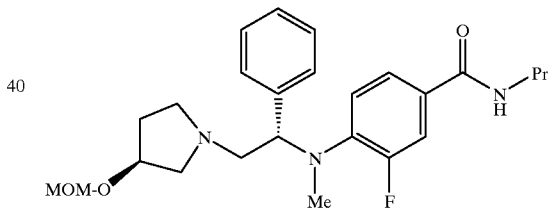
Example 79
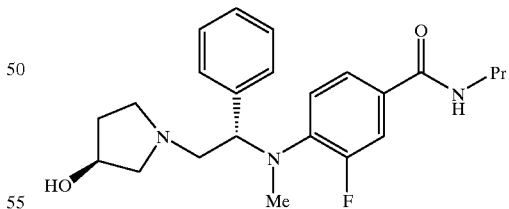
Example 86
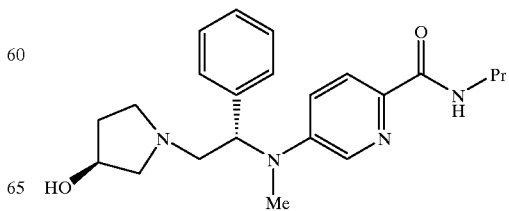

TABLE 2-continued

Example 90

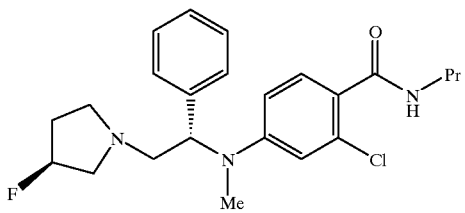

Example 92

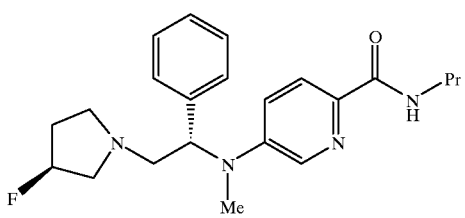

Example 93

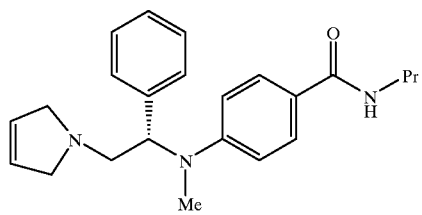

What is claimed is:

1. A compound of the following formula:

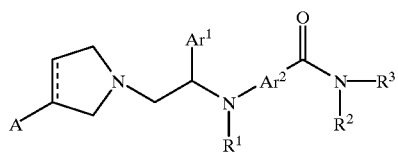

(I)

and the salts thereof, wherein

A is hydrogen, halo, hydroxy, $C_1$–$C_6$ alkyl, halo $C_1$–$C_6$ alkyl, $C_1$–$C_6$ alkoxy, halo $C_1$–$C_6$ alkoxy, oxo, OY wherein Y is a hydroxy protecting group, or absent;

the broken line represents an optional double bond with proviso that if the broken line is a double bond, then A is absent;

$Ar^1$ is phenyl optionally substituted by one or more substituents selected from halo, hydroxy, $C_1$–$C_4$ alkyl, $C_1$–$C_4$ alkoxy, $C_1$–$C_4$ alkoxy-$C_1$–$C_4$ alkoxy, $CF_3$, carboxy-$C_1$–$C_4$ alkoxy and $C_1$–$C_4$ alkoxy-carbonyl-$C_1$–$C_4$ alkoxy;

$Ar^2$ is pyrimidyl, optionally substituted by one or more substituents selected from halo, hydroxy, amino, nitro, carboxy, $C_1$–$C_4$ alkyl, $C_1$–$C_4$ alkoxy, $C_1$–$C_4$ alkylamino, di $C_1$–$C_4$ alkylamino, halo $C_1$–$C_4$ alkyl, $C_1$–$C_4$ alkythio and sulfonyl methyl;

$R^1$ is hydrogen, hydroxy, $C_1$–$C_4$ alkyl, $C_1$–$C_4$ alkoxy or OY wherein Y is a hydroxy protecting group; and $R^2$ and $R^3$ are independently selected from hydrogen, hydroxy, $C_1$–$C_7$ alkyl optionally substituted by one or more hydroxy or halo, $C_3$–$C_6$ cycloalkyl, $C_2$–$C_6$ alkenyl, $C_2$–$C_6$ alkynyl, $C_1$–$C_7$ alkoxy, phenyl optionally substituted by halo, phenyl $C_1$–$C_7$ alkyl, halo substituted phenyl $C_1$–$C_7$ alkyl, and $(CH_2)nX$-$R^4$ wherein n is one or two; X is O, NH or S and $R^4$ is $C_1$–$C_3$ alkyl, or $R^2$ and $R^3$, together with the nitrogen atom to which they are attached, form a pyrrolidine, piperidine or morpholine ring, optionally substituted by $C_1$–$C_3$ alkyl or halo.

2. A pharmaceutical composition for the treatment of a medical condition for which agonist activity toward opioid kappa receptor is needed, in a mammalian subject, which comprises a therapeutically effective amount of a compound according to claim 1, and a pharmaceutically inert carrier.

3. A pharmaceutical composition according to claim 2, which is useful as an analgesic, anesthetic, anti-inflammatory or neuroprotective agent, or useful in the treatment of arthritis, stroke or functional bowel disease.

4. A method for the treatment of a medical condition for which agonist activity toward opioid kappa receptor is needed, in a mammalian subject, which comprises administering to said subject a therapeutically effective amount of a compound according to claim 1.

* * * * *